US009371527B2

(12) United States Patent (10) Patent No.: US 9,371,527 B2
Thornton et al. (45) Date of Patent: Jun. 21, 2016

(54) COMPOSITIONS AND METHODS RELATED TO PROTEIN DISPLACEMENT THERAPY FOR MYOTONIC DISTROPHY

(71) Applicants: University of Rochester, Rochester, NY (US); University of Florida Research Foundation, Inc., Gainsville, FL (US)

(72) Inventors: Charles A. Thornton, Rochester, NY (US); Thurman Wheeler, Rochester, NY (US); Krzysztof Sobczak, Poznan (PL); Robert Osborne, Essex (GB); Jill Miller, Rockport, NY (US); Maurice Scott Swanson, Gainsville, FL (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 14/297,137

(22) Filed: Jun. 5, 2014

(65) Prior Publication Data

US 2015/0080452 A1 Mar. 19, 2015

Related U.S. Application Data

(63) Continuation of application No. 12/442,354, filed as application No. PCT/US2007/020503 on Sep. 21, 2007, now abandoned.

(60) Provisional application No. 60/826,396, filed on Sep. 21, 2006.

(51) Int. Cl.
| | |
|---|---|
| *C12Q 1/68* | (2006.01) |
| *A61K 38/14* | (2006.01) |
| *A61K 31/7088* | (2006.01) |
| *C12N 5/00* | (2006.01) |
| *C12N 15/113* | (2010.01) |
| *G01N 33/50* | (2006.01) |
| *G01N 33/68* | (2006.01) |
| *A61K 31/5375* | (2006.01) |
| *A61K 31/7036* | (2006.01) |
| *A61K 47/48* | (2006.01) |

(52) U.S. Cl.
CPC .......... *C12N 15/113* (2013.01); *A61K 31/5375* (2013.01); *A61K 31/7036* (2013.01); *A61K 47/48046* (2013.01); *C12Y 207/11001* (2013.01); *G01N 33/5008* (2013.01); *G01N 33/6872* (2013.01); *G01N 33/6887* (2013.01); *G01N 33/6893* (2013.01); *C12N 2310/11* (2013.01); *C12N 2310/3233* (2013.01); *C12N 2310/3515* (2013.01); *G01N 2500/02* (2013.01); *G01N 2800/2878* (2013.01)

(58) Field of Classification Search
None
See application file for complete search history.

(56) References Cited

U.S. PATENT DOCUMENTS

| | | |
|---|---|---|
| 6,268,479 B1 | 7/2001 | Stern et al. |
| 2002/0114814 A1 | 8/2002 | Gray et al. |
| 2003/0235865 A1 | 12/2003 | Epps et al. |
| 2004/0106555 A1 | 6/2004 | German |
| 2005/0070494 A1 | 3/2005 | Cutroneo et al. |
| 2005/0112118 A1 | 5/2005 | Cimbora et al. |
| 2005/0214823 A1 | 9/2005 | Blume et al. |
| 2005/0233455 A1* | 10/2005 | Damha et al. ............ 435/455 |
| 2006/0148740 A1* | 7/2006 | Platenburg ............... 514/44 |
| 2010/0184833 A1* | 7/2010 | De Kimpe et al. ........ 514/44 R |

FOREIGN PATENT DOCUMENTS

| | | |
|---|---|---|
| JP | 2003-518948 | 6/2003 |
| JP | 2006-508685 | 3/2006 |
| WO | WO 0138566 A2 | 5/2001 |
| WO | WO 2005003386 A2 | 1/2005 |
| WO | WO 2005/010532 A1 | 2/2005 |
| WO | WO 2005086825 A2 | 9/2005 |

OTHER PUBLICATIONS

Furling, et al. (2003) "Viral vector producing antisense RNA restores myotonic dystrophy myoblast functions." Gene Therapy, v.10:795-802.*
Canadian Official Action dated Apr. 8, 2015 for Canadian Patent Application No. 2,664,189; 6 pages.
Lin, et al. "Failure of MBLN-1 dependent post-natal splicing transitions in myotonic dystrophy," Human Molecular Genetics, May 2006, vol. 15, No. 13, pp. 2087-2097.
Ho, et al. "Muscleblind proteins regulate alternative splicing," EMBO Journal, 2004, vol. 23, pp. 3103-3112.
Ho, et al. "Colocalization of muscleblind with RNA foci is separable from mis-regulation of alternative splicing." Journal of Cell Science, 2005, vol. 118, No. 13, pp. 2923-2933.
Kanadia, et al. "Developmental expression of mouse muscleblind genes Mbn11, Mbn12 and Mbn13," Gene Expression Patterns 2003, vol. 3, pp. 459-462.
Kanadia, et al. "Reversal of RNA Missplicing and myotonia after muscleblind overexpression in a mouse poly (CUG) model . . . " PNAS, Aug. 2006, vol. 103, No. 31, pp. 11748-11753.
Kanadia, et al. "A muscleblind knockout model for myotonic dystrophy," Science, Dec. 2003 vol. 302, pp. 1978-1980.
Jiang, et al. "Myotonic dystrophy type 1 is associated with nuclean foci of mutant RNA sequestration of . . . " Human Molecular Genetics, 2004, vol. 13, No. 2, pp. 3079-3088.
Yoshihiro, et al. "Muscleblind protein, MBNL/EXP, binds specifically to CHHG repeats" Human Molecular Genetics, Mar. 2004, vol. 13, No. 5, pp. 495-507.

(Continued)

*Primary Examiner* — Jennifer Pitrak McDonald
(74) *Attorney, Agent, or Firm* — Smith Gambrell & Russell LLP

(57) ABSTRACT

Disclosed are compositions and methods related to the interaction of polyCUG and polyCCUG repeat RNA and proteins that bind to these repetitive RNA sequences. Also disclosed are methods of treating DM1 or DM2 comprising inhibiting the interaction of poly(CUG)$^{exp}$ or poly(CCUG)$^{exp}$ RNA with muscleblind proteins, or by causing improvement of spliceopathy in myotonic dystrophy.

13 Claims, 31 Drawing Sheets

(56) References Cited

OTHER PUBLICATIONS

Burke, et al. "Development and Applicattion of Fluorescence Polarization Assays . . . " Current Topics in Medicinal Chemistry, May 2003, vol. 6, No. 3, pp. 183-194.
Langlois, et al. "Hammerhead Ribozyme-Mediated Destruction of Nuclear Foci . . . " Journal of the Amer. Society of Gene Therapy, May 2003, vol. 7, No. 5, pp. 670-680.
Ishura, et al. "Regulation of splicing by MBNL and CELF family of RNA binding protein," Journal of Med. Society of Myology, Oct. 2005, vol. 24, No. 2, pp. 74-77.
Chapman, et al. "Small Molecule Modulators of HIV REV/REV response element interaction identified . . . " Antiviral Research, Jan. 2002, Vo. 54, No. 3, pp. 149-162.
Mahadevan, et al. "Reversible model of RNA toxicity and cardiac conduction defects in myotonic dystrophy" Nat Genet., Sep. 2006, 11 pages.
Komiyama, et al. "PNA for One-Base Differentiating Protection of DNA from Nuclease . . . " Journal of American Chemical Society, Nov. 2002, vol. 125, pp. 3758-3762.
European Office Action dated Apr. 10, 2015 for European Patent Application No. 07861357.7; 7 pages.
Japanese Official Action dated Dec. 22, 2014 f or Japanese Application No. 2009-529258; 5 pages.
Kino, et al., "Muscleblind protein, MBNL1/EXP, binds specifically to CHHG repeats," Human Molecular Genetics, 2004, vol. 13, No. 5, pp. 495-507.
European Communication Pursuant to Article 94(3) dated Dec. 19, 2014; 5 pages.
Japanese Official Action dated Sep. 19, 2014 for Japanese Application No. 2013-259362; 4 pages.
Kanadia, Rahul, et al., "Reversal on RNA missplicing and myotonia after muscleblind . . . " PNAS, vol. 103, No. 31, Aug. 1, 2006, pp. 11748-11753.
Rackham, et al., "Visualization of RNA-protein interaction in living cells: FMRP and IMP1 interact on mRNAs," The EMBO Journal, vol. 23, No. 16, 2004.
Japanese Official Action released by the Japanese Patent Office on Jan. 28, 2016; 6 pages.

\* cited by examiner

| GST-MBNL1-41 | MBNL1-41 | protein | [nm] |
|---|---|---|---|
| — | — | 100 | 0.4 |
| — | — | 50 | 0.2 |
| — | — | 25 | 0.1 |
| — | — | 12.5 | 0.05 |
| — | — | 6.2 | 0.025 |
|  |  | 3.1 | 0.012 |
|  |  | 1.6 | 0.0 |
|  |  | 0.8 | 0.0 |

FIG.3A

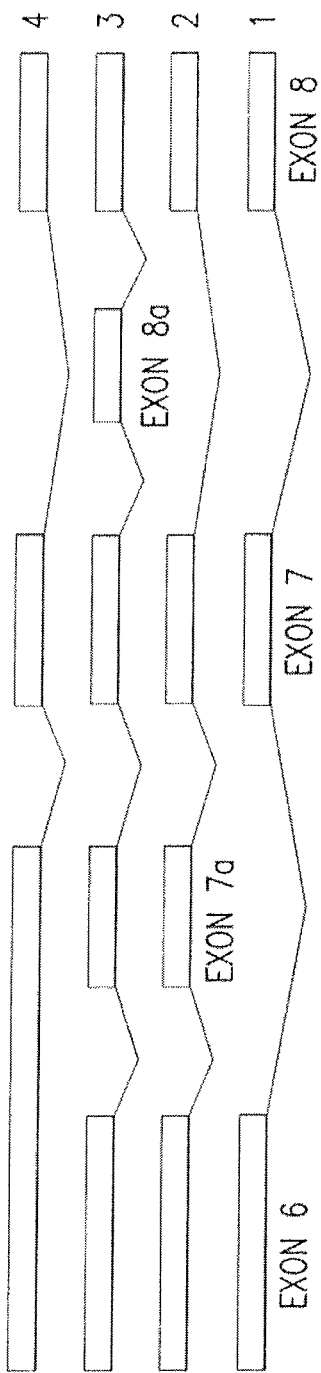
FIG.21B
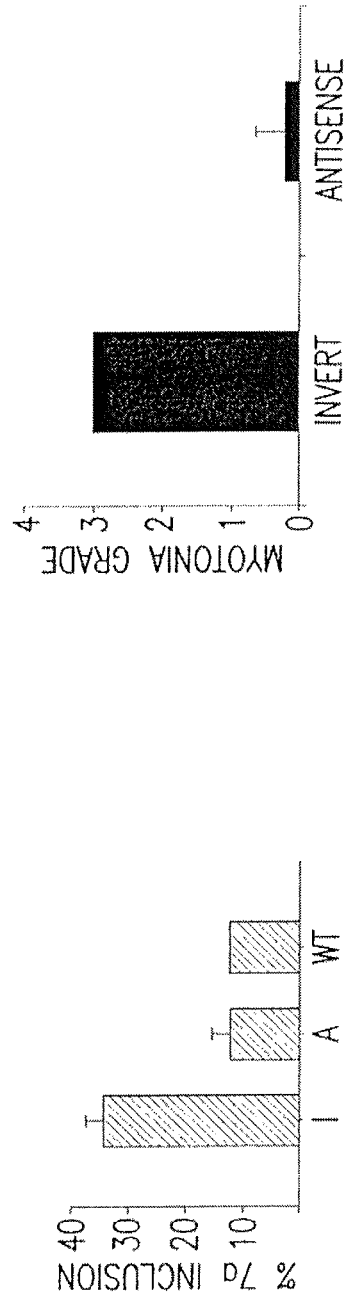
FIG.21C
FIG.21D

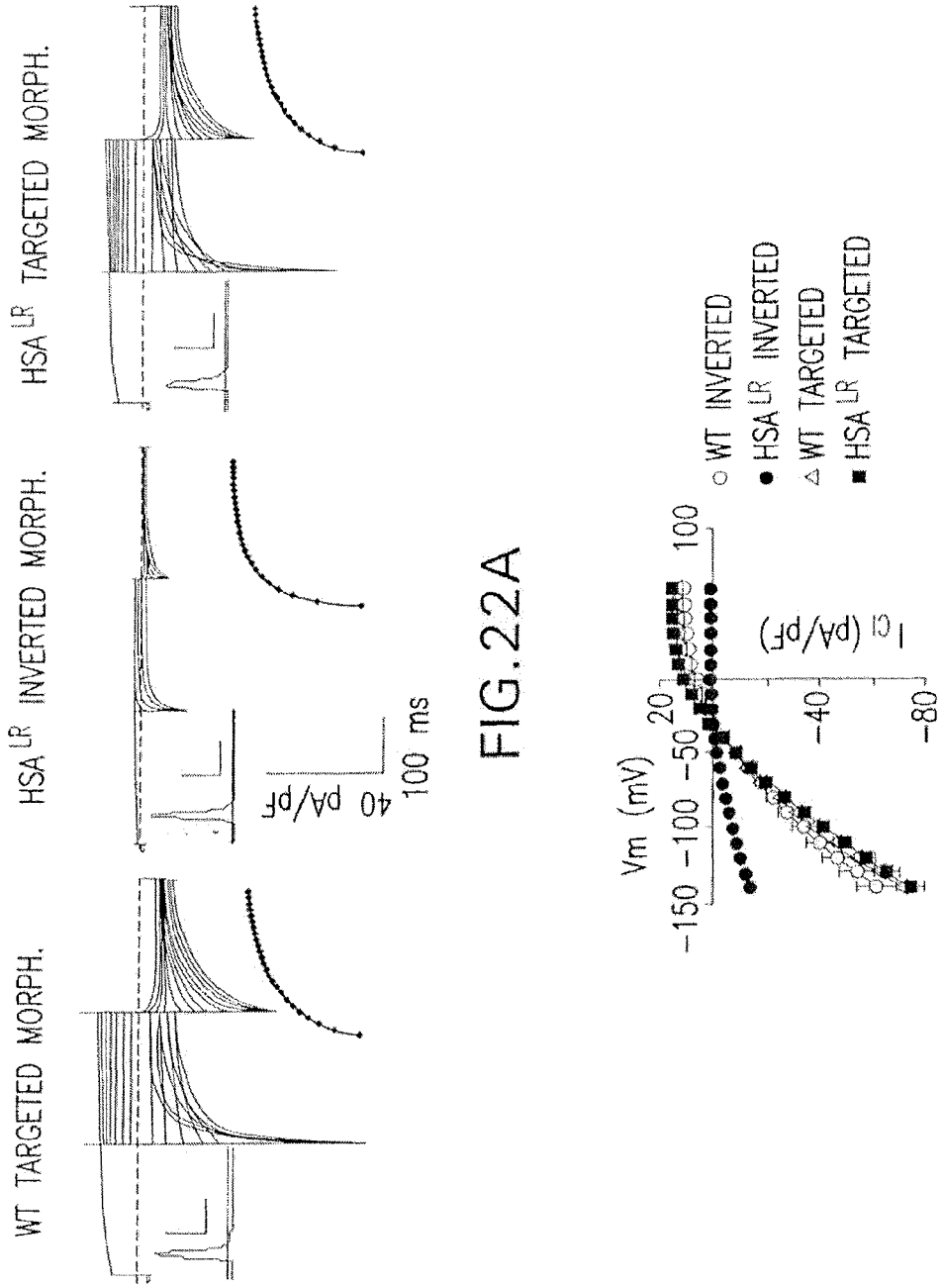

MORPHOLINO DESIGN
       INTRON 6       EXON 7a
5'-gugcuucucuguugcagACCGUGCCUGGGCA-3'
   |||||||||||||||||||||||||||||||
   3'-gaagagacaacgtCTGGCACGGACC-5'
            ANTISENSE 1

EXON 7a       INTRON 7a
5'-GCCCCTGAUGGAGgcaaguuucacuuccucc-3'
   |||||||||||||||||||||||||||||||
   3'-GGACTACCTCcgttcaaagtgaagg-5'
            ANTISENSE 2

5 -gaagagacaacgtcTGGCACGGACC-3
         INVERT CONTROL

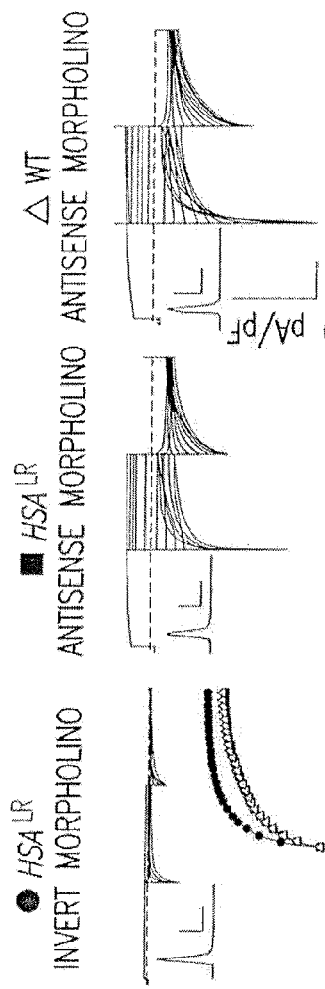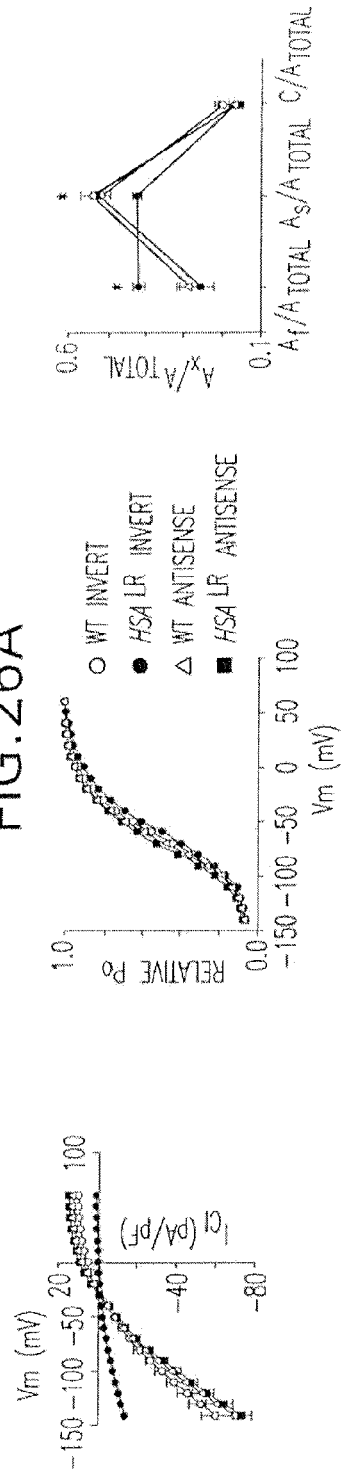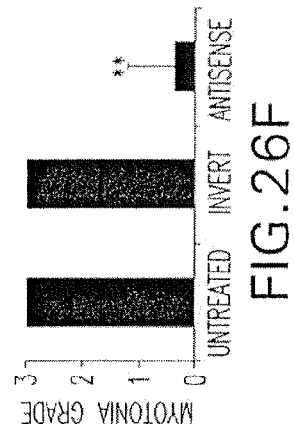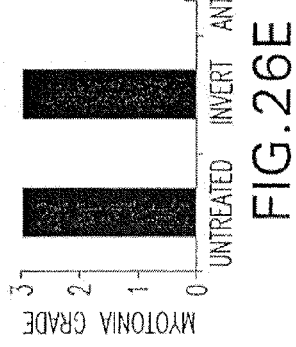

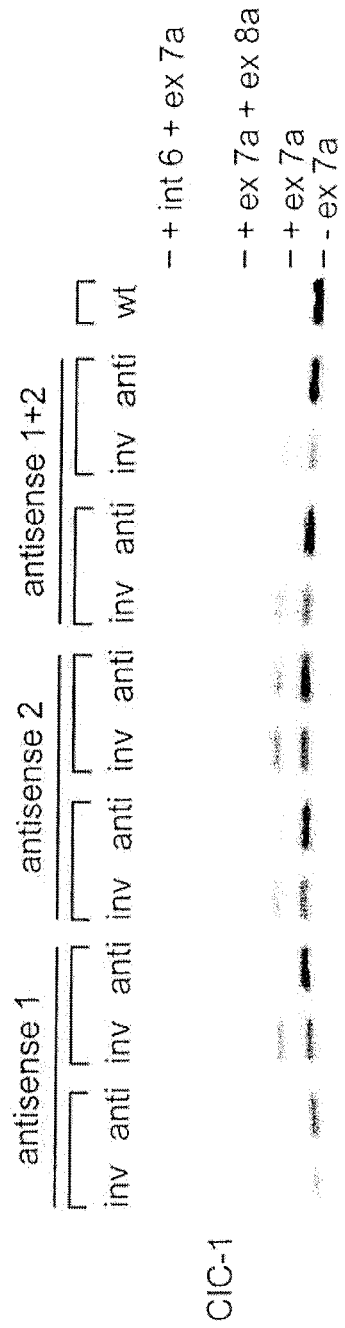

invert merge
antisense invert

MBNL1
antisense invert

CUG$^{EXP}$ RNA
antisense

SEQUENCE LISTING

```
<160> NUMBER OF SEQ ID NOS: 15

<210> SEQ ID NO 1
<211> LENGTH: 4207
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 1
gaatgagttg tggcgcccac aatgctccca tgacaaggag ctgacaagtt ccattttccg      60
tcgcgggcat cttggaatca tgactcccac aatgccttgg gcacttggtc gacagtgggg     120
ccgcctctga aaaaaaatg tgagagcagt cactcaggaa atgttgttta aggggaacct     180
tctggatcct tttcatggca ccatggcaag aagaagctgt atcttatcta tggaagataa     240
agcatggagt tggctaatgg atgctgatag gaccatctag ttgcaggaaa acaagctcag     300
ggctcccact gattctacat tatgggccgt tgctccaggg agaactgcaa atatcttcat     360 ccaccccac atttaaaaac gcagttggag ataaatggac gcaataactt gattcagcag     420
aagaacatgg ccatgttggc ccagcaaatg caactagcca atgccatgat gcctggtgcc     480
ccattacaac ccgtgccaat gttttcagtt gcaccaagct tagccaccaa tgcatcagca     540
gccgccttta atccctatct gggacctgtt tctccaagcc tggtcccggc agagatcttg     600
ccgactgcac caatgttggt tacagggaat ccgggtgtcc ctgtacctgc agctgctgca     660
```

```
gctgctgcac agaaattaat gcgaacagac agacttgagg tatgtcgaga gtaccaacgt    720
ggcaattgca accgaggaga aaatgattgt cggtttgctc atcctgctga cagcacaatg    780
attgacacca atgacaacac agtcactgtg tgtatggatt acatcaaagg gagatgctct    840
cgggaaaagt gcaaatactt tcatccccct gcacatttgc aagccaagat caaggctgcc    900
caataccagg tcaaccaggc tgcagctgca caggctgcag ccaccgcagc tgccatgact    960
cagtcggctg tcaaatcact gaagcgaccc ctcgaggcaa cctttgacct gggaattcct   1020
caagctgtac ttcccccatt accaaagagg cctgctcttg aaaaaaccaa cggtgccacc   1080
gcagtcttta acactggtat tttccaatac caacaggctc tagccaacat gcagttacaa   1140
cagcatacag catttctccc accaggctca atattgtgca tgacacccgc tacaagtgtt   1200
gttcccatgg tgcacggtgc tacgccagcc actgtgtccg cagcaacaac atctgccaca   1260
agtgttccct tcgctgcaac agccacagcc aaccagatac ccataatatc tgccgaacat   1320
ctgactagcc acaagtatgt tacccagatg tagaattttc atcactaaac aatcatgcta   1380
aagaggaaag gacagtgtgc ttggttagag taaaggacga ggtcattagc catattgtat   1440
atatcgtcaa gcaacacaca caaaagttcc tcagccacaa gacatccaca tattgcatgt   1500
taaccagaag aaaagacaac attttccgga aatccactgc acactgttgc ctatacactt   1560
tgtacattta attgatattt gtgctgaggt gatattcctg tctaaaagaa caacattgtc   1620
tttcttttct agcacagagt tatgcattca agatgcata cctagttagt ttcctatata   1680
ttcatgccat cttgaaaaga cagactatgg tgtaaccatg attctattat gtattggtac   1740
gtctgtagac caagatataa ttttttaaaa ataagtttat ttctttcaag gtttacaaat   1800
aacaaaggtg caccttgtat ttaaaattgc cattatagat gagagcgtgc atgcacagtc   1860
atttttgttt aagagtaata ttttttaatgt aatagattgt aagacgtggt gagggaggga   1920
tctgacagag atgaatgtgc caagcaaaac cacaactgtg tatattttaa agcacatcat   1980
ggctttaagt accatgttgt taaggattct catgaagtgc catagactgt acatcaaatt   2040
agagtattat ttcttcagtg ttattgtttt cagagccaca ttttgttgca tatttgctag   2100
tactaatcag tcaaagggca ccattctttt tttttttttt gaaaccaaag ctgtctcaga   2160
aatggccaat ttaactttac agtaacaata gacagcacaa cacaaactct ctcaatacag   2220
ataaactcac acatactgga gatatatata taatagatat atataaaatt attttaatgc   2280
attgtagtgt aatatttatg catactatac tgtataacat gttattcaaa agggattgcc   2340
atttctgaga cacagtaaca aaaaaatgag gaaattattt tgcttctatt tatagcctct   2400
gtcaaaagtc aaaagactat aaatgctttg caaaaatggt ttcacgtttg cttaaatgct   2460
tcatcacagt cacattcaaa atagtgactc taaacaaaga agaaagcagc actgtcatca   2520
gatgcatgat aaaccaaaat atgaaaatgg gaaatgttta attaacctag taattgggtg   2580
ggttaagtac atgggtgaat tttatatgtg attttttgttt tgttttgttt tgttcagatt   2640
aactgcttat agccttagaa agcctttttac aaaattaaaa aaaaaaaaat agatgtgcat   2700 tcagtttta agaatggaat catccaaagg aattccttttt tttgaggttt ggatgttgca   2760
gctagtaaag gatattttttg ctctgttcag cagttctaaa aattgctgaa gtaggggcca   2820
ggtcactggt agttatagta tggaatggga gaagtgaaag ttcagttata gaactttcca   2880
tacttccaag tttactgcaa gttttttatgc ttgagagaga tgcttttctaa tataagactg   2940 atgtgttgat tttactgatt gtactgtaca tctattaaag ccttagatta ttacattacg   3000
```

-continued

```
ggttggaacc cataccaatg taatttcaat cgtgttaaga aagtaatggt gacttcacat    3060
gttattgtag ttagttacat tatagaatat tacttatttt tcttgttaaa atgtagtttt    3120
tcatttccta catttattag attttcattt tctattaaca attgaatacc atttcagttt    3180
atagacttgt tttattagat tttaccaatg aattttcaa atacaaaaa aaagtagttt     3240 ttccttcata acatactcag ttttgaatta catgtagtgt cacatgaata ttcgtattgt    3300
taactaaatg atttatattt tactgattta atattacagt gtaagaatgt cagtcattgt    3360
tagttcttgt ctagttttca ttaaaagaac aaagatcttt tatatggata tcttataaat    3420
atataatcat tgctaagtaa gaagttaagt tgttgctatc gcaacaatcc tggcagacaa    3480
ttgagtaata ttttgatgat ttattttgtt tgtaattagt tattataaga agatctagat    3540
cctagatatt agaataaaat ttatttttcta ctgtatccat ttcaaatgtt aaaatattgt    3600
ttaatatttt tgaaatccct gagtatcagg ccttgttata aataagctgc ataatcaata    3660
aatagaacaa gggacttttt gttgataatc caaatactca aagtttacgt aatgaaaatt    3720
atagcgtgtg tgcaaactct tgagggttga ttatgctgca atttagcatg ttggaacgtc    3780
tagggagaag gttgactttt tgcacttctg tatatagtca aaagagagaa acctgtataa    3840
tagtaagatc ttattttgaa taaaaacgtc tataattaca aggagttttg ttaaggctaa    3900
tacaatgaca gactgagcaa aattgcttgc aaaagtggca cagagttagc actccatacc    3960
ccttcaaaca tgttgctttg ctttcttgtg gacagcttgt agtttgccag gatttttttca    4020 gctggaaaga tacgccatcc tttcaaaccc tcatgactga caaaaactcc atggggccaa    4080
atctgcctga agatcattac caaaaatagc aggtacttct accattaagg tgaaatcatg    4140
gatcagatat tccttacatt tttcaaaact actgcatgtt taaaacttca acaaaaaaaa    4200
aaaaaaa                                                              4207
```

<210> SEQ ID NO 2
<211> LENGTH: 343
<212> TYPE: PRT
<213> ORGANISM: Artificial Sequence
<220> FEATURE:
<223> OTHER INFORMATION: Description of Aritificial Sequence: note = synthetic construct

<400> SEQUENCE: 2

```
Met Gly Arg Cys Ser Arg Glu Asn Cys Lys Tyr Leu His Pro Pro
  1               5                  10                  15

His Leu Lys Thr Gln Leu Glu Ile Asn Gly Arg Asn Asn Leu Ile Gln
             20                  25                  30

Gln Lys Asn Met Ala Met Leu Ala Gln Gln Met Gln Leu Ala Asn Ala
         35                  40                  45

Met Met Pro Gly Ala Pro Leu Gln Pro Val Pro Met Phe Ser Val Ala
     50                  55                  60

Pro Ser Leu Ala Thr Asn Ala Ser Ala Ala Phe Asn Pro Tyr Leu
 65                  70                  75                  80

Gly Pro Val Ser Pro Ser Leu Val Pro Ala Glu Ile Leu Pro Thr Ala
                 85                  90                  95

Pro Met Leu Val Thr Gly Asn Pro Gly Val Pro Val Pro Ala Ala Ala
                100                 105                 110

Ala Ala Ala Ala Gln Lys Leu Met Arg Thr Asp Arg Leu Glu Val Cys
            115                 120                 125

Arg Glu Tyr Gln Arg Gly Asn Cys Asn Arg Gly Glu Asn Asp Cys Arg
        130                 135                 140
```

-continued

```
Phe Ala His Pro Ala Asp Ser Thr Met Ile Asp Thr Asn Asp Asn Thr
145                 150                 155                 160

Val Thr Val Cys Met Asp Tyr Ile Lys Gly Arg Cys Ser Arg Glu Lys
            165                 170                 175

Cys Lys Tyr Phe His Pro Pro Ala His Leu Gln Ala Lys Ile Lys Ala
        180                 185                 190

Ala Gln Tyr Gln Val Asn Gln Ala Ala Ala Gln Ala Ala Ala Thr
    195                 200                 205

Ala Ala Ala Met Thr Gln Ser Ala Val Lys Ser Leu Lys Arg Pro Leu
210                 215                 220

Glu Ala Thr Phe Asp Leu Gly Ile Pro Gln Ala Val Leu Pro Pro Leu
225                 230                 235                 240

Pro Lys Arg Pro Ala Leu Glu Lys Thr Asn Gly Ala Thr Ala Val Phe
            245                 250                 255

Asn Thr Gly Ile Phe Gln Tyr Gln Gln Ala Leu Ala Asn Met Gln Leu
        260                 265                 270

Gln Gln His Thr Ala Phe Leu Pro Pro Gly Ser Ile Leu Cys Met Thr
    275                 280                 285

Pro Ala Thr Ser Val Val Pro Met Val His Gly Ala Thr Pro Ala Thr
290                 295                 300

Val Ser Ala Ala Thr Thr Ser Ala Thr Ser Val Pro Phe Ala Ala Thr
305                 310                 315                 320

Ala Thr Ala Asn Gln Ile Pro Ile Ile Ser Ala Glu His Leu Thr Ser
            325                 330                 335

His Lys Tyr Val Thr Gln Met
        340

<210> SEQ ID NO 3
<211> LENGTH: 25
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 3
agcagcagca gcagcagcag cagca                                          25

<210> SEQ ID NO 4
<211> LENGTH: 25
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 4
ccaggcacgg tctgcaacag agaag                                          25

<210> SEQ ID NO 5
<211> LENGTH: 25
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 5
gaagagacaa cgtctggcac ggacc                                          25
```

```
<210> SEQ ID NO 6
<211> LENGTH: 25
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 6
ggaagtgaaa cttgcctcca tcagg                                         25

<210> SEQ ID NO 7
<211> LENGTH: 24
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 7
tgaaggaata cctcacactc aagg                                          24

<210> SEQ ID NO 8
<211> LENGTH: 20
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 8
cacggaacac aaaggcactg                                               20

<210> SEQ ID NO 9
<211> LENGTH: 21
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 9
gtgtgagtcg ctccagaaac g                                             21

<210> SEQ ID NO 10
<211> LENGTH: 23
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 10
ccaccacagg accatgttat ttc                                           23

<210> SEQ ID NO 11
<211> LENGTH: 31
<212> TYPE: RNA
<213> ORGANISM: Artificial Sequence
<220> FEATURE:
<223> OTHER INFORMATION: Description of Aritificial Sequence: note =
      synthetic construct

<400> SEQUENCE: 11
gugcuucucu guugcagacc gugccugggc a                                  31
```

```
<210> SEQ ID NO 12
<211> LENGTH: 31
<212> TYPE: RNA
<213> ORGANISM: Artificial Sequence
<220> FEATURE:
<223> OTHER INFORMATION: Description of Aritificial Sequence: note =
      synthetic construct

<400> SEQUENCE: 12
gccccugaug gaggcaaguu ucacuuccuc c                                      31

<210> SEQ ID NO 13
<211> LENGTH: 25
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 13
ggactacctc cgttcaaagt gaagg                                             25

<210> SEQ ID NO 14
<211> LENGTH: 12
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 14
cagcagcagc ag                                                           12

<210> SEQ ID NO 15
<211> LENGTH: 15
<212> TYPE: DNA
<213> ORGANISM: Artificial Sequence
<220> FEATURE:
<223> OTHER INFORMATION: Description of Aritificial Sequence: note =
      synthetic construct

<400> SEQUENCE: 15
cagcagcagc agcag                                                        15
```

COMPOSITIONS AND METHODS RELATED TO PROTEIN DISPLACEMENT THERAPY FOR MYOTONIC DISTROPHY

This application claims the benefit of U.S. Provisional Application No. 60/826,396, filed on Sep. 21, 2006 which is incorporated herein in its entirety.

This work was funded by National Institutes of Health Grant No. NIH/AR46806, NIH/AR/NS48143 and NIH/NS48843, the government has certain rights in the invention.

BACKGROUND

Myotonic Dystrophy type 1 (DM1) is autosomal dominant and characterized by progressive weakness, muscle wasting, myotonia, and multisystem impairment (abnormal cardiac conduction, neuropsychiatric impairment, cataracts). Disability occurs at an early stage due to preferential involvement of hand muscles by myotonia and weakness. Death from respiratory failure, aspiration, or cardiac arrhythmia occurs at a median age of 55, usually after several decades of severe disability. Presently there is no treatment other than supportive care. DM1 is caused by expansion of a CTG repeat in the 3' untranslated of DMPK, the gene encoding dystrophia myotonica protein kinase. Individuals with small CTG repeat expansions of 50-100 repeats generally have mild, late-onset symptoms, whereas large expansions of a thousand or more repeats are associated with severe disease in infancy. Associations between repeat length and disease severity have been made with DNA isolated from circulating blood cells. However, it was found that in many tissues, including skeletal muscle and brain, somatic instability of the expanded CTG repeat leads to much larger expansions, of 1,000 to 5,000 repeats, even in individuals with relatively short expansions in circulating blood cells (Thornton C A, et al. Ann Neurol 1994; 35:104-107). Myotonic dystrophy type 2 (DM2) is similar to DM1, but less common and less severe. DM2 is caused by expansion of a CCTG repeat in intron 1 of the ZNF9 gene, encoding a nucleic acid binding protein.

SUMMARY

Disclosed are screening methods and compositions related to Myotonic Dystrophy (DM) type 1 (DM1) and type 2 (DM2). In particular, disclosed herein are methods of screening for compounds effective in treating DM. Also disclosed are compositions capable of treating DM.

Thus, in one aspect, disclosed herein are methods of using antisense oligonucleotides as protein displacement therapy in myotonic dystrophy.

Also disclosed are methods of high throughput screening to find other compounds that can inhibit the interaction of CUG repeat RNA with MBNL1 protein.

Also disclosed are methods of using antisense oligonucleotides to cause exon skipping and correct the splicing defects in myotonic dystrophy.

BRIEF DESCRIPTION OF THE DRAWINGS

The accompanying drawings, which are incorporated in and constitute a part of this specification, illustrate several embodiments and together with the description illustrate the disclosed compositions and methods.

FIG. 1A shows an RT-PCR assay for SERCA1 exon 22 alternative splicing in mouse muscle at postnatal day 2 (P2), P10, P20, and 6 months (Ad) shows postnatal transition to exon 22 inclusion. The postnatal transition is absent in $HSA^{LR}$ transgenic and MBNL1 knockout mice. FIG. 1B shows the inclusion of exon 22 of SERCA1 leads to a termination codon exon 22. Skipping of exon 22 leads to a termination codon in exon 23. Note that the Ex22+ transcript is not subject to nonsense mediated decay because the stop codon is within 55 nt from the final exon junction. FIG. 1C shows the pSERF minigene spliceopathy reporter construct. Human SERCA1 exon 22 and its flanking introns have been included intact. PA, polyadenylation signal. FIG. 1D shows electroporation of pSERF in muscle in vivo shows increased exon 22 inclusion in WT compared to $HSA^{LR}$ transgenic mice (RT-PCR splicing assay 4 days after electroporation).

FIG. 2A shows Coomassie-stained SDS-gels of following samples: crude protein lysate of bacteria expressing GST-MBNL1-41-del105 (truncated at C-terminal to remove hydrophobic domain); supernatant and pellet after 14,000 g centrifugation of crude protein; flow through after Ni-column chromatography; four samples eluted from Ni-column with different concentration of imidazole or EDTA. Next, eluate III was purified on Glutathione Sepharose column (second gel). Fraction I and II are washes with loading buffer; fractions III-V are eluates with 10 mM glutathione. Purity of protein after purification is >90%. FIG. 2B shows the product of fluorescent labeling of both MBNL1-41-del105 with fluorescein (left), and poly(CUG)$^{109}$ labeling at the 3' end by incorporation of TAMRA conjugated to ATP. Note, that relative small amounts of such protein and RNA, as low as 62.5 fmol, are detected both in acrylamide gel (upper FluorImager scan) and microplate (lower scan).

FIGS. 3A, 3B, and 3C show the interaction of recombinant MBNL1 with poly(CUG)$^{109}$. FIG. 3A is in nitrocellulose filter binding assay, a constant concentration of fluorescently-labeled poly(CUG)$^{109}$ [0.1 nM] is mixed with decreasing concentration (from 100 to 0.012 nM) of MBNL1-41 protein fused or not with GST. Unbound RNA washes through filter, protein-bound RNA is retained. Note that protein concentrations listed to the right correspond to two rows of wells on the filter. FIG. 3B shows a comparison of saturation curve for full length and C-terminus truncated GST-MBNL1-41. Note that neither presence of GST-fusion partner nor deletion of 105 aa from C-terminus of MBNL1 have significant influence on poly(CUG)$^{109}$ binding. FIG. 3C shows a diagram showing experimental design for poly(CUG)$^{109}$ attachment assay. The capture oligodeoxynucleotide (ODN) is labeled at the 5' end with biotin via a 12-carbon linker. Interaction of biotin with streptavidin followed by hybridization of capture ODN to the 3' end of poly(CUG)109 tethers the transcript to plates. Poly(CUG)109-MBNL1 interaction is performed with excess of fluorescently-labeled MBNL1 protein.

FIGS. 21A, 21B, 21C, and 21D show the effects of antisense morpholino targeting the 3' splice junction of ClC-1 exon 7a on splicing and myotonia in $HSA^{LR}$ transgenic mice. Antisense morpholino targeting the 3' splice junction of ClC-1 exon 7a was injected into tibialis anterior muscle of $HSA^{LR}$ mice under general anesthesia (sequence 5'-CCAG-GCACGGTCTGCAACAGAGAAG-3' (SEQ ID NO: 4)). The contralateral muscle was injected with morpholino having the inverted sequence (5'-GAAGAGACAACGTCTG-GCACGGACC-3'(SEQ ID NO: 5)). Uptake into muscle fibers was enhanced by in vivo electroporation. The determination of which side received the antisense morpholino was randomized. 21 days later, myotonia was evaluated by electromyography and muscle was harvested for RT-PCR analysis of ClC-1 alternative splicing. Electromyography was blinded to the randomization. FIG. 21A shows RT-PCR analysis of alternative splicing shows that exon 7a inclusion products (bands 2 and 4, see splicing diagram in FIG. 21B) are decreased in muscle treated with antisense morpholino but not by the inverted morpholino. Concurrently, the antisense morpholino increases the fraction of splice products encoding functional ClC-1 channels (band 1). Quantification in graph FIG. 21C confirms that antisense morpholino caused a significant reduction of exon 7a inclusion ($p<0.0001$). FIG. 21D shows that treatment with the antisense morpholino caused a marked reduction of myotonia in the antisense-treated muscle ($p<0.00001$).

FIGS. 22A and 22B show whole-cell voltage clamp from single muscle fibers shows that treatment with antisense morpholino targeting ClC-1 exon 7a restores normal chloride current density in $HSA^{LR}$ transgenic mice. Antisense morpholino targeting the 3' splice junction of ClC-1 exon 7a was injected into foot pad muscle of $HSA^{LR}$ mice under general anesthesia. Uptake into muscle fibers was enhanced by in vivo electroporation. The morpholino was tagged with fluorescein. 4 days later, individual FDB muscle fibers were isolated. Greater than 90% of fibers showed fluorescein uptake, and only these fibers were studied. As a control, the opposite footpad was injected with morpholino having the inverted sequence. FIG. 22A, the upper panel; shows ClC-1 currents at different membrane potentials. The peak current density in $HSA^{LR}$ mice (center panel) is much lower than in wild-type mice (left panel). However, after morpholino treatment in $HSA^{LR}$ mice (right panel), the current density is restored to levels that are similar to wild-type mice. To quantify this effect, FIG. 22B, the graph in the lower panel, shows chloride current density in relation to membrane potential. In fibers treated with inverted morpholino, or in untreated $HSA^{LR}$ fibers, the current density is markedly reduced (closed circles). The antisense morpholino (closed squares) restores chloride current density to normal levels (open circles or triangles).

FIG. 23A shows the inclusion of ClC-1 exon 7a induces a frame shift and premature termination codon in exon 7. Annealing of antisense morpholino to the 3' splice site of exon 7a in the ClC-1 pre-mRNA is intended to prevent spliceosomal recognition of this exon. FIG. 23B shows the alignment of ClC-1 pre-mRNA (top strand) (top strand paired with antisense 1 is SEQ ID NO: 11 and top strand paired with antisense 2 is SEQ ID NO: 12) with antisense morpholinos targeting the 3' (antisense 1 is SEQ ID NO: 4) or 5' (antisense 2 is SEQ ID NO: 6) splice sites of exon 7a is shown. The control morpholino (SEQ ID NO: 5) is the 5'-3' invert of the 3' splice site blocker. Exonic sequences are in upper case, intronic sequences are in lower case.

FIGS. 24A-C show a cross-section of $HSA^{LR}$ tibialis anterior (TA) muscle showing distribution of 3'-carboxyfluorescein-labeled antisense morpholino 3 weeks after injection. The morpholino was complementary to the 3' splice site of ClC-1 pre-mRNA. Muscle fibers are outlined by wheat germ agglutinin (wga) and nuclei are highlighted by DAPI. FIGS. 24D and 24 E show brightfield (D) and fluorescence (E) images of a single FDB fiber showing preferential nuclear localization of the antisense morpholino (post injection day 5). FIGS. 24F and 24G show that as compared to invert-treated control (F), immunofluorescence shows an increase of sarcolemmal ClC-1 protein in HSA$^{LR}$ TA muscle 3 weeks after treatment with antisense morpholino (G). Bars=20 µM.

FIGS. 25A, 25B, 25C, 25D, 25E, and 25F show that antisense morpholino represses splicing of ClC-1 exon 7a. FIG. 25A reveals that RT-PCR showed reduction of exon 7a inclusion three weeks after injection of antisense (anti morpholino (antisense 1+antisense 2, 5 µg each) into TA muscle of HSA$^{LR}$ mice. Pairs of injected TA muscles from each mouse are identified by "1, 2, 3." Muscle injected with control morpholino (inv) (10 µg) was not different from untreated HSA$^{LR}$ muscle. HSA$^{LR}$ and WT mice have the same (FVB) inbred strain background. FIG. 25B shows the inclusion of exon 7a remained partially suppressed 8 weeks after injection of antisense morpholino (20 µg antisense 1 vs. 20 µg invert control). FIG. 25C shows that ClC-1 antisense morpholino did not correct the misregulated alternative splicing of Titin m-line exon 5. FIGS. 25D and 25E show the percentage of ClC-1 splice products that include exon 7a is shown at 3 (D) and 8 (E) weeks following morpholino injection. Mean±s.d.; n=3 per group; **P<0.001; *P=0.035 antisense- versus invert-treated controls; t-test. FIG. 25F shows that the level of ClC-1 mRNA is increased 3 weeks after treatment with antisense moropholino. ClC-1 mRNA level is expressed in arbitrary units relative to housekeeping gene RNA polymerase II transcription factor IIB. Mean±s.d.; n=3 per group; *P=0.06 for antisense vs invert-treated control; t-test.

FIGS. 26A, 26B, 26C, 26D, 26E, and 26F show that antisense morpholino rescues ClC-1 channel function and reverses myotonia in skeletal muscle of HSA$^{LR}$ mice. FIG. 26A shows that representative ClC-1 currents obtained from flexor digitorum brevis (FDB) fibers isolated from HSA$^{LR}$ mice electroporated with either invert (left) or antisense (middle) morpholino and WT mice electroporated with antisense morpholino (right). The dashed lines represent the zero current level. Capacitive currents recorded from each fiber are shown in the insert of each panel (scale bars: vertical, 3 nA; horizontal, 4 ms). Superimposed traces (solid lines) of normalized ClC-1 current deactivation at −100 mV in FDB fibers obtained from invert- (circles) and antisense-treated (squares) HSA$^{LR}$ mice and antisense-treated WT mice (triangles) fit with a second order exponential (symbols) are shown in the insert to the left hand panel. Note that accelerated ClC-1 deactivation kinetics of FDB fibers obtained from HSA$^{LR}$ mice is normalized only following treatment with antisense morpholino. FIG. 26B shows the voltage dependence of average instantaneous ClC-1 current density recorded from FDB fibers of 16-18 day old WT mice treated with invert morpholino (open circles; n=11), WT mice treated with antisense morpholino (open triangles; n=10), HSA$^{LR}$ mice treated with invert morpholino (filled circles; n=12), and HSA$^{LR}$ mice treated with antisense morpholino (filled squares, n=16). FIG. 26C shows the average relative Po-V curves for the same experiments shown in (B). Smooth curves through each dataset were generated using a modified Boltzmann equation (Lueck, J. D., et al. (2007) J Gen Physiol 129:79-94). FIG. 26D shows the average relative contribution of the fast ($A_f/A_{total}$), slow ($A_s/A_{total}$), and non-deactivating ($C/A_{total}$) components of ClC-1 current deactivation elicited from a voltage step to −100 mV for the same experiments shown in (B). Mean±s.e.m.; *P<0.05 invert-treated HSA$^{LR}$ fibers compared to each of the other experimental conditions; t-test. FIGS. 26E and 26F shows that myotonia was significantly reduced 3 (E) and 8 (F) weeks following injection of antisense morpholino. Mean±s.d.; n=3 to 7 per group. Antisense morpholino was injected into one TA, invert morpholino was injected into the contralateral TA, and gastrocnemius muscle served as an untreated control. **P<0.0001 for antisense- vs invert-treated control; ANOVA.

FIG. 27A indicates that RT-PCR shows reduced inclusion of exon 7a at 3 weeks after injection of antisense morpholino 1 (20 µg antisense or invert control). FIG. 27B shows Quantitation of splicing results shown in (A) as mean±s. d.; (n=3 per group); P <0.001 antisense- versus invert-treated control; t-test. FIGS. 27C and 27D shows that immunofluorescence for ClC-1 is increased 3 weeks after injection with antisense (D) as compared to invert-treated control (C). Bar=20 µM. FIG. 27E shows Myotonia in Mbnl1$^{ΔE3/ΔE3}$ TA muscle is reduced 3 weeks after treatment with antisense morpholino but not in muscle treated with invert control. Mean±s.d.; n=3 per group; P<0.0001 antisense- versus invert-treated control; ANOVA.

FIG. 28 shows a Comparison of antisense morpholinos targeting ClC-1 exon 7a. Antisense oligo was injected into tibialis anterior (TA) muscle of HSA$_{LR}$ mice and invert oligo (inv) (20 µg) was injected into the contralateral TA. Tissue was obtained 3 weeks later for analysis of ClC-1 splicing by RT-PCR. Antisense morpholino targeting the 3' splice site (antisense 1; 20 µg) induced a higher level of exon 7a skipping than antisense morpholino directed against the 5' splice site (antisense 2; 20 µg). Effects of antisense 1 alone (20 µg) were similar to co-injection of antisense 1 and 2 (10 µg each) (n=3 each group; 2 from each group are shown).

FIG. 30A shows that PNA-CAG repeat oligos of lengths ranging from 2 to 5 CAG repeats can invade (CUG)$_{109}$ hairpins and effectively interact with expanded CUG repeat hairpin structures in vitro. FIG. 30B shows that these PNA-CAG oligos can also inhibit the interaction of (CUG)$_{109}$ RNA with MBNL1 protein in vitro.

FIG. 33A shows a diagram of enzymatic complementation assay to screen for compounds that inhibit interaction of CUG repeat RNA with recombinant MBNL1 protein. (CUG)109 transcripts are tethered to the surface of a streptavidin-coated microtiter plate using a capture oligonucleotide that is biotinylated. The capture oligo anneals to complementary sequence at the 3' end of the CUG repeat RNA. Recombinant human MBNL1 is expressed as a fusion with the PL fragment of beta-galactosidase. PL is a 55 amino acid fragment of beta-galactosidase. Preliminary experiments determined that fusion of MBNL1 with the PL fragment did not inhibit the binding of MBNL1 protein to CUG repeat RNA. After incubation with test compound, unbound MBNL1-PL is washed away (FIG. 33B). Next, the complementing fragment of beta-galactosidase is added to determine the amount of MBNL1-PL that continues to interact with (CUG)109 RNA and thereby is retained on the microtiter plate. The binding of complementing fragment of beta-galactosidase to PL reconstitutes its enzymatic activity. This activity is then determined by adding substrate to provide a fluorescence or chemiluminescence signal from active beta-galactosidase.

DETAILED DESCRIPTION

Figure 1A:
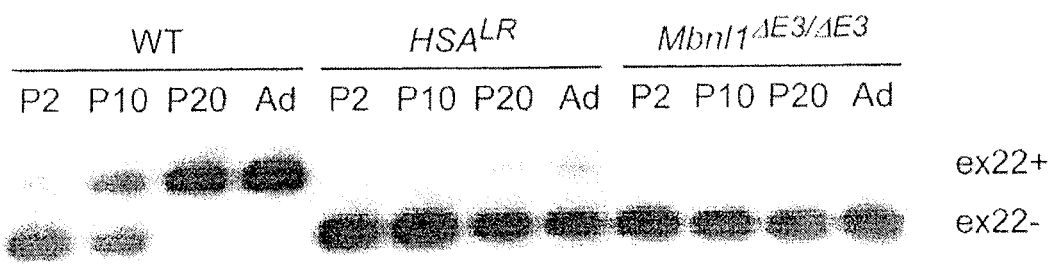
FIGS. 1A, 1B, 1C, and 1D.

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

"Primers" are a subset of probes which are capable of supporting some type of enzymatic manipulation and which can hybridize with a target nucleic acid such that the enzymatic manipulation can occur. A primer can be made from any combination of nucleotides or nucleotide derivatives or analogs available in the art which do not interfere with the enzymatic manipulation.

"Probes" are molecules capable of interacting with a target nucleic acid, typically in a sequence specific manner, for example through hybridization. The hybridization of nucleic acids is well understood in the art and discussed herein. Typically a probe can be made from any combination of nucleotides or nucleotide derivatives or analogs available in the art.

Throughout this application various reference is made to polyCUG repeat RNA or poly(CUG)$^{exp}$ RNA. It is understood and herein contemplated that these terms can be used interchangeably throughout the description and the claims. Likewise, reference is made throughout the application to polyCCUG repeat RNA or poly(CCUG)$^{exp}$. It is also understood and herein contemplated that these terms can be used interchangeably throughout the description and the claims.

Throughout this application, various publications are referenced. The disclosures of these publications in their entireties are hereby incorporated by reference into this application in order to more fully describe the state of the art to which this pertains. The references disclosed are also individually and Myotonic dystrophy type 1 (DM1), the most common form of muscular dystrophy in adults (frequency ~1 in 7,400), is a genetic disease affecting muscle, heart, and brain. DM1 involves a novel disease mechanism in which mRNA from the mutant gene ha a direct toxic effect. The toxic gain-of-function of the mutant mRNA is entirely independent of the protein it encodes.

DM1 is caused by expansion of a CTG repeat in the 3' untranslated region of DMPK, the gene encoding DM protein kinase ((1)). A novel RNA-mediated disease process has recently been elucidated in DM1. Transcripts from the mutant DMPK allele contain an expanded CUG repeat, designated here as poly(CUG)$^{exp}$. The repeat-bearing transcripts are not exported from the nucleus (Taneja K L, et al. J Cell Biol 1995; 128(6):995-1002; Davis B M, et al. Proc Natl Acad Sci USA 1997; 94(14):7388-7393). Instead, they accumulate in nuclear foci. Here, proteins are recruited to the foci, and some of the proteins bind to CUG$^{exp}$ RNA, for example, proteins in the muscleblind (MBNL) family (Miller J W, et al. EMBO J 2000; 19(17):4439-4448). One of the functions of MBNL is to regulate alternative splicing of pre-mRNA. However, sequestration of MBNL proteins in nuclear foci leads to abnormal regulation of alternative splicing for a select group of pre-mRNAs (Kanadia R N, et al. Science 2003; 302(5652): 1978-1980; (6). This is a result of the depletion of MBNL from other regions of the nucleus. This regulatory defect is referred to herein as "spliceopathy." Symptoms of DM1, such as, myotonia, are directly attributable to the effect on splicing regulation (Mankodi A, et al. Mol Cell 2002; 35-44) (ie., spliceopathy). Disclosed herein is evidence that spliceopathy in DM1 muscle can be explained, to a significant extent, by sequestration of a splicing factors in the MBNL family, including muscleblind 1 (MBNL1), muscleblind 2 (MBNL2), and muscleblind 3 (MBNL3). Splicing factors in the MBNL family are also sequestered on nuclear foci of polyCCUG expanded repeats in DM2. For example, it is disclosed herein that (1) MBNL1 is markedly depleted from the nucleoplasm in DM1 muscle cells, as it is recruited into ribonuclear foci; (2) expression of poly(CUG)$^{exp}$ and ablation of MBNL1 have equivalent effects on splicing regulation in mouse skeletal muscle; (3) spliceopathy in DM1 is remarkably similar to that observed in poly(CUG)$^{exp}$-expressing or MBNL1 knockout mice (Lin X, et al. Hum Mol Genet 2006); and (4) spliceopathy in poly(CUG)$^{exp}$-expressing mice is corrected by overexpression of MBNL1. Therefore, poly(CUG)$^{exp}$ and its interaction with MBNL1 are valid targets for therapy.

Among neurogenetic disorders, the possibility of developing effective treatment through the use of high throughput screens for therapeutic agents is especially attractive in the case of DM1. The DM1 mutation does not lead to an absence of essential protein, nor does it create a deleterious effect of mutant protein. Instead, the fundamental problem is mislocalization of MBNL1 and a consequence is the abnormal expression in adult tissue of splice isoforms that are normally expressed in neonatal (immature) tissue (Lin X, et al. Hum Mol Genet 2006). The findings of ribonuclear foci in presymptomatic DM1 patients (Mankodi A, et al. Hum Mol Genet 2001; 10:2165-2170), and in phenotypically normal transgenic mice that have low poly(CUG)$^{exp}$ expression (Mankodi A, et al. Science 2000; 289(5485):1769-1773), indicate that subthreshold accumulation of poly(CUG)$^{exp}$ has no discernable effects on muscle function. Thus, modest reduction of poly(CUG)$^{exp}$ or partial release of MBNL1 from ribonuclear foci translates into large therapeutic effects. By focusing on pharmacotherapy, whole-body therapeutic effects can be achieved as well as the prevention of disease progression. However, based on the character of the disease process, it also disclosed that reversal of phenotype can be achieved. For example, in skeletal muscle, a tissue with great intrinsic regenerative capacity, DM1 produces mainly fiber atrophy with little fibrosis or necrosis, an eminently reversible lesion. In addition, DM1 is a "composite" disease, in which distinct facets of the phenotype can be parsed to effects of spliceopathy on different transcripts, thereby impacting many different pathways. In many cases, the spliceopathy can result in functional impairment rather than irreversible cell degeneration. For example, myotonia in DM1 is a functional defect that results from chloride channelopathy (Mankodi A, et al. Mol Cell 2002; 35-44), and the data indicate that it is reversible in a transgenic mouse model either by AAV-mediated overexpression of MBNL1 or antisense oligonucleotides that target the mis-spliced exon. By a similar logic, the insulin resistance resulting from abnormal splicing of insulin receptor is also likely to be reversible (Savkur R S, et al. Nat Genet 2001; 29(1):40-47). It is understood herein that by correcting spliceopathy associated with DM1, the disease can be treated. For example, by inhibiting the interaction of MBNL1 with poly (CUG)$^{exp}$, MBNL1 is free to resume its effect on alternatively sliced transcripts, or by inhibiting sequestration of other CUG interacting protein, their normal functions can be restored. One method of inhibiting the interaction of MBNL1 with poly(CUG)$^{exp}$ is by displacing bound MBNL1 with another molecule.

B. METHODS OF SCREENING

Disclosed herein are methods of screening for an agent that inhibits the interaction of a protein and a ligand comprising the steps of a) capturing the ligand to a substrate; b) admixing a labeled protein with the ligand; c) contacting an agent with the mixture of step b; d) determining the level of the label; and e) comparing the amount of the label relative to a control; wherein a decrease in the level of the label indicates an agent that inhibits the interaction. Thus for example, disclosed herein are methods It is understood that the proteins of the method can be any polyCUG or polyCCUG interacting protein or a protein that is sequestered by polyCUG or polyCCUG repeats. Examples of the protein of the method are members of the Muscleblind family of RNA binding proteins which include MBNL1, MBNL2, and MBNL3. Mucleblind proteins play a significant role in the regulation of alternative splicing. During the DM1 disease process MBNL proteins are sequestered in the ribonuclear foci through interaction with polyCUG$^{exp}$ or polyC-CUG$^{exp}$ RNA leading to a disregulation of alternative splicing function "Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The methods disclosed herein refer to a ligand bound to a substrate. It is understood that "ligand" can refer to any protein, polypeptide, peptide, amino acid, or nucleotide chain (including, for example, all forms of DNA and RNA) capable of being bound by a protein. Thus, for example, disclosed herein are ligands wherein the ligand is polyCUG or polyC-CUG repeat RNA. Therefore, disclosed herein are methods of screening for an agent that inhibits the interaction of a protein and a ligand comprising the steps of a) capturing the ligand to a substrate; b) admixing a labeled protein with the ligand; c) contacting an agent with the mixture of step b; d) determining the level of the label; and e) comparing the amount of the label relative to a control; wherein a decrease in the level of the label indicates an agent that inhibits the interaction; and wherein the ligand is polyCUG mRNA or polyCCUG repeat RNA.

It is also understood that those of skill in the art will recognize that the assay will not lose effectiveness by reversing the order of the protein-ligand interaction. Thus, those of skill in the art will recognize that a method comprising a bound protein and labeled ligand will also be effective. Therefore, disclosed herein are methods of screening for an agent that inhibits the interaction of a protein and a ligand comprising the steps of a) mixing a protein bound to a substrate with a labeled ligand; b) contacting an agent with the mixture of step a; c) determining the level of the label; and d) comparing the amount of the label relative to a control; wherein a decrease in the level of the label indicates an agent that inhibits the interaction. Similarly it is understood that contacting the agent with the protein or ligand of the method before mixing the protein and ligand will also be effective. Thus, disclosed herein are A method in which agent is contacted with ligand or protein prior to step a, in order to prevent the interaction, will also be effective. Therefore disclosed herein are methods of screening for an agent that inhibits the interaction of a protein and a ligand comprising the steps of a) contacting an agent with the protein or labeled ligand; b) admixing the protein with labeled ligand; c) determining the level of the label; and d) comparing the amount of the label relative to a control; wherein a decrease in the level of the label bound to protein indicates an agent that inhibits the interaction.

Substrate refers to a solid support structure to which a molecule can be bound. The substrate can include any solid material. This includes materials such as acrylamide, agarose, cellulose, nitrocellulose, glass, gold, polystyrene, polyethylene vinyl acetate, polypropylene, polymethacrylate, polyethylene, polyethylene oxide, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Substrates can have any useful form including thin film, membrane, bottles, dishes, fibers, gels, woven fibers, shaped polymers, particles, beads, microparticles, or a combination. Substrates can be porous or non-porous. A chip is a rectangular or square small piece of material. Useful forms for substrates are sheets, films, and chips. A useful form for a substrate is a microtiter dish. Such dish can be, for example, a polystyrene dish or a polystyrene dish with nitrocellulose bottoms.

It is contemplated that any method known to the art can be used to bind the ligand or protein of the method to the substrate. Such binding can occur directly, for example, by contacting the protein to a substrate or indirectly through the use of GST or like molecules. Additionally, binding to the substrate can occur via a multiple binding reactions. For example, a substrate may be coated with streptavidin to which a biotinylated ligand, protein, or intermediary oligonucleotide may be bound. When a biotinylated oligonucleotide is bound to streptavidin, a complementary ligand can bind to the oligonucleotide. For example, an intermediary oligonucleotide can comprise biotinylated oligodeoxynucleotide (ODN). Alternatively, the ligand can be flanked by an RNA sequence from the DMPK gene or other sequence that permits capture to a substrate.

The disclosed methods can utilize any means of detecting a labeled moiety known in the art. Herein, a "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA or ELISPOT), biotin, digoxigenin, or haptens and proteins which can be made detectable, e.g., by incorporating a radiolabel into the peptide or used to detect antibodies specifically reactive with the peptide. Thus, for example the method of detection can comprise, for example, anisotropy.

As used herein, a label can include a fluorescent dye, a member of a binding pair, such as biotin/streptavidin, a metal (e.g., gold), or an epitope tag that can specifically interact with a molecule that can be detected, such as by producing a colored substrate or fluorescence. Substances suitable for detectably labeling proteins include fluorescent dyes (also known herein as fluorochromes and fluorophores) and enzymes that react with colorometric substrates (e.g., horseradish peroxidase). The use of fluorescent dyes is generally preferred in the practice of the invention as they can be detected at very low amounts. Furthermore, in the case where multiple antigens are reacted with a single array, each antigen can be labeled with a distinct fluorescent compound for simultaneous detection. Labeled spots on the array are detected using a fluorimeter, the presence of a signal indicating an antigen bound to a specific antibody.

Fluorophores are compounds or molecules that luminesce. Typically fluorophores absorb electromagnetic energy at one wavelength and emit electromagnetic energy at a second wavelength. Examples of fluorophores include, but are not limited to, 1,5 IAEDANS; 1,8-ANS; 4-Methylumbelliferone; 5-carboxy-2,7-dichlorofluorescein; 5-Carboxyfluorescein (5-FAM); 5-Carboxynapthofluorescein; 5-Carboxytetramethylrhodamine (5-TAMRA); 5-Hydroxy Tryptamine (5-HAT); 5-ROX (carboxy-X-rhodamine); 6-Carboxyrhodamine 6G; 6-CR 6G; 6-JOE; 7-Amino-4-methylcoumarin; 7-Aminoactinomycin D (7-AAD); 7-Hydroxy-4-I methylcoumarin; 9-Amino-6-chloro-2-methoxyacridine (ACMA); ABQ; Acid Fuchsin; Acridine Orange; Acridine Red; Acridine Yellow; Acriflavin; Acriflavin Feulgen SITSA; Aequorin (Photoprotein); AFPs—AutoFluorescent Protein—(Quantum Biotechnologies) see sgGFP, sgBFP; Alexa Fluor 350™; Alexa Fluor 430™; Alexa Fluor 488™; Alexa Fluor 532™; Alexa Fluor 546™; Alexa Fluor 568™; Alexa Fluor 594™; Alexa Fluor 633™; Alexa Fluor 647™; Alexa Fluor 660™; Alexa Fluor 680™; Alizarin Complexon; Alizarin Red; Allophycocyanin (APC); AMC, AMCA-S; Aminomethylcoumarin (AMCA); AMCA-X; Aminoactinomycin D; Aminocoumarin; Anilin Blue; Anthrocyl stearate; APC-Cy7; APTRA-BTC; APTS; Astrazon Brilliant Red 4G; Astrazon Orange R; Astrazon Red 6B; Astrazon Yellow 7 GLL; Atabrine; ATTO-TAG™ CBQCA; ATTO-TAG™ FQ; Auramine; Aurophosphine G; Aurophosphine; BAO 9 (Bisaminophenyloxadiazole); BCECF (high pH); BCECF (low pH); Berberine Sulphate; Beta Lactamase; BFP blue shifted GFP (Y66H); Blue Fluorescent Protein; BFP/GFP FRET; Bimane; Bisbenzemide; Bisbenzimide (Hoechst); bis-BTC; Blancophor FFG; Blancophor SV; BOBO™-1; BOBO™-3; Bodipy492/515; Bodipy493/503; Bodipy500/510; Bodipy; 505/515; Bodipy 530/550; Bodipy 542/563; Bodipy 558/568; Bodipy 564/570; Bodipy 576/589; Bodipy 581/591; Bodipy 630/650-X; Bodipy 650/665-X; Bodipy 665/676; Bodipy Fl; Bodipy FL ATP; Bodipy Fl-Ceramide; Bodipy R6G SE; Bodipy TMR; Bodipy TMR-X conjugate; Bodipy TMR-X, SE; Bodipy TR; Bodipy TR ATP; Bodipy TR-X SE; BO-PRO™-1; BO-PRO™-3; Brilliant Sulphoflavin FF; BTC; BTC-5N; Calcein; Calcein Blue; Calcium Crimson-; Calcium Green; Calcium Green-1 $Ca^{2+}$ Dye; Calcium Green-2 $Ca^{2+}$; Calcium Green-5N $Ca^{2+}$; Calcium Green-C18 $Ca^{2+}$; Calcium Orange; Calcofluor White; Carboxy-X-rhodamine (5-ROX); Cascade Blue™; Cascade Yellow; Catecholamine; CCF2 (GeneBlazer); CFDA; CFP (Cyan Fluorescent Protein); CFP/YFP FRET; Chlorophyll; Chromomycin A; Chromomycin A; CL-NERF; CMFDA; Coelenterazine; Coelenterazine cp; Coelenterazine f; Coelenterazine fcp; Coelenterazine h; Coelenterazine hcp; Coelenterazine ip; Coelenterazine n; Coelenterazine O; Coumarin Phalloidin; C-phycocyanine; CPM I Methylcoumarin; CTC; CTC Formazan; Cy2™; Cy3.1 8; Cy3.5™; Cy3™; Cy5.1 8; Cy5.5™; Cy5™; Cy7™; Cyan GFP; cyclic AMP Fluorosensor (FiCRhR); Dabcyl; Dansyl; Dansyl Amine; Dansyl Cadaverine; Dansyl Chloride; Dansyl DHPE; Dansyl fluoride; DAPI; Dapoxyl; Dapoxyl 2; Dapoxyl 3'DCFDA; DCFH (Dichlorodihydrofluorescein Diacetate); DDAO; DHR (Dihydrorhodamine 123); Di-4-ANEPPS; Di-8-ANEPPS (non-ratio); DiA (4-Di 16-ASP); Dichlorodihydrofluorescein Diacetate (DCFH); DiD-Lipophilic Tracer; DiD (DilC18(5)); DIDS; Dihydrorhodamine 123 (DHR); Dil (DilC18(3)); I Dinitrophenol; DiO (DiOC18(3)); DiR; DiR (DilC18(7)); DM-NERF (high pH); DNP; Dopamine; DsRed; DTAF; DY-630-NHS; DY-635-NHS; EBFP; ECFP; EGFP; ELF 97; Eosin; Erythrosin; Erythrosin ITC; Ethidium Bromide; Ethidium homodimer-1 (EthD-1); Euchrysin; EukoLight; Europium (111) chloride; EYFP; Fast Blue; FDA; Feulgen (Pararosaniline); FIF (Formaldehyd Induced Fluorescence); fluorescein isothiocyanate (FITC); Flazo Orange; Fluo-3; Fluo-4; Fluorescein (FITC); Fluorescein Diacetate; Fluoro-Emerald; Fluoro-Gold (Hydroxystilbamidine); Fluor-Ruby; Fluor X; FM 1-43™; FM 4-46; Fura Red™ (high pH); Fura Red™/Fluo-3; Fura-2; Fura-2/BCECF; Genacryl Brilliant Red B; Genacryl Brilliant Yellow 10GF; Genacryl Pink 3G; Genacryl Yellow 5GF; GeneBlazer; (CCF2); GFP (S65T); GFP red shifted (rsGFP); GFP wild type' non-UV excitation (wtGFP); GFP wild type, UV excitation (wtGFP); GFPuv; Gloxalic Acid; Granular blue; Haematoporphyrin; Hoechst 33258; Hoechst 33342; Hoechst 34580; HPTS; Hydroxycoumarin; Hydroxystilbamidine (FluoroGold); Hydroxytryptamine; Indo-1, high calcium; Indo-1 low calcium; Indodicarbocyanine (DiD); Indotricarbocyanine (DiR); Intrawhite Cf; JC-1; JO JO-1; JO-PRO-1; LaserPro; Laurodan; LDS 751 (DNA); LDS 751 (RNA); Leucophor PAF; Leucophor SF; Leucophor WS; Lissamine Rhodamine; Lissamine Rhodamine B; Calcein/Ethidium homodimer; LOLO-1; LO-PRO-1; Lucifer Yellow; Lyso Tracker Blue; Lyso Tracker Blue-White; Lyso Tracker Green; Lyso Tracker Red; Lyso Tracker Yellow; LysoSensor Blue; LysoSensor Green; LysoSensor Yellow/Blue; Mag Green; Magdala Red (Phloxin B); Mag-Fura Red; Mag-Fura-2; Mag-Fura-5; Mag-Indo-1; Magnesium Green; Magnesium Orange; Malachite Green; Marina Blue; I Maxilon Brilliant Flavin 10 GFF; Maxilon Brilliant Flavin 8 GFF; Merocyanin; Methoxycoumarin; Mitotracker Green FM; Mitotracker Orange; Mitotracker Red; Mitramycin; Monobromobimane; Monobromobimane (mBBr-GSH); Monochlorobimane; MPS (Methyl Green Pyronine Stilbene); NBD; NBD Amine; Nile Red; Nitrobenzoxedidole; Noradrenaline; Nuclear Fast Red; i Nuclear Yellow; Nylosan Brilliant lavin E8G; Oregon Green™; Oregon Green™ 488; Oregon Green™ 500; Oregon Green™ 514; Pacific Blue; Pararosaniline (Feulgen); PBFI; PE-Cy5; PE-Cy7; PerCP; PerCP-Cy5.5; PE-TexasRed (Red 613); Phloxin B (Magdala Red); Phorwite AR; Phorwite BKL; Phorwite Rev; Phorwite RPA; Phosphine 3R; Photo-Resist; Phycoerythrin B [PE]; Phycoerythrin R [PE]; PKH26 (Sigma); PKH67; PMIA; Pontochrome Blue Black; POPO-1; POPO-3; PO-PRO-1; PO-I PRO-3; Primuline; Procion Yellow; Propidium Iodid (Pl); PyMPO; Pyrene; Pyronine; Pyronine B; Pyrozal Brilliant Flavin 7GF; QSY 7; Quinacrine Mustard; Resorufin; RH 414; Rhod-2; Rhodamine; Rhodamine 110; Rhodamine 123; Rhodamine 5 GLD; Rhodamine 6G; Rhodamine B; Rhodamine B 200; Rhodamine B extra; Rhodamine BB; Rhodamine BG; Rhodamine Green; Rhodamine Phallicidine; Rhodamine: Phalloidine; Rhodamine Red; Rhodamine WT; Rose Bengal; R-phycocyanine; R-phycoerythrin (PE); rsGFP; S65A; S65C; S65L; S65T; Sapphire GFP; SBFI; Serotonin; Sevron Brilliant Red 2B; Sevron Brilliant Red 4G; Sevron I Brilliant Red B; Sevron Orange; Sevron Yellow L; sgBFP™ (super glow BFP); sgGFP™ (super glow GFP); SITS (Primuline; Stilbene Isothiosulphonic Acid); SNAFL calcein; SNAFL-1; SNAFL-2; SNARF calcein; SNARF1; Sodium Green; SpectrumAqua; SpectrumGreen; SpectrumOrange; Spectrum Red; SPQ (6-methoxy-N-(3 sulfopropyl) quinolinium); Stilbene; Sulphorhodamine B and C; Sulphorhodamine Extra; SYTO 11; SYTO 12; SYTO 13; SYTO 14; SYTO 15; SYTO 16; SYTO 17; SYTO 18; SYTO 20; SYTO 21; SYTO 22; SYTO 23; SYTO 24; SYTO 25; SYTO 40; SYTO 41; SYTO 42; SYTO 43; SYTO 44; SYTO 45; SYTO 59; SYTO 60; SYTO 61; SYTO 62; SYTO 63; SYTO 64; SYTO 80; SYTO 81; SYTO 82; SYTO 83; SYTO 84; SYTO 85; SYTOX Blue; SYTOX Green; SYTOX Orange; Tetracycline; Tetramethylrhodamine (TRITC); Texas Red™; Texas Red-X™ conjugate; Thiadicarbocyanine (DiSC3); Thiazine Red R; Thiazole Orange; Thioflavin 5; Thioflavin S; Thioflavin TON; Thiolyte; Thiozole Orange; Tinopol CBS (Calcofluor White); TIER; TO-PRO-1; TO-PRO-3; TO-PRO-5; TOTO-1; TOTO-3; TriColor (PE-Cy5); TRITC TetramethylRodamineIsoThioCyanate; True Blue; Tru Red; Ultralite; Uranine B; Uvitex SFC; wt GFP; WW 781; X-Rhodamine; XRITC; Xylene Orange; Y66F; Y66H; Y66W; Yellow GFP; YFP; YO-PRO-1; YO-PRO 3; YOYO-1; YOYO-3; Sybr Green; Thiazole orange (interchelating dyes); semiconductor nanoparticles such as quantum dots; or caged fluorophore (which can be activated with light or other electromagnetic energy source), or a combination thereof.

A modifier unit such as a radionuclide can be incorporated into or attached directly to any of the compounds described herein by halogenation. Examples of radionuclides useful in this embodiment include, but are not limited to, tritium, iodine-125, iodine-131, iodine-123, iodine-124, astatine-210, carbon-11, carbon-14, nitrogen-13, fluorine-18. In another aspect, the radionuclide can be attached to a linking group or bound by a chelating group, which is then attached to the compound directly or by means of a linker. Examples of radionuclides useful in this aspect include, but are not limited to, Tc-99m, Re-186, Ga-68, Re-188, Y-90, Sm-153, Bi-212, Cu-67, Cu-64, and Cu-62. Radiolabeling techniques such as these are routine in the radiopharmaceutical industry.

The radiolabeled compounds are useful as imaging agents to diagnose neurological disease (e.g., a neurodegenerative disease) or a mental condition or to follow the progression or treatment of such a disease or condition in a mammal (e.g., a human). The radiolabeled compounds described herein can be conveniently used in conjunction with imaging techniques such as positron emission tomography (PET) or single photon emission computerized tomography (SPECT).

Labeling can be either direct or indirect. In direct labeling, the detecting antibody (the antibody for the molecule of interest) or detecting molecule (the molecule that can be bound by an antibody to the molecule of interest) include a label. Detection of the label indicates the presence of the detecting antibody or detecting molecule, which in turn indicates the presence of the molecule of interest or of an antibody to the molecule of interest, respectively. In indirect labeling, an additional molecule or moiety is brought into contact with, or generated at the site of, the immunocomplex. For example, a signal-generating molecule or moiety such as an enzyme can be attached to or associated with the detecting antibody or detecting molecule. The signal-generating molecule can then generate a detectable signal at the site of the immunocomplex. For example, an enzyme, when supplied with suitable substrate, can produce a visible or detectable product at the site of the immunocomplex. ELISAs use this type of indirect labeling.

As another example of indirect labeling, an additional molecule (which can be referred to as a binding agent) that can bind to either the molecule of interest or to the antibody (primary antibody) to the molecule of interest, such as a second antibody to the primary antibody, can be contacted with the immunocomplex. The additional molecule can have a label or signal-generating molecule or moiety. The additional molecule can be an antibody, which can thus be termed a secondary antibody. Binding of a secondary antibody to the primary antibody can form a so-called sandwich with the first (or primary) antibody and the molecule of interest. The immune complexes can be contacted with the labeled, secondary antibody under conditions effective and for a period of time sufficient to allow the formation of secondary immune complexes. The secondary immune complexes can then be generally washed to remove any non-specifically bound labeled secondary antibodies, and the remaining label in the secondary immune complexes can then be detected. The additional molecule can also be or include one of a pair of molecules or moieties that can bind to each other, such as the biotin/avadin pair. In this mode, the detecting antibody or detecting molecule should include the other member of the pair.

Other modes of indirect labeling include the detection of primary immune complexes by a two step approach. For example, a molecule (which can be referred to as a first binding agent), such as an antibody, that has binding affinity for the molecule of interest or corresponding antibody can be used to form secondary immune complexes, as described above. After washing, the secondary immune complexes can be contacted with another molecule (which can be referred to as a second binding agent) that has binding affinity for the first binding agent, again under conditions effective and for a period of time sufficient to allow the formation of immune complexes (thus forming tertiary immune complexes). The second binding agent can be linked to a detectable label or signal-generating molecule or moiety, allowing detection of the tertiary immune complexes thus formed. This system can provide for signal amplification.

Immunoassays that involve the detection of as substance, such as a protein or an antibody to a specific protein, include label-free assays, protein separation methods (i.e., electrophoresis), solid support capture assays, or in vivo detection. Label-free assays are generally diagnostic means of determining the presence or absence of a specific protein, or an antibody to a specific protein, in a sample. Protein separation methods are additionally useful for evaluating physical properties of the protein, such as size or net charge. Capture assays are generally more useful for quantitatively evaluating the concentration of a specific protein, or antibody to a specific protein, in a sample. Finally, in vivo detection is useful for evaluating the spatial expression patterns of the substance, i.e., where the substance can be found in a subject, tissue or cell.

Provided that the concentrations are sufficient, the molecular complexes ([Ab-Ag]n) generated by antibody-antigen interaction are visible to the naked eye, but smaller amounts may also be detected and measured due to their ability to scatter a beam of light. The formation of complexes indicates that both reactants are present, and in immunoprecipitation assays a constant concentration of a reagent antibody is used to measure specific antigen ([Ab-Ag]n), and reagent antigens are used to detect specific antibody ([Ab-Ag]n). If the reagent species is previously coated onto cells (as in hemagglutination assay) or very small particles (as in latex agglutination assay), "clumping" of the coated particles is visible at much lower concentrations. A variety of assays based on these elementary principles are in common use, including Ouchterlony immunodiffusion assay, rocket immunoelectrophoresis, and immunoturbidometric and nephelometric assays. The main limitations of such assays are restricted sensitivity (lower detection limits) in comparison to assays employing labels and, in some cases, the fact that very high concentrations of analyte can actually inhibit complex formation, necessitating safeguards that make the procedures more complex. Some of these Group 1 assays date right back to the discovery of antibodies and none of them have an actual "label" (e.g. Ag-enz). Other kinds of immunoassays that are label free depend on immunosensors, and a variety of instruments that can directly detect antibody-antigen interactions are now commercially available. Most depend on generating an evanescent wave on a sensor surface with immobilized ligand, which allows continuous monitoring of binding to the ligand. Immunosensors allow the easy investigation of kinetic interactions and, with the advent of lower-cost specialized instruments, may in the future find wide application in immunoanalysis.

The use of immunoassays to detect a specific protein can involve the separation of the proteins by electophoresis. Electrophoresis is the migration of charged molecules in solution in response to an electric field. Their rate of migration depends on the strength of the field; on the net charge, size and shape of the molecules and also on the ionic strength, viscosity and temperature of the medium in which the molecules are moving. As an analytical tool, electrophoresis is simple, rapid and highly sensitive. It is used analytically to study the properties of a single charged species, and as a separation technique.

Generally the sample is run in a support matrix such as paper, cellulose acetate, starch gel, agarose or polyacrylamide gel. The matrix inhibits convective mixing caused by heating and provides a record of the electrophoretic run: at the end of the run, the matrix can be stained and used for scanning, autoradiography or storage. In addition, the most commonly used support matrices—agarose and polyacrylamide—provide a means of separating molecules by size, in that they are porous gels. A porous gel may act as a sieve by retarding, or in some cases completely obstructing, the movement of large macromolecules while allowing smaller molecules to migrate freely. Because dilute agarose gels are generally more rigid and easy to handle than polyacrylamide of the same concentration, agarose is used to separate larger macromolecules such as nucleic acids, large proteins and protein complexes. Polyacrylamide, which is easy to handle and to make at higher concentrations, is used to separate most proteins and small oligonucleotides that require a small gel pore size for retardation.

Proteins are amphoteric compounds; their net charge therefore is determined by the pH of the medium in which they are suspended. In a solution with a pH above its isoelectric point, a protein has a net negative charge and migrates towards the anode in an electrical field. Below its isoelectric point, the protein is positively charged and migrates towards the cathode. The net charge carried by a protein is in addition independent of its size—i.e., the charge carried per unit mass (or length, given proteins and nucleic acids are linear macromolecules) of molecule differs from protein to protein. At a given pH therefore, and under non-denaturing conditions, the electrophoretic separation of proteins is determined by both size and charge of the molecules.

Sodium dodecyl sulphate (SDS) is an anionic detergent which denatures proteins by "wrapping around" the polypeptide backbone—and SDS binds to proteins fairly specifically in a mass ratio of 1.4:1. In so doing, SDS confers a negative charge to the polypeptide in proportion to its length. Further, it is usually necessary to reduce disulphide bridges in proteins (denature) before they adopt the random-coil configuration necessary for separation by size; this is done with 2-mercaptoethanol or dithiothreitol (DTT). In denaturing SDS-PAGE separations therefore, migration is determined not by intrinsic electrical charge of the polypeptide, but by molecular weight.

Determination of molecular weight is done by SDS-PAGE of proteins of known molecular weight along with the protein to be characterized. A linear relationship exists between the logarithm of the molecular weight of an SDS-denatured polypeptide, or native nucleic acid, and its Rf. The Rf is calculated as the ratio of the distance migrated by the molecule to that migrated by a marker dye-front. A simple way of determining relative molecular weight by electrophoresis (Mr) is to plot a standard curve of distance migrated vs. log 10MW for known samples, and read off the log Mr of the sample after measuring distance migrated on the same gel.

In two-dimensional electrophoresis, proteins are fractionated first on the basis of one physical property, and, in a second step, on the basis of another. For example, isoelectric focusing can be used for the first dimension, conveniently carried out in a tube gel, and SDS electrophoresis in a slab gel can be used for the second dimension. One example of a procedure is that of O'Farrell, P. H., High Resolution Two-dimensional Electrophoresis of Proteins, J. Biol. Chem. 250: 4007-4021 (1975), herein incorporated by reference in its entirety for its teaching regarding two-dimensional electrophoresis methods. Other examples include but are not limited to, those found in Anderson, L and Anderson, N G, High resolution two-dimensional electrophoresis of human plasma proteins, Proc. Natl. Acad. Sci. 74:5421-5425 (1977), Ornstein, L., Disc electrophoresis, L. Ann. N.Y. Acad. Sci. 121: 321349 (1964), each of which is herein incorporated by reference in its entirety for teachings regarding electrophoresis methods.

Laemmli, U. K., Cleavage of structural proteins during the assembly of the head of bacteriophage T4, Nature 227:680 (1970), which is herein incorporated by reference in its entirety for teachings regarding electrophoresis methods, discloses a discontinuous system for resolving proteins denatured with SDS. The leading ion in the Laemmli buffer system is chloride, and the trailing ion is glycine. Accordingly, the resolving gel and the stacking gel are made up in Tris-HCl buffers (of different concentration and pH), while the tank buffer is Tris-glycine. All buffers contain 0.1% SDS.

One example of an immunoassay that uses electrophoresis that is contemplated in the current methods is Western blot analysis. Western blotting or immunoblotting allows the determination of the molecular mass of a protein and the measurement of relative amounts of the protein present in different samples. Detection methods include chemiluminescence and chromagenic detection. Standard methods for Western blot analysis can be found in, for example, D. M. Bollag et al., Protein Methods (2d edition 1996) and E. Harlow & D. Lane, Antibodies, a Laboratory Manual (1988), U.S. Pat. No. 4,452,901, each of which is herein incorporated by reference in their entirety for teachings regarding Western blot methods. Generally, proteins are separated by gel electrophoresis, usually SDS-PAGE. The proteins are transferred to a sheet of special blotting paper, e.g., nitrocellulose, though other types of paper or membranes, can be used. The proteins retain the same pattern of separation as on the gel. The blot is incubated with a generic protein (such as milk proteins) to bind to any remaining sticky places on the nitrocellulose. An antibody is then added to the solution which is able to bind to its specific protein.

The attachment of specific antibodies to specific immobilized antigens can be readily visualized by indirect enzyme immunoassay techniques, usually using a chromogenic substrate (e.g. alkaline phosphatase or horseradish peroxidase) or chemiluminescent substrates. Other possibilities for probing include the use of fluorescent or radioisotope labels (e.g., fluorescein, $^{125}$I). Probes for the detection of antibody binding can be conjugated anti-immunoglobulins, conjugated staphylococcal Protein A (binds IgG), or probes to biotinylated primary antibodies (e.g., conjugated avidin/streptavidin).

The power of the technique lies in the simultaneous detection of a specific protein by means of its antigenicity, and its molecular mass. Proteins are first separated by mass in the SDS-PAGE, then specifically detected in the immunoassay step. Thus, protein standards (ladders) can be run simultaneously in order to approximate molecular mass of the protein of interest in a heterogeneous sample.

The gel shift assay or electrophoretic mobility shift assay (EMSA) can be used to detect the interactions between DNA binding proteins and their cognate DNA recognition sequences, in both a qualitative and quantitative manner. Exemplary techniques are described in Ornstein L., Disc electrophoresis—I: Background and theory, Ann. NY Acad. Sci. 121:321-349 (1964), and Matsudiara, P T and D R Burgess, SDS microslab linear gradient polyacrylamide gel electrophoresis, Anal. Biochem. 87:386-396 (1987), each of which is herein incorporated by reference in its entirety for teachings regarding gel-shift assays.

In a general gel-shift assay, purified proteins or crude cell extracts can be incubated with a labeled (e.g., $^{32}$P-radiolabeled) DNA or RNA probe, followed by separation of the complexes from the free probe through a nondenaturing polyacrylamide gel. The complexes migrate more slowly through the gel than unbound probe. Depending on the activity of the binding protein, a labeled probe can be either double-stranded or single-stranded. For the detection of DNA binding proteins such as transcription factors, either purified or partially purified proteins, or nuclear cell extracts can be used. For detection of RNA binding proteins, either purified or partially purified proteins, or nuclear or cytoplasmic cell extracts can be used. The specificity of the DNA or RNA binding protein for the putative binding site is established by competition experiments using DNA or RNA fragments or oligonucleotides containing a binding site for the protein of interest, or other unrelated sequence. The differences in the nature and intensity of the complex formed in the presence of specific and nonspecific competitor allows identification of specific interactions. Refer to Promega, Gel Shift Assay FAQ, available at <http://www.promega.com/faq/gelshfaq.html> (last visited Mar. 25, 2005), which is herein incorporated by reference in its entirety for teachings regarding gel shift methods.

Gel shift methods can include using, for example, colloidal forms of COOMASSIE (Imperial Chemicals Industries, Ltd) blue stain to detect proteins in gels such as polyacrylamide electrophoresis gels. Such methods are described, for example, in Neuhoff et al., Electrophoresis 6:427-448 (1985), and Neuhoff et al., Electrophoresis 9:255-262 (1988), each of which is herein incorporated by reference in its entirety for teachings regarding gel shift methods. In addition to the conventional protein assay methods referenced above, a combination cleaning and protein staining composition is described in U.S. Pat. No. 5,424,000, herein incorporated by reference in its entirety for its teaching regarding gel shift methods. The solutions can include phosphoric, sulfuric, and nitric acids, and Acid Violet dye.

Radioimmune Precipitation Assay (RIPA) is a sensitive assay using radiolabeled antigens to detect specific antibodies in serum. The antigens are allowed to react with the serum and then precipitated using a special reagent such as, for example, protein A sepharose beads. The bound radiolabeled immunoprecipitate is then commonly analyzed by gel electrophoresis. Radioimmunoprecipitation assay (RIPA) is often used as a confirmatory test for diagnosing the presence of HIV antibodies. RIPA is also referred to in the art as Farr Assay, Precipitin Assay, Radioimmune Precipitin Assay; Radioimmunoprecipitation Analysis; Radioimmunoprecipitation Analysis, and Radioimmunoprecipitation Analysis.

While the above immunoassays that utilize electrophoresis to separate and detect the specific proteins of interest allow for evaluation of protein size, they are not very sensitive for evaluating protein concentration. However, also contemplated are immunoassays wherein the protein or antibody specific for the protein is bound to a solid support (e.g., tube, well, bead, or cell) to capture the antibody or protein of interest, respectively, from a sample, combined with a method of detecting the protein or antibody specific for the protein on the support. Examples of such immunoassays include Radioimmunoassay (RIA), Enzyme-Linked Immunosorbent Assay (ELISA), Flow cytometry, protein array, multiplexed bead assay, and magnetic capture.

Radioimmunoassay (RIA) is a classic quantitative assay for detection of antigen-antibody reactions using a radioactively labeled substance (radioligand), either directly or indirectly, to measure the binding of the unlabeled substance to a specific antibody or other receptor system. Radioimmunoassay is used, for example, to test hormone levels in the blood without the need to use a bioassay. Non-immunogenic substances (e.g., haptens) can also be measured if coupled to larger carrier proteins (e.g., bovine gamma-globulin or human serum albumin) capable of inducing antibody formation. RIA involves mixing a radioactive antigen (because of the ease with which iodine atoms can be introduced into tyrosine residues in a protein, the radioactive isotopes $^{125}$I or $^{131}$I are often used) with antibody to that antigen. The antibody is generally linked to a solid support, such as a tube or beads. Unlabeled or "cold" antigen is then adding in known quantities and measuring the amount of labeled antigen displaced. Initially, the radioactive antigen is bound to the antibodies. When cold antigen is added, the two compete for antibody binding sites and at higher concentrations of cold antigen, more binds to the antibody, displacing the radioactive variant. The bound antigens are separated from the unbound ones in solution and the radioactivity of each used to plot a binding curve.

Enzyme-Linked Immunosorbent Assay (ELISA), or more generically termed EIA (Enzyme ImmunoAssay), is an immunoassay that can detect an antibody specific for a protein. In such an assay, a detectable label bound to either an antibody-binding or antigen-binding reagent is an enzyme. When exposed to its substrate, this enzyme reacts in such a manner as to produce a chemical moiety which can be detected, for example, by spectrophotometric, fluorometric or visual means. Enzymes which can be used to detectably label reagents useful for detection include, but are not limited to, horseradish peroxidase, alkaline phosphatase, glucose oxidase, β-galactosidase, ribonuclease, urease, catalase, malate dehydrogenase, staphylococcal nuclease, asparaginase, yeast alcohol dehydrogenase, alpha.-glycerophosphate dehydrogenase, triose phosphate isomerase, glucose-6-phosphate dehydrogenase, glucoamylase and acetylcholinesterase. For descriptions of ELISA procedures, see Voller, A. et al., J. Clin. Pathol. 31:507-520 (1978); Butler, J. E., Meth. Enzymol. 73:482-523 (1981); Maggio, E. (ed.), Enzyme Immunoassay, CRC Press, Boca Raton, 1980; Butler, J. E., In: Structure of Antigens, Vol. 1 (Van Regenmortel, M., CRC Press, Boca Raton, 1992, pp. 209-259; Butler, J. E., In: van Oss, C. J. et al., (eds), Immunochemistry, Marcel Dekker, Inc., New York, 1994, pp. 759-803; Butler, J. E. (ed.), Immunochemistry of Solid-Phase Immunoassay, CRC Press, Boca Raton, 1991); Crowther, "ELISA: Theory and Practice," In: Methods in Molecule Biology, Vol. 42, Humana Press; New Jersey, 1995; U.S. Pat. No. 4,376,110, each of which is incorporated herein by reference in its entirety and specifically for teachings regarding ELISA methods.

It is understood that any instrument that is capable of detecting the labels used herein is appropriate for the methods disclosed. Additional means of detection can also be used such as reporter constructs such as the luciferase gene as well as methods of label complementation. In short, any means known in the art for detection of acceptable for use with the disclosed methods.

Disclosed herein are cells comprising the first protein, a second protein, and a nucleic acid comprising the first recognition element adjacent to a second recognition element, wherein the first protein binds the first recognition element and the second protein binds the second recognition element, wherein at least one of the first and second proteins comprises a first half of a split fluorescent protein and at least one of the first and second proteins comprises a second half of the split fluorescent protein, wherein binding of the first and second proteins to their respective recognition sites results in the assembly and excitation of the split fluorescent protein. It is understood that the disclosed cells can be used to screen for agents that inhibits the interaction of a first protein and a first recognition element on a nucleic acid comprising the steps of a) administering an agent to a cell comprising the first protein, a second protein, and a nucleic acid comprising the first recognition element adjacent to a second recognition element, wherein the first protein binds the first recognition element and the second protein binds the second recognition element; and b) detecting co-localization of the first and second protein, wherein a decrease in co-localization of the first and second protein relative to a control indicates an agent that inhibits the interaction. It is understood that in the methods disclosed herein, the first protein can comprise MBNL1, MBNL2, or MBNL3 and the first recognition element can comprise polyCUG or polyCCUG It is also understood that the second protein can comprise, for example, MS2 and the second recognition element can be an MS2 coat protein RNA recognition element. The interaction of the disclosed proteins can be used to facilitate a detection method not available when one or more components are not available. For example, disclosed herein are methods of screening for an agent, wherein at least one of the first and second proteins comprises a donor fluorescent dye and at least one of the first and second proteins comprises an acceptor dye, wherein excitation of the donor fluorescent dye results in a fluorescent emission that excites the acceptor dye if the first and second proteins are co-localized.

Thus, in one aspect, the acceptor dye fluoresces when excited and detection of this fluorescence is an indication of cleavage. Traditional examples of donor fluorescent dyes and acceptor fluorescent dyes include FAM and TAMRA. In another aspect, the acceptor dye quenches the fluorescence of the donor dye by absorbing the energy emitted by the fluorophore, releasing it as heat rather than fluorescence. In this aspect, the detection of fluorescence emitted from the donor dye is an indication of cleavage. Examples of dark quenchers are methyl red, DABCYL, ElleQuencher™, and Eclipse™ Dark Quencher. Methyl red quenches the lower wavelength dyes such as FAM but is not good at quenching those that emit at a higher wavelength, e.g. Cy5™. ElleQuencher™ was designed to quench the higher end of the spectrum. It has been tested in Double-Dye Oligonucleotide probes and Scorpions™. It gives good results for both when tested with dyes such as ROX and TAMRA but is also equivalent or better than methyl red for dyes such as FAM (lower wavelength).

Also disclosed are methods, wherein at least one of the first and second proteins comprises a first half of a split fluorescent protein and at least one of the first and second proteins comprises a second half of the split fluorescent protein, wherein excitation of the split fluorescent protein results in a fluorescent emission if the first and second proteins are co-localized. It is understood that one example of a split fluorescent protein that can be used in the disclosed methods is Venus fluorescent protein (VFP). It is understood that other methods of displaying co-localization in the cell. For example, the disclosed herein are methods wherein at least one of the first and second proteins comprises a first half of a split beta galactosidase protein and at least one of the first and second proteins comprises a second half of the split beta galactosidase protein, wherein hydrolysis of a beta galactosidase substrate results in fluorescence of luminescence if the first and second proteins are co-localized.

Also disclosed are method of screening for an agent that improves spliceopathy comprising the steps of a) introducing an agent into a cell comprising of a splicing regulator, overexpressed polyCUG or polyCCUG repeat RNA, and spliceopathy reporter construct, wherein the reporter construct comprises a gene susceptible to polyCUG or polyCCUG repeat induced spliceopathy flanked by one or more genes encoding a labeled protein; and b) measuring the level of the labeled protein; and c) comparing the ratio of labeled protein, wherein an increase of labeled protein indicates an agent that improves spliceopathy. For example, disclosed herein, are methods wherein the reporter proteins flanking the nucleic acid sequence of the spliceopathy reporter are labeled proteins. It is understood that examples of splicing regulators include but are not limited to MBNL1, MBNL2, MBNL3, CUG-B1, and ETR-3. It is also understood that examples of spliceopathy susceptible genes include but are not limited to TNNT3 and SERCA1. It is understood that such labeled proteins can be labeled similarly or have different labels. Thus, for example, disclosed are methods wherein the gene susceptible to polyCUG or polyCCUG is flanked by a gene encoding a single labeled protein, and wherein an increase of the labeled protein indicates an agent that improves spliceopathy. An example of such a label can be green fluorescence protein. Also, for example disclosed are methods wherein the gene susceptible to polyCUG or polyCCUG is flanked by genes encoding first and second labeled protein, wherein the first and second proteins are differentially labeled; and wherein the method further comprises d) comparing the ratio of the first labeled protein to the second labeled protein, wherein a high ratio indicates an agent that improves spliceopathy. Thus, for example, disclosed herein are methods wherein the first and second labeled proteins are labeled with YFP and Y•CFP respectively, and wherein an improvement of spliceopathy is determined by comparing the ration of YFP to Y•CFP, wherein a high ratio indicates the agent improved spliceopathy. Also disclosed are methods of screening for an agent that inhibits the interaction of a protein and a ligand comprising the steps of a) introducing an agent into a cell comprising an MBNL1 expression construct and an spliceopathy reporter construct susceptible to poly(CUG)$^{exp}$ induced spliceopathy, wherein the reporter construct comprises a polyCUG susceptible exon flanked by introns and exons encoding first and second labeled protein, wherein the first and second proteins are differentially labeled.

Alternatively, the disclosed methods can be achieved without the use of labeled proteins. For example, a minigene encoding luciferase reporter construct can be used. Thus, disclosed herein are methods of screening for an agent that improves spliceopathy comprising the steps of a) introducing an agent into a cell comprising a splicing regulator protein, a poly(CUG) or poly(CCUG) expanded RNA, and a spliceopathy reporter wherein the spliceopathy reporter comprises a nucleic acid sequence susceptible to splicing flanked by a reporter protein wherein the reporter protein is luciferase; and measuring the level of lucifierase activity.

1. Kits

Disclosed herein are kits that are drawn to reagents that can be used in practicing the methods disclosed herein. The kits can include any reagent or combination of reagent discussed herein or that would be understood to be required or beneficial in the practice of the disclosed methods. For example, the kits could include primers to perform the amplification reactions discussed in certain embodiments of the methods, as well as the buffers and enzymes required to use the primers as intended. For example, disclosed is a kit for screening for agents that inhibit the interaction of MBNL1 with polyCUG$^{exp}$ mRNA. It is understood that agents identified by the disclosed screening methods can be used to treat DM1. Thus, disclosed herein are kits for screening for agents that can be used to treat DM1. Thus, for example, disclosed are kits comprising a polystyrene plate, polyCUG$^{exp}$ mRNA, a capture oligodeoxynucleotide (ODN), and MBNL1, wherein the MBNL1 is labeled. Also disclosed are kits comprising a nitrocellulose filter plate, labeled polyCUG$^{exp}$ mRNA, and MBNL1. It is understood and herein contemplated that the proteins or polyCUG$^{exp}$ provided in the kits disclosed herein can be labeled by any means known in the art. For example, the label can be a fluorescent label such as fluoroscein isothiocyanate (FITC), phycoerythrin (PE), TEXAS RED®, Green fluorescent protein (GFP), yellow fluorescent protein (YFP), cyan fluorescent protein (CFP), allophycocyanin (APC), PerCP™, CY-CHROME™, or PharRED™. Alternatively, the label could be a radio label, or an enzymatic reporter such as beta galactosidase, horseradish peroxidase, or alkaline phosphatase.

2. Methods of Treatment

Disclosed herein are methods treating myotonic dystrophy (DM) in a subject in need thereof comprising administering to the subject an agent that inhibits the interaction of muscleblind proteins such as MBNL1, MBNL2, or MBNL3 with polyCUG$^{exp}$ mRNA. It is understood and herein contemplated that many different molecules can accomplish this task. For example, disclosed herein are methods of treating wherein the agent comprises a morpholino such as CAG25 (SEQ ID NO: 3) or the morpholino set forth in SEQ ID NO: 5. It is understood that the disclosed methods of treating myotonic dystrophy can be used to treat myotonic dystrophy type 1 (DM1) or myotonic dystrophy type 2 (DM2). Also disclosed are methods of treating myotonic dystrophy wherein the agent is an aminoglycosidic antibiotic compound such as, for example, neomycin and gentamicin. Further disclosed herein are methods treating myotonic dystrophy in a subject in need thereof comprising administering to the subject an agent that improves spliceopathy.

Spliceopathy refers to the abnormal regulation of alternative splicing. It is understood that such disregulation can result from the sequestration of splicing factors such as the muscleblind proteins. Thus, for example, disclosed herein are methods of treating DM1 in a subject in need thereof comprising administering to the subject an agent that improves spliceopathy. It is understood and herein contemplated that many different molecules can accomplish this task. For example, disclosed herein are methods of treating wherein the agent comprises a morpholino such as CAG25 (SEQ ID NO: 3) or the morpholino set forth in SEQ ID NOs: 3, 4, 5, 6. Also disclosed are methods of treating myotonic dystrophy wherein the agent is an aminoglycosidic antibiotic compound such as, for example, neomycin and gentamicin. Thus, for example, specifically disclosed are methods of treating myotonic dystrophy wherein the agent is an aminoglycosidic antibiotic compound such as, for example, neomycin and gentamicin. Also disclosed herein are methods of treating myotonic dystrophy type 2 (DM2) in a subject in need thereof comprising administering to the subject an agent that improves spliceopathy. Also disclosed herein are methods of treating myotonic dystrophy type 2 (DM2) in a subject in need thereof comprising administering to the subject an agent that improves spliceopathy. As with treatment for DM1, many different molecules can accomplish this task. For example, disclosed herein are methods of treating wherein the agent comprises a morpholino such as CAG25 (SEQ ID NO: 3) or aminoglycosidic antibiotic compound such as, for example, neomycin and gentamicin can be used as treatment.

It is further understood that the methods of treating DM can affect DM by inhibiting, improving, or reversing channelopathy. Channelopathy is the reduction in ion channel conductance. It is understood and herein contemplated that channelopathy can result from spliceopathy of the ion channel such as ClC-1. Thus, disclosed herein are methods of treating channelopathy comprising administering to a subject in need thereof one of the antisense nucleotides disclosed herein.

"Treatment," "treat," or "treating" mean a method of reducing the effects of a disease or condition. Treatment can also refer to a method of reducing the disease or condition itself rather than just the symptoms. The treatment can be any reduction from native levels and can be but is not limited to the complete ablation of the disease, condition, or the symptoms of the disease or condition. Therefore, in the disclosed methods, treatment" can refer to a 10%, 20%, 30%, 40%, 50%, 60%, 70%, 80%, 90%, or 100% reduction in the severity of an established disease or the disease progression. For example, a disclosed method for reducing the effects of prostate cancer is considered to be a treatment if there is a 10% reduction in one or more symptoms of the disease in a subject with the disease when compared to native levels in the same subject or control subjects. Thus, the reduction can be a 10, 20, 30, 40, 50, 60, 70, 80, 90, 100%, or any amount of reduction in between as compared to native or control levels. It is understood and herein contemplated that "treatment" does not necessarily refer to a cure of the disease or condition, but an improvement in the outlook of a disease or condition. Nevertheless, it is fully contemplated herein that "treatment" can not only refer to the ablation of the disease state, but the reversal of the condition. It is also understood that by correcting or improving spliceopathy, the disease state is being treated. Therefore, herein "improves spliceopathy" or correct spliceopathy" means any change in spliceopathy that results in a change in the degree, amount or action of towards proper regulation of alternative splicing.

It is understood that the morpholinos used in the disclosed methods can comprise repeating nucleotides, for example, CAG25 as set forth in SEQ ID NO: 3. It is understood and herein contemplated that the antisense oligonucleotides for use in the methods or treating disclosed herein can comprise 2, 3, 4, 5, 6, 7, 8, 9 10, 11, 12, 13, 14, 15, 16, 17, 18, 19, 20, 21, 22, 23, 24, or 25 repeats where a 25 repeat would be referred to as CAG75. It is further understood that the antisense oligonucleotides do not have to comprise complete repeats, but can comprise fractions of a repeat. Thus, for example, CAG25 is an 8.3 repeat representing 8 full repeats plus one additional nucleotide. Thus, disclosed herein are repeats comprising 2.3, 2.6, 3.3, 3.6, 4.3, 4.6, 5.3, 5.6, 6.3, 6.6, 7.3, 7.6, 8.3, 8.6, 9.3, 9.6, 10.3, 10.6, 11.3, 11.6, 12.3 12.6, 13.2, 13.6, 14.3, 14.6, 15.3, 15.6, 16.3, 16.6, 17.3, 17.6, 18.3, 18.6, 19.3, 19.6, 20.3, 20.6, 21.3, 21.6, 22.3, 22.6, 23.3, 23.6, 24.3, and 24.6.

It is further understood and herein contemplated that the disclosed antisense oligonucleotides can be modified to be morpholinos. Morpholino refers to synthetic oligonucleotides which have standard nucleic acid bases, bound to morpholine rings rather than the deoxyribose rings of DNA and the bases are linked through phosphorodiamidate groups instead of phosphates. The morpholino operates by binding to complementary RNA and blocks access to the RNA by other molecules. Thus disclosed herein are antisense oligonucleotides as set forth is SEQ ID NO: 3, SEQ ID NO: 4, or SEQ ID NO:5 wherein the antisense oligonucleotide is a morpholino. It is understood that where a particular antisense oligonucleotides is disclosed, contemplated herein is the use of the morpholino variant of that antisense oligonucleotides. Thus, it understood that any of the disclosed methods of treatment can comprise a morpholino-antisense oligonucleotides. Thus, for example, specifically disclosed herein are methods of treatment of DM, wherein the antisense oligonucleotides is a morpholino oligonucleotides. Also disclosed are methods of treating DM, wherein the PNA-antisense oligonucleotides is a the morpholino variant of SEQ ID NO:3, SEQ ID NO:4; or SEQ ID NO:5. Further disclosed are methods of treatment wherein the morpholino antisense oligonucleotides is a CAG, wherein the CAG can comprise 2, 3, 4, 5, 6, 7, 8, 9, 10, 11, 12, 13, 14, 15, 16, 17, 18, 19, 20, 21, 22, 23, 24, or 25 repeats. Thus, for example disclosed herein are methods of treating DM, wherein the CAG comprises 2, 3, 4, or 5 CAG repeats. It is further understood that the antisense oligonucleotides do not have to comprise complete repeats, but can comprise fractions of a repeat. Thus, for example, CAG25 is an 8.3 repeat representing 8 full repeats plus one additional nucleotide. Thus, disclosed herein are repeats comprising 2.3, 2.6, 3.3, 3.6, 4.3, 4.6, 5.3, 5.6, 6.3, 6.6, 7.3, 7.6, 8.3, 8.6, 9.3, 9.6, 10.3, 10.6, 11.3, 11.6, 12.3 12.6, 13.2, 13.6, 14.3, 14.6, 15.3, 15.6, 16.3, 16.6, 17.3, 17.6, 18.3, 18.6, 19.3, 19.6, 20.3, 20.6, 21.3, 21.6, 22.3, 22.6, 23.3, 23.6, 24.3, and 24.6.

It is further understood and herein contemplated that the disclosed antisense oligonucleotides can be modified to incorporate peptide nucleic acids as the sugar backbone to the antisense oligonucleotides. Peptide nucleic acids (PNA) "are synthetic analogue of DNA and RNA, in which the naturally occurring sugarphosphate backbone has been replaced by N-(2-aminoethyl) glycine units. PNA can hybridize to complementary DNA or RNA strand through Watson-Crick base-pairing to form a hybrid duplex, with high affinity and sequence selectivity. The high binding affinity of PNA has been attributed in part to the lack of electrostatic repulsion. In addition to conferring hybridization stability, the neutral polyamide backbone provides the added benefit of enzymatic stability, making PNA resistant to both proteases and nucleases. Together these properties make PNA an attractive reagent for biotechnology applications. However, unlike DNA or RNA in the unhybridized state (single strand) whose structure, to a large degree, is extended in solution due to the negatively charged phosphate backbone, PNA tends to fold into complex globular structures, presumably due to the collapse of the hydrophobic nucleobases. In fact, this conformational collapse has been exploited in the development of stemless PNA molecular beacons, taking advantage of the proximity between the two termini in the unhybridized state. Several modifications have been made to the PNA N-(2-aminoethyl) glycine backbone in attempts to increase its rigidity." (Dragulesca-Andrasi, A et al. (2006) JACS 128: 10258-10267)

One modification, GPNA, an analogue of PNA containing internally linked D-arginine side chains, binds to RNA with high affinity and sequence selectivity and is readily taken up by mammalian cells. Alternatively, a simple ç-backbone modification can transform a randomly folded peptide nucleic acid (PNA) into a right-handed helix. These conformationally preorganized helical PNAs bind to DNA and RNA with exceptionally high affinity and sequence selectivity. It is understood that the antisense oligonucleotide disclosed herein can comprise PNA. Thus, for example, disclosed herein is PNA-CAG25. Also disclosed are the antisense oligonucleotides set forth in SEQ ID NO:3, SEQ ID NO:4; SEQ ID NO:5; or SEQ ID NO:6, wherein the backbone has been modified as a PNA. It is understood that where a particular antisense oligonucleotides is disclosed, contemplated herein is the use of the PNA variant of that antisense oligonucleotides. Thus, it understood that any of the disclosed methods of treatment can comprise a PNA-antisense oligonucleotides. Thus, for example, specifically disclosed herein are methods of treatment of DM, wherein the antisense oligonucleotides is a peptide nucleic acid antisense oligonucleotides. Also disclosed are methods of treating DM, wherein the PNA-antisense oligonucleotides is a the PNA variant of SEQ ID NO:3, SEQ ID NO:4; and SEQ ID NO:5. Further disclosed are methods of treatment wherein the PNA antisense oligonucleotides is a PNA-CAG, wherein the PNA-CAG can comprise 2, 3, 4, 5, 6, 7, 8, 9, 10, 11, 12, 13, 14, 15, 16, 17, 18, 19, 20, 21, 22, 23, 24, or 25 repeats. Thus, for example disclosed herein are methods of treating DM, wherein the PNA-CAG comprises 2, 3, 4, or 5 CAG repeats. It is further understood that the antisense oligonucleotides do not have to comprise complete repeats, but can comprise fractions of a repeat. Thus, for example, PNA-CAG25 is an 8.3 repeat representing 8 full repeats plus one additional nucleotide. Thus, disclosed herein are repeats comprising 2.3, 2.6, 3.3, 3.6, 4.3, 4.6, 5.3, 5.6, 6.3, 6.6, 7.3, 7.6, 8.3, 8.6, 9.3, 9.6, 10.3, 10.6, 11.3, 11.6, 12.3 12.6, 13.2, 13.6, 14.3, 14.6, 15.3, 15.6, 16.3, 16.6, 17.3, 17.6, 18.3, 18.6, 19.3, 19.6, 20.3, 20.6, 21.3, 21.6, 22.3, 22.6, 23.3, 23.6, 24.3, and 24.6.

Thus, for example, treating DM1 can comprise any method or the administration of any agent that affects spliceopathy in a manner that ameliorates a symptom or causative event associated with DM1. For example, a morpholino that corrects spliceopathy associated with ClC1 or displaces MBNL1 on poly(CUG)$^{exp}$.

Herein is disclosed that that a antisense oligonucleotide (AON) targeting the 3' splice site of the chloride ion channel (ClC-1) exon 7a reverses the defect of ClC-1 alternative splicing in two mouse models of DM. By repressing the inclusion of this exon, the AON restores the full-length reading frame in ClC-1 mRNA, upregulates the level of ClC-1 mRNA, increases the expression of ClC-1 protein in the surface membrane, normalizes muscle ClC-1 current density and deactivation kinetics, and eliminates myotonic discharges. These observations indicate that the myotonia and chloride channelopathy in DM both result from abnormal alternative splicing of ClC-1 and that antisense-induced exon skipping offers a powerful method for correcting alternative splicing defects in DM. It is therefore understood and herein contemplated that the disclosed methods can comprise methods of treating DM, wherein the myotonia is the result of channelopathy resulting from spliceopathy. Therefore, disclosed herein are methods or treating myotonic dystrophy in a subject in need thereof comprising administering to the subject an agent that corrects spliceopathy, wherein the spliceopathy results in channelopathy.

3. Delivery of the Compositions to Cells

There are a number of compositions and methods which can be used to deliver nucleic acids to cells, either in vitro or in vivo. These methods and compositions can largely be broken down into two classes: viral based delivery systems and non-viral based delivery systems. For example, the nucleic acids can be delivered through a number of direct delivery systems such as, electroporation, lipofection, calcium phosphate precipitation, plasmids, viral vectors, viral nucleic acids, phage nucleic acids, phages, cosmids, or via transfer of genetic material in cells or carriers such as cationic liposomes. Appropriate means for transfection, including viral vectors, chemical transfectants, or physico-mechanical methods such as electroporation and direct diffusion of DNA, are described by, for example, Wolff, J. A., et al., Science, 247, 1465-1468, (1990); and Wolff, J. A. Nature, 352, 815-818, (1991). Such methods are well known in the art and readily adaptable for use with the compositions and methods described herein. In certain cases, the methods will be modified to specifically function with large DNA molecules. Further, these methods can be used to target certain diseases and cell populations by using the targeting characteristics of the carrier.

a) Nucleic Acid Based Delivery Systems

Transfer vectors can be any nucleotide construction used to deliver genes into cells (e.g., a plasmid), or as part of a general strategy to deliver genes, e.g., as part of recombinant retrovirus or adenovirus (Ram et al. Cancer Res. 53:83-88, (1993)).

As used herein, plasmid or viral vectors are agents that transport the disclosed nucleic acids, such as MBNL1, p(CUG)$^{exp}$, and CAG25 or other antisense oligonucleotide into the cell without degradation and include a promoter yielding expression of the gene in the cells into which it is delivered. Viral vectors are, for example, Adenovirus, Adeno-associated virus, Herpes virus, Vaccinia virus, Polio virus, AIDS virus, neuronal trophic virus, Sindbis and other RNA viruses, including these viruses with the HIV backbone. Also preferred are any viral families which share the properties of these viruses which make them suitable for use as vectors. Retroviruses include Murine Maloney Leukemia virus, MMLV, and retroviruses that express the desirable properties of MMLV as a vector. Retroviral vectors are able to carry a larger genetic payload, i.e., a transgene or marker gene, than other viral vectors, and for this reason are a commonly used vector. However, they are not as useful in non-proliferating cells. Adenovirus vectors are relatively stable and easy to work with, have high titers, and can be delivered in aerosol formulation, and can transfect non-dividing cells. Pox viral vectors are large and have several sites for inserting genes, they are thermostable and can be stored at room temperature. A preferred embodiment is a viral vector which has been engineered so as to suppress the immune response of the host organism, elicited by the viral antigens. Preferred vectors of this type will carry coding regions for Interleukin 8 or 10.

Viral vectors can have higher transaction (ability to introduce genes) abilities than chemical or physical methods to introduce genes into cells. Typically, viral vectors contain, nonstructural early genes, structural late genes, an RNA polymerase III transcript, inverted terminal repeats necessary for replication and encapsidation, and promoters to control the transcription and replication of the viral genome. When engineered as vectors, viruses typically have one or more of the early genes removed and a gene or gene/promotor cassette is inserted into the viral genome in place of the removed viral DNA. Constructs of this type can carry up to about 8 kb of foreign genetic material. The necessary functions of the removed early genes are typically supplied by cell lines which have been engineered to express the gene products of the early genes in trans.

(1) Retroviral Vectors

A retrovirus is an animal virus belonging to the virus family of Retroviridae, including any types, subfamilies, genus, or tropisms. Retroviral vectors, in general, are described by Verma, I. M., Retroviral vectors for gene transfer. In *Microbiology*—1985, American Society for Microbiology, pp. 229-232, Washington, (1985), which is incorporated by reference herein. Examples of methods for using retroviral vectors for gene therapy are described in U.S. Pat. Nos. 4,868,116 and 4,980,286; PCT applications WO 90/02806 and WO 89/07136; and Mulligan, (*Science* 260:926-932 (1993)); the teachings of which are incorporated herein by reference.

A retrovirus is essentially a package which has packed into it nucleic acid cargo. The nucleic acid cargo carries with it a packaging signal, which ensures that the replicated daughter molecules will be efficiently packaged within the package coat. In addition to the package signal, there are a number of molecules which are needed in cis, for the replication, and packaging of the replicated virus. Typically a retroviral genome, contains the gag, pol, and env genes which are involved in the making of the protein coat. It is the gag, pol, and env genes which are typically replaced by the foreign DNA that it is to be transferred to the target cell. Retrovirus vectors typically contain a packaging signal for incorporation into the package coat, a sequence which signals the start of the gag transcription unit, elements necessary for reverse transcription, including a primer binding site to bind the tRNA primer of reverse transcription, terminal repeat sequences that guide the switch of RNA strands during DNA synthesis, a purine rich sequence 5' to the 3' LTR that serve as the priming site for the synthesis of the second strand of DNA synthesis, and specific sequences near the ends of the LTRs that enable the insertion of the DNA state of the retrovirus to insert into the host genome. The removal of the gag, pol, and env genes allows for about 8 kb of foreign sequence to be inserted into the viral genome, become reverse transcribed, and upon replication be packaged into a new retroviral particle. This amount of nucleic acid is sufficient for the delivery of a one to many genes depending on the size of each transcript. It is preferable to include either positive or negative selectable markers along with other genes in the insert.

Since the replication machinery and packaging proteins in most retroviral vectors have been removed (gag, pol, and env), the vectors are typically generated by placing them into a packaging cell line. A packaging cell line is a cell line which has been transfected or transformed with a retrovirus that contains the replication and packaging machinery, but lacks any packaging signal. When the vector carrying the DNA of choice is transfected into these cell lines, the vector containing the gene of interest is replicated and packaged into new retroviral particles, by the machinery provided in cis by the helper cell. The genomes for the machinery are not packaged because they lack the necessary signals.

(2) Adenoviral Vectors

The construction of replication-defective adenoviruses has been described (Berkner et al., *J. Virology* 61:1213-1220 (1987); Massie et al., *Mol. Cell. Biol.* 6:2872-2883 (1986); Haj-Ahmad et al., *J. Virology* 57:267-274 (1986); Davidson et al., *J. Virology* 61:1226-1239 (1987); Zhang "Generation and identification of recombinant adenovirus by liposome-mediated transfection and PCR analysis" *BioTechniques* 15:868-872 (1993)). The benefit of the use of these viruses as vectors is that they are limited in the extent to which they can spread to other cell types, since they can replicate within an initial infected cell, but are unable to form new infectious viral particles. Recombinant adenoviruses have been shown to achieve high efficiency gene transfer after direct, in vivo delivery to airway epithelium, hepatocytes, vascular endothelium, CNS parenchyma and a number of other tissue sites (Morsy, *J. Clin. Invest.* 92:1580-1586 (1993); Kirshenbaum, *J. Clin. Invest.* 92:381-387 (1993); Roessler, *J. Clin. Invest.* 92:1085-1092 (1993); Moullier, *Nature Genetics* 4:154-159 (1993); La Salle, *Science* 259:988-990 (1993); Gomez-Foix, *J. Biol. Chem.* 267:25129-25134 (1992); Rich, *Human Gene Therapy* 4:461-476 (1993); Zabner, *Nature Genetics* 6:75-83 (1994); Guzman, *Circulation Research* 73:1201-1207 (1993); Bout, *Human Gene Therapy* 5:3-10 (1994); Zabner, *Cell* 75:207-216 (1993); Caillaud, Eur. *J. Neuroscience* 5:1287-1291 (1993); and Ragot, *J. Gen. Virology* 74:501-507 (1993)). Recombinant adenoviruses achieve gene transduction by binding to specific cell surface receptors, after which the virus is internalized by receptor-mediated endocytosis, in the same manner as wild type or replication-defective adenovirus (Chardonnet and Dales, *Virology* 40:462-477 (1970); Brown and Burlingham, *J. Virology* 12:386-396 (1973); Svensson and Persson, *J. Virology* 55:442-449 (1985); Seth, et al., *J. Virol.* 51:650-655 (1984); Seth, et al., *Mol. Cell. Biol.* 4:1528-1533 (1984); Varga et al., *J. Virology* 65:6061-6070 (1991); Wickham et al., *Cell* 73:309-319 (1993)).

A viral vector can be one based on an adenovirus which has had the E1 gene removed and these virons are generated in a cell line such as the human 293 cell line. In another preferred embodiment both the E1 and E3 genes are removed from the adenovirus genome.

(3) Adeno-Associated Viral Vectors

Another type of viral vector is based on an adeno-associated virus (AAV). This defective parvovirus is a preferred vector because it can infect many cell types and is nonpathogenic to humans. AAV type vectors can transport about 4 to 5 kb and wild type AAV is known to stably insert into chromosome 19. Vectors which contain this site specific integration property are preferred. An especially preferred embodiment of this type of vector is the P4.1 C vector produced by Avigen, San Francisco, Calif., which can contain the herpes simplex virus thymidine kinase gene, HSV-tk, and/or a marker gene, such as the gene encoding the green fluorescent protein, GFP.

In another type of AAV virus, the AAV contains a pair of inverted terminal repeats (ITRs) which flank at least one cassette containing a promoter which directs cell-specific expression operably linked to a heterologous gene. Heterologous in this context refers to any nucleotide sequence or gene which is not native to the AAV or B19 parvovirus.

Typically the AAV and B19 coding regions have been deleted, resulting in a safe, noncytotoxic vector. The AAV ITRs, or modifications thereof, confer infectivity and site-specific integration, but not cytotoxicity, and the promoter directs cell-specific expression. U.S. Pat. No. 6,261,834 is herein incorporated by reference for material related to the AAV vector.

The disclosed vectors thus provide DNA molecules which are capable of integration into a mammalian chromosome without substantial toxicity.

The inserted genes in viral and retroviral usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

(4) Large Payload Viral Vectors

Molecular genetic experiments with large human herpesviruses have provided a means whereby large heterologous DNA fragments can be cloned, propagated and established in cells permissive for infection with herpesviruses (Sun et al., *Nature Genetics* 8: 33-41, 1994; Cotter and Robertson, *Curr Opin Mol Ther* 5: 633-644, 1999). These large DNA viruses (herpes simplex virus (HSV) and Epstein-Barr virus (EBV), have the potential to deliver fragments of human heterologous DNA >150 kb to specific cells. EBV recombinants can maintain large pieces of DNA in the infected B-cells as episomal DNA. Individual clones carried human genomic inserts up to 330 kb appeared genetically stable the maintenance of these episomes requires a specific EBV nuclear protein, EBNA1, constitutively expressed during infection with EBV. Additionally, these vectors can be used for transfection, where large amounts of protein can be generated transiently in vitro. Herpesvirus amplicon systems are also being used to package pieces of DNA >220 kb and to infect cells that can stably maintain DNA as episomes.

Other useful systems include, for example, replicating and host-restricted non-replicating vaccinia virus vectors.

b) Non-Nucleic Acid Based Systems

The disclosed compositions can be delivered to the target cells in a variety of ways. For example, the compositions can be delivered through electroporation, or through lipofection, or through calcium phosphate precipitation. The delivery mechanism chosen will depend in part on the type of cell targeted and whether the delivery is occurring for example in vivo or in vitro.

Thus, the compositions can comprise, in addition to the disclosed CAG25 or MBNL1 vectors for example, lipids such as liposomes, such as cationic liposomes (e.g., DOTMA, DOPE, DC-cholesterol) or anionic liposomes, or protein transduction domains. Liposomes can further comprise proteins to facilitate targeting a particular cell, if desired. Administration of a composition comprising a compound and a cationic liposome can be administered to the blood afferent to a target organ or inhaled into the respiratory tract to target cells of the respiratory tract. Regarding liposomes, see, e.g., Brigham et al. *Am. J. Resp. Cell. Mol. Biol.* 1:95-100 (1989); Felgner et al. *Proc. Natl. Acad. Sci. USA* 84:7413-7417 (1987); U.S. Pat. No. 4,897,355. It is understood that protein transduction domains, can comprise a domain from a larger protein, such as HIV-1 tat protein or herpes virus VP22, or an engineered peptide such as Endo-Porter™. Furthermore, the compound can be administered as a component of a microcapsule that can be targeted to specific cell types, such as macrophages, or where the diffusion of the compound or delivery of the compound from the microcapsule is designed for a specific rate or dosage.

In the methods described above which include the administration and uptake of exogenous DNA into the cells of a subject (i.e., gene transduction or transfection), delivery of the compositions to cells can be via a variety of mechanisms. As one example, delivery can be via a liposome, using commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art. In addition, the disclosed nucleic acid or vector can be delivered in vivo by electroporation, the technology for which is available from Genetronics, Inc. (San Diego, Calif.) as well as by means of a SONOPORATION machine (ImaRx Pharmaceutical Corp., Tucson, Ariz.).

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129: 57-80, (1992); and Roffler, et al., *Biochem. Pharmacol*, 42:2062-2065, (1991)). These techniques can be used for a variety of other specific cell types. Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

Nucleic acids that are delivered to cells which are to be integrated into the host cell genome, typically contain integration sequences. These sequences are often viral related sequences, particularly when viral based systems are used. These viral intergration systems can also be incorporated into nucleic acids which are to be delivered using a non-nucleic acid based system of deliver, such as a liposome, so that the nucleic acid contained in the delivery system can be come integrated into the host genome.

Other general techniques for integration into the host genome include, for example, systems designed to promote homologous recombination with the host genome. These systems typically rely on sequence flanking the nucleic acid to be expressed that has enough homology with a target sequence within the host cell genome that recombination between the vector nucleic acid and the target nucleic acid takes place, causing the delivered nucleic acid to be integrated into the host genome. These systems and the methods necessary to promote homologous recombination are known to those of skill in the art.

c) In Vivo/Ex Vivo

As described above, the compositions can be administered in a pharmaceutically acceptable carrier and can be delivered to the subject's cells in vivo and/or ex vivo by a variety of mechanisms well known in the art (e.g., uptake of naked DNA, liposome fusion, intramuscular injection of DNA via a gene gun, endocytosis and the like).

If ex vivo methods are employed, cells or tissues can be removed and maintained outside the body according to standard protocols well known in the art. The compositions can be introduced into the cells via any gene transfer mechanism, such as, for example, calcium phosphate mediated gene delivery, electroporation, microinjection or proteoliposomes. The transduced cells can then be infused (e.g., in a pharmaceutically acceptable carrier) or homotopically transplanted back into the subject per standard methods for the cell or tissue type. Standard methods are known for transplantation or infusion of various cells into a subject.

4. Expression Systems

The nucleic acids that are delivered to cells typically contain expression controlling systems. For example, the inserted genes in viral and retroviral systems usually contain promoters, and/or enhancers to help control the expression of the desired gene product. A promoter is generally a sequence or sequences of DNA that function when in a relatively fixed location in regard to the transcription start site. A promoter contains core elements required for basic interaction of RNA polymerase and transcription factors, and may contain upstream elements and response elements.

a) Viral Promoters and Enhancers

Preferred promoters controlling transcription from vectors in mammalian host cells may be obtained from various sources, for example, the genomes of viruses such as: polyoma, Simian Virus 40 (SV40), adenovirus, retroviruses, hepatitis-B virus and most preferably cytomegalovirus, or from heterologous mammalian promoters, e.g. beta actin promoter. The early and late promoters of the SV40 virus are conveniently obtained as an SV40 restriction fragment which also contains the SV40 viral origin of replication (Fiers et al., *Nature,* 273: 113 (1978)). The immediate early promoter of the human cytomegalovirus is conveniently obtained as a HindIII E restriction fragment (Greenway, P. J. et al., *Gene* 18: 355-360 (1982)). Of course, promoters from the host cell or related species also are useful herein.

Enhancer generally refers to a sequence of DNA that functions at no fixed distance from the transcription start site and can be either 5' (Laimins, L. et al., *Proc. Natl. Acad. Sci.* 78: 993 (1981)) or 3' (Lusky, M. L., et al., *Mol. Cell Bio.* 3: 1108 (1983)) to the transcription unit. Furthermore, enhancers can be within an intron (Banerji, J. L. et al., *Cell* 33: 729 (1983)) as well as within the coding sequence itself (Osborne, T. F., et al., *Mol. Cell Bio.* 4: 1293 (1984)). They are usually between 10 and 300 bp in length, and they function in cis. Enhancers function to increase transcription from nearby promoters. Enhancers also often contain response elements that mediate the regulation of transcription. Promoters can also contain response elements that mediate the regulation of transcription. Enhancers often determine the regulation of expression of a gene. While many enhancer sequences are now known from mammalian genes (globin, elastase, albumin, -fetoprotein and insulin), typically one will use an enhancer from a eukaryotic cell virus for general expression. Preferred examples are the SV40 enhancer on the late side of the replication origin (bp 100-270), the cytomegalovirus early promoter enhancer, the polyoma enhancer on the late side of the replication origin, and adenovirus enhancers.

The promotor and/or enhancer may be specifically activated either by light or specific chemical events which trigger their function. Systems can be regulated by reagents such as tetracycline and dexamethasone. There are also ways to enhance viral vector gene expression by exposure to irradiation, such as gamma irradiation, or alkylating chemotherapy drugs.

In certain embodiments the promoter and/or enhancer region can act as a constitutive promoter and/or enhancer to maximize expression of the region of the transcription unit to be transcribed. In certain constructs the promoter and/or enhancer region be active in all eukaryotic cell types, even if it is only expressed in a particular type of cell at a particular time. A preferred promoter of this type is the CMV promoter (650 bases). Other preferred promoters are SV40 promoters, cytomegalovirus (full length promoter), and retroviral vector LTF.

It has been shown that all specific regulatory elements can be cloned and used to construct expression vectors that are selectively expressed in specific cell types such as melanoma cells. The glial fibrillary acetic protein (GFAP) promoter has been used to selectively express genes in cells of glial origin.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding tissue factor protein. The 3' untranslated regions also include transcription termination sites. It is preferred that the transcription unit also contains a polyadenylation region. One benefit of this region is that it increases the likelihood that the transcribed unit will be processed and transported like mRNA. The identification and use of polyadenylation signals in expression constructs is well established. It is preferred that homologous polyadenylation signals be used in the transgene constructs. In certain transcription units, the polyadenylation region is derived from the SV40 early polyadenylation signal and consists of about 400 bases. It is also preferred that the transcribed units contain other standard sequences alone or in combination with the above sequences improve expression from, or stability of, the construct.

b) Markers

The viral vectors can include nucleic acid sequence encoding a marker product. This marker product is used to determine if the gene has been delivered to the cell and once delivered is being expressed. Preferred marker genes are the *E. Coli* lacZ gene, which encodes β-galactosidase, and green fluorescent protein.

In some embodiments the marker may be a selectable marker. Examples of suitable selectable markers for mammalian cells are dihydrofolate reductase (DHFR), thymidine kinase, neomycin, neomycin analog G418, hydromycin, and puromycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented media. Two examples are: CHO DHFR– cells and mouse LTK– cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented media. An alternative to supplementing the media is to introduce an intact DHFR or TK gene into cells lacking the respective genes, thus altering their growth requirements. Individual cells which were not transformed with the DHFR or TK gene will not be capable of survival in non-supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, (Southern P. and Berg, P., *J. Molec. Appl. Genet.* 1: 327 (1982)), mycophenolic acid, (Mulligan, R. C. and Berg, P. *Science* 209: 1422 (1980)) or hygromycin, (Sugden, B. et al., *Mol. Cell. Biol.* 5: 410-413 (1985)). The three examples employ bacterial genes under eukaryotic control to convey resistance to the appropriate drug G418 or neomycin (geneticin), xgpt (mycophenolic acid) or hygromycin, respectively. Others include the neomycin analog G418 and puramycin.

C. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular CAG25 antisense oligonucleotide is disclosed and discussed and a number of modifications that can be made to a number of molecules including the CAG25 antisense oligonucleotide are discussed, specifically contemplated is each and every combination and permutation of CAG25 antisense oligonucleotide and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Figure 18:
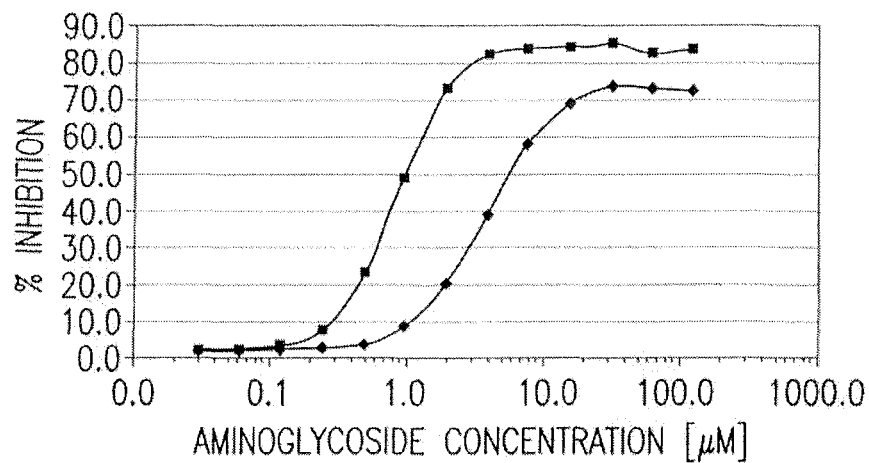
FIG. 18 shows that filter binding screening assay identifies compounds in the aminoglycoside family as having ability to inhibit interaction of recombinant MBNL1 protein with $(CUG)_{109}$ RNA. Among 9 aminoglycoside compounds tested, neomycin (left curve) and gentamicin (right curve) showed the highest activity to inhibit formation of MBNL1-poly$(CUG)^{exp}$ RNA-protein complexes. The order of addition was compound+$(CUG)_{109}$ RNA (incubate 5 minutes), followed by recombinant MBNL1 protein (15 minute incubation), followed by application to filter.
Figure 19:
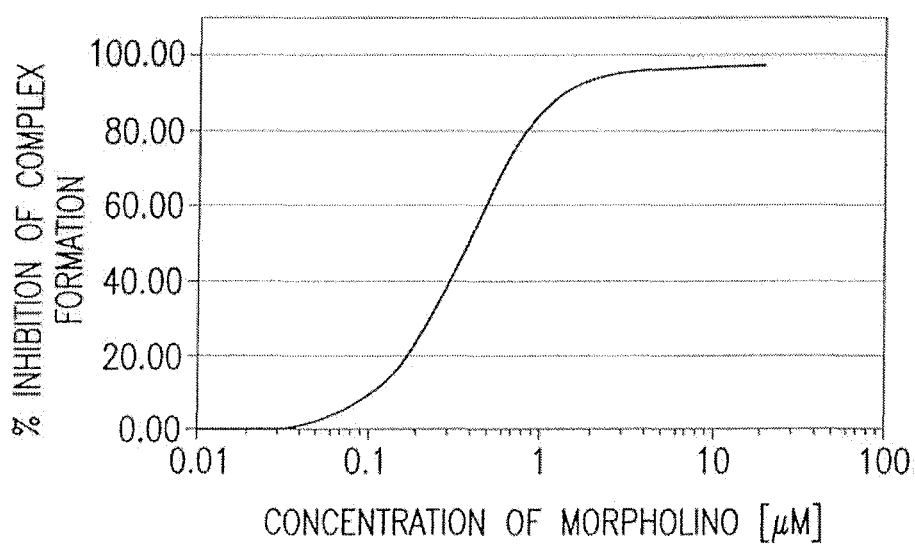
FIG. 19 shows that CAG25 morpholino inhibits the interaction of MBNL1-poly$(CUG)^{exp}$ RNA in vitro. Interaction of recombinant MBNL1 protein with $(CUG)_{109}$ RNA was examined by gel shift assay, in the presence of increasing amounts of CAG25 morpholino.
Figure 20:
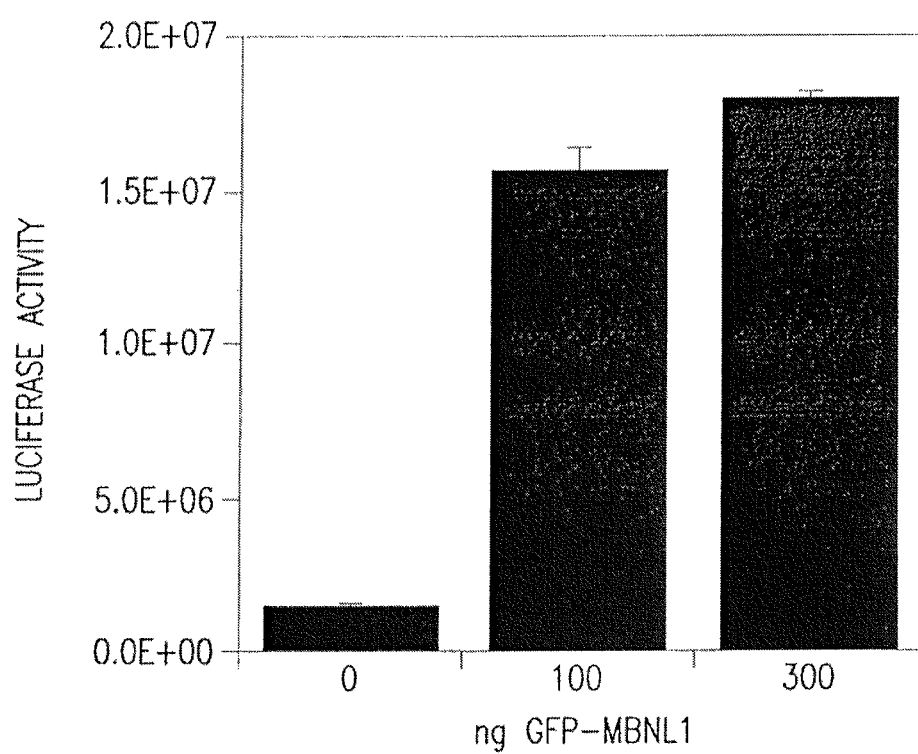
FIG. 20 shows a screening assay for compounds that improve spliceopathy could use readouts other than protein fluorescence. SERCA1 exon 22 and flanking introns are used to generate a spliceopathy reporter construct using luciferase. Point mutations have been induced in SERCA1 exon 22 so that it no longer encodes a termination codon. When this spliceopathy reporter construct is transiently transfected in COS cells, the luciferase activity is sensitive indicator of MBNL1 activity, as indicated by the >10-fold upregulation of luciferase when cotransfected with small amounts of expression construct for GFP-tagged MBNL1.
Figure 21A:
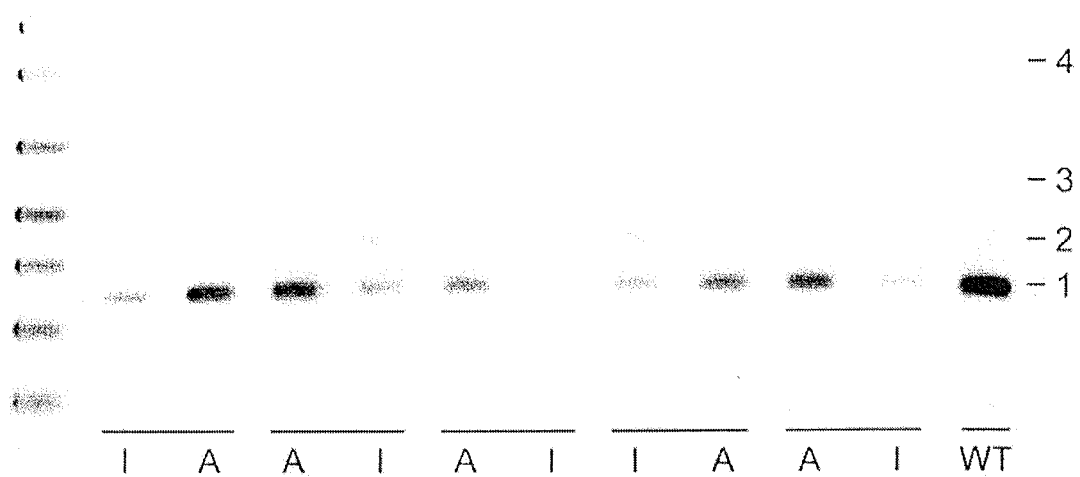

Disclosed herein are compositions that can be used to treat DM1 or DM2. For example, disclosed herein are morpholinos such as CAG25 and the antisense oligonucleotide as set forth in SEQ ID NO: 4, that can treat DM1. Also disclosed are small molecules such as aminoglycoside antibiotics neomycin and gentamicin. It is understood that other aminoglycoside family members such as those disclosed in FIG. 18 are also disclosed for treating DM1 or DM2.

Herein, "morpholino" refers to synthetic oligonucleotides which have standard nucleic acid bases, bound to morpholine rings rather than the deoxyribose rings of DNA and the bases are linked through phosphorodiamidate groups instead of phosphates. The morpholino operates by binding to complementary RNA and blocks access to the RNA by other molecules. Disclosed herein, the morpholino may also be used to displace a molecule that is already bound to the complementary RNA strand.

1. Homology/Identity

It is understood that one way to define any known variants and derivatives or those that might arise, of the disclosed genes and proteins herein is through defining the variants and derivatives in terms of homology to specific known sequences. For example SEQ ID NO: 1 sets forth a particular sequence of an MBNL1 and SEQ ID NO: 2 sets forth a particular sequence of the protein encoded by SEQ ID NO:1, an MBNL1 protein. Specifically disclosed are variants of these and other genes and proteins herein disclosed which have at least, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 percent homology to the stated sequence. Those of skill in the art readily understand how to determine the homology of two proteins or nucleic acids, such as genes. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. Mol. Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

2. Hybridization/Selective Hybridization

The term hybridization typically means a sequence driven interaction between at least two nucleic acid molecules, such as a primer or a probe and a gene. Sequence driven interaction means an interaction that occurs between two nucleotides or nucleotide analogs or nucleotide derivatives in a nucleotide specific manner. For example, G interacting with C or A interacting with T are sequence driven interactions. Typically sequence driven interactions occur on the Watson-Crick face or Hoogsteen face of the nucleotide. The hybridization of two nucleic acids is affected by a number of conditions and parameters known to those of skill in the art. For example, the salt concentrations, pH, and temperature of the reaction all affect whether two nucleic acid molecules will hybridize.

Parameters for selective hybridization between two nucleic acid molecules are well known to those of skill in the art. For example, in some embodiments selective hybridization conditions can be defined as stringent hybridization conditions. For example, stringency of hybridization is controlled by both temperature and salt concentration of either or both of the hybridization and washing steps. For example, the conditions of hybridization to achieve selective hybridization may involve hybridization in high ionic strength solution (6×SSC or 6×SSPE) at a temperature that is about 12-25° C. below the Tm (the melting temperature at which half of the molecules dissociate from their hybridization partners) followed by washing at a combination of temperature and salt concentration chosen so that the washing temperature is about 5° C. to 20° C. below the Tm. The temperature and salt conditions are readily determined empirically in preliminary experiments in which samples of reference DNA immobilized on filters are hybridized to a labeled nucleic acid of interest and then washed under conditions of different stringencies. Hybridization temperatures are typically higher for DNA-RNA and RNA-RNA hybridizations. The conditions can be used as described above to achieve stringency, or as is known in the art. (Sambrook et al., *Molecular Cloning: A Laboratory Manual,* 2nd Ed., Cold Spring Harbor Laboratory, Cold Spring Harbor, N.Y., 1989; Kunkel et al. Methods Enzymol. 1987:154:367, 1987 which is herein incorporated by reference for material at least related to hybridization of nucleic acids). A preferable stringent hybridization condition for a DNA:DNA hybridization can be at about 68° C. (in aqueous solution) in 6×SSC or 6×SSPE followed by washing at 68° C. Stringency of hybridization and washing, if desired, can be reduced accordingly as the degree of complementarity desired is decreased, and further, depending upon the G-C or A-T richness of any area wherein variability is searched for. Likewise, stringency of hybridization and washing, if desired, can be increased accordingly as homology desired is increased, and further, depending upon the G-C or A-T richness of any area wherein high homology is desired, all as known in the art.

Another way to define selective hybridization is by looking at the amount (percentage) of one of the nucleic acids bound to the other nucleic acid. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the limiting nucleic acid is bound to the non-limiting nucleic acid. Typically, the non-limiting primer is in for example, 10 or 100 or 1000 fold excess. This type of assay can be performed at under conditions where both the limiting and non-limiting primer are for example, 10 fold or 100 fold or 1000 fold below their $k_d$, or where only one of the nucleic acid molecules is 10 fold or 100 fold or 1000 fold or where one or both nucleic acid molecules are above their $k_d$.

Another way to define selective hybridization is by looking at the percentage of primer that gets enzymatically manipulated under conditions where hybridization is required to promote the desired enzymatic manipulation. For example, in some embodiments selective hybridization conditions would be when at least about, 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer is enzymatically manipulated under conditions which promote the enzymatic manipulation, for example if the enzymatic manipulation is DNA extension, then selective hybridization conditions would be when at least about 60, 65, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 percent of the primer molecules are extended. Preferred conditions also include those suggested by the manufacturer or indicated in the art as being appropriate for the enzyme performing the manipulation.

Just as with homology, it is understood that there are a variety of methods herein disclosed for determining the level of hybridization between two nucleic acid molecules. It is understood that these methods and conditions may provide different percentages of hybridization between two nucleic acid molecules, but unless otherwise indicated meeting the parameters of any of the methods would be sufficient. For example if 80% hybridization was required and as long as hybridization occurs within the required parameters in any one of these methods it is considered disclosed herein.

It is understood that those of skill in the art understand that if a composition or method meets any one of these criteria for determining hybridization either collectively or singly it is a composition or method that is disclosed herein.

3. Nucleic Acids

There are a variety of molecules disclosed herein that are nucleic acid based, including for example the nucleic acids that encode, for example, CAG25 as well as any other proteins disclosed herein, as well as various functional nucleic acids. The disclosed nucleic acids are made up of for example, nucleotides, nucleotide analogs, or nucleotide substitutes. Non-limiting examples of these and other molecules are discussed herein. It is understood that for example, when a vector is expressed in a cell, that the expressed mRNA will typically be made up of A, C, G, and U. Likewise, it is understood that if, for example, an antisense molecule is introduced into a cell or cell environment through for example exogenous delivery, it is advantageous that the antisense molecule be made up of nucleotide analogs that reduce the degradation of the antisense molecule in the cellular environment.

a) Nucleotides and Related Molecules

A nucleotide is a molecule that contains a base moiety, a sugar moiety and a phosphate moiety. Nucleotides can be linked together through their phosphate moieties and sugar moieties creating an internucleoside linkage. The base moiety of a nucleotide can be adenin-9-yl (A), cytosin-1-yl (C), guanin-9-yl (G), uracil-1-yl (U), and thymin-1-yl (T). The sugar moiety of a nucleotide is a ribose or a deoxyribose. The phosphate moiety of a nucleotide is pentavalent phosphate. An non-limiting example of a nucleotide would be 3'-AMP (3'-adenosine monophosphate) or 5'-GMP (5'-guanosine monophosphate).

A nucleotide analog is a nucleotide which contains some type of modification to either the base, sugar, or phosphate moieties. Modifications to nucleotides are well known in the art and would include for example, 5-methylcytosine (5-me-C), 5-hydroxymethyl cytosine, xanthine, hypoxanthine, and 2-aminoadenine as well as modifications at the sugar or phosphate moieties.

Nucleotide substitutes are molecules having similar functional properties to nucleotides, but which do not contain a phosphate moiety, such as peptide nucleic acid (PNA). Nucleotide substitutes are molecules that will recognize nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

It is also possible to link other types of molecules (conjugates) to nucleotides or nucleotide analogs to enhance for example, cellular uptake. Conjugates can be chemically linked to the nucleotide or nucleotide analogs. Such conjugates include but are not limited to lipid moieties such as a cholesterol moiety. (Letsinger et al., Proc. Natl. Acad. Sci. USA, 1989, 86, 6553-6556), A Watson-Crick interaction is at least one interaction with the Watson-Crick face of a nucleotide, nucleotide analog, or nucleotide substitute. The Watson-Crick face of a nucleotide, nucleotide analog, or nucleotide substitute includes the C2, $N_1$, and C6 positions of a purine based nucleotide, nucleotide analog, or nucleotide substitute and the C2, N3, C4 positions of a pyrimidine based nucleotide, nucleotide analog, or nucleotide substitute.

A Hoogsteen interaction is the interaction that takes place on the Hoogsteen face of a nucleotide or nucleotide analog, which is exposed in the major groove of duplex DNA. The Hoogsteen face includes the N7 position and reactive groups (NH2 or O) at the C6 position of purine nucleotides.

b) Sequences

There are a variety of sequences related to the protein molecules disclosed herein, for example MBNL1, or any of the nucleic acids disclosed herein for making CAG25, all of which are encoded by nucleic acids or are nucleic acids. The sequences for the human analogs of these genes, as well as other analogs, and alleles of these genes, and splice variants and other types of variants, are available in a variety of protein and gene databases, including Genbank. Those sequences available at the time of filing this application at Genbank are herein incorporated by reference in their entireties as well as for individual subsequences contained therein. Genbank can be accessed at http://www.ncbi.nih.gov/entrez/query.fcgi. Those of skill in the art understand how to resolve sequence discrepancies and differences and to adjust the compositions and methods relating to a particular sequence to other related sequences. Primers and/or probes can be designed for any given sequence given the information disclosed herein and known in the art.

c) Primers and Probes

Disclosed are compositions including primers and probes, which are capable of interacting with the disclosed nucleic acids, such as the poly(CUG)$^{exp}$ as disclosed herein. In certain embodiments the primers are used to support DNA amplification reactions. Typically the primers will be capable of being extended in a sequence specific manner. Extension of a primer in a sequence specific manner includes any methods wherein the sequence and/or composition of the nucleic acid molecule to which the primer is hybridized or otherwise associated directs or influences the composition or sequence of the product produced by the extension of the primer. Extension of the primer in a sequence specific manner therefore includes, but is not limited to, PCR, DNA sequencing, DNA extension, DNA polymerization, RNA transcription, or reverse transcription. Techniques and conditions that amplify the primer in a sequence specific manner are preferred. In certain embodiments the primers are used for the DNA amplification reactions, such as PCR or direct sequencing. It is understood that in certain embodiments the primers can also be extended using non-enzymatic techniques, where for example, the nucleotides or oligonucleotides used to extend the primer are modified such that they will chemically react to extend the primer in a sequence specific manner. Typically the disclosed primers hybridize with the disclosed nucleic acids or region of the nucleic acids or they hybridize with the complement of the nucleic acids or complement of a region of the nucleic acids.

The size of the primers or probes for interaction with the nucleic acids in certain embodiments can be any size that supports the desired enzymatic manipulation of the primer, such as DNA amplification or the simple hybridization of the probe or primer. A typical primer or probe would be at least 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments a primer or probe can be less than or equal to 6, 7, 8, 9, 10, 11, 12 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In certain embodiments this product is at least 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

In other embodiments the product is less than or equal to 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 125, 150, 175, 200, 225, 250, 275, 300, 325, 350, 375, 400, 425, 450, 475, 500, 550, 600, 650, 700, 750, 800, 850, 900, 950, 1000, 1250, 1500, 1750, 2000, 2250, 2500, 2750, 3000, 3500, or 4000 nucleotides long.

d) Functional Nucleic Acids

Functional nucleic acids are nucleic acid molecules that have a specific function, such as binding a target molecule or catalyzing a specific reaction. Functional nucleic acid molecules can be divided into the following categories, which are not meant to be limiting. For example, functional nucleic acids include antisense molecules, aptamers, ribozymes, triplex forming molecules, and external guide sequences. The functional nucleic acid molecules can act as affectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA of DMPK or ClC1. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. Numerous methods for optimization of antisense efficiency by finding the most accessible regions of the target molecule exist. Exemplary methods would be in vitro selection experiments and DNA modification studies using DMS and DEPC. It is preferred that antisense molecules bind the target molecule with a dissociation constant ($k_d$) less than or equal to $10^{-6}$, $10^{-8}$, $10^{-10}$, or $10^{-12}$. A representative sample of methods and techniques which aid in the design and use of antisense molecules can be found in the following non-limiting list of U.S. Pat. Nos. 5,135,917, 5,294,533, 5,627,158, 5,641,754, 5,691,317, 5,780,607, 5,786,138, 5,849,903, 5,856,103, 5,919,772, 5,955,590, 5,990,088, 5,994,320, 5,998,602, 6,005,095, 6,007,995, 6,013,522, 6,017,898, 6,018,042, 6,025,198, 6,033,910, 6,040,296, 6,046,004, 6,046,319, and 6,057,437.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP (U.S. Pat. No. 5,631,146) and theophiline (U.S. Pat. No. 5,580,737), as well as large molecules, such as reverse transcriptase (U.S. Pat. No. 5,786,462) and thrombin (U.S. Pat. No. 5,543,293). Aptamers can bind very tightly with $k_d$s from the target molecule of less than $10^{-12}$ M. It is preferred that the aptamers bind the target molecule with a $k_d$ less than $10^{-6}$, $10^{-8}$, $10^{-10}$, or $10^{-12}$. Aptamers can bind the target molecule with a very high degree of specificity. For example, aptamers have been isolated that have greater than a 10000 fold difference in binding affinities between the target molecule and another molecule that differ at only a single position on the molecule (U.S. Pat. No. 5,543,293). It is preferred that the aptamer have a $k_d$ with the target molecule at least 10, 100, 1000, 10,000, or 100,000 fold lower than the $k_d$ with a background binding molecule. It is preferred when doing the comparison for a polypeptide for example, that the background molecule be a different polypeptide. Representative examples of how to make and use aptamers to bind a variety of different target molecules can be found in the following non-limiting list of U.S. Pat. Nos. 5,476,766, 5,503,978, 5,631,146, 5,731,424, 5,780,228, 5,792,613, 5,795,721, 5,846,713, 5,858,660, 5,861,254, 5,864,026, 5,869,641, 5,958,691, 6,001,988, 6,011,020, 6,013,443, 6,020,130, 6,028,186, 6,030,776, and 6,051,698.

Ribozymes are nucleic acid molecules that are capable of catalyzing a chemical reaction, either intramolecularly or intermolecularly. Ribozymes are thus catalytic nucleic acid. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes, (for example, but not limited to the following U.S. Pat. Nos. 5,334,711, 5,436,330, 5,616,466, 5,633,133, 5,646,020, 5,652,094, 5,712,384, 5,770,715, 5,856,463, 5,861,288, 5,891,683, 5,891,684, 5,985,621, 5,989,908, 5,998,193, 5,998,203, WO 9858058 by Ludwig and Sproat, WO 9858057 by Ludwig and Sproat, and WO 9718312 by Ludwig and Sproat) hairpin ribozymes (for example, but not limited to the following U.S. Pat. Nos. 5,631,115, 5,646,031, 5,683,902, 5,712,384, 5,856,188, 5,866,701, 5,869,339, and 6,022,962), and tetrahymena ribozymes (for example, but not limited to the following U.S. Pat. Nos. 5,595,873 and 5,652,107). There are also a number of ribozymes that are not found in natural systems, but which have been engineered to catalyze specific reactions de novo (for example, but not limited to the following U.S. Pat. Nos. 5,580,967, 5,688,670, 5,807,718, and 5,910,408). Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence. Representative examples of how to make and use ribozymes to catalyze a variety of different reactions can be found in the following non-limiting list of U.S. Pat. Nos. 5,646,042, 5,693,535, 5,731,295, 5,811,300, 5,837,855, 5,869,253, 5,877,021, 5,877,022, 5,972,699, 5,972,704, 5,989,906, and 6,017,756.

Triplex forming functional nucleic acid molecules are molecules that can interact with either double-stranded or single-stranded nucleic acid. When triplex molecules interact with a target region, a structure called a triplex is formed, in which there are three strands of DNA forming a complex dependant on both Watson-Crick and Hoogsteen base-pairing. Triplex molecules are preferred because they can bind target regions with high affinity and specificity. It is preferred that the triplex forming molecules bind the target molecule with a $k_d$ less than $10^{-6}$, $10^{-8}$, $10^{-10}$, or $10^{-12}$. Representative examples of how to make and use triplex forming molecules to bind a variety of different target molecules can be found in the following non-limiting list of U.S. Pat. Nos. 5,176,996, 5,645,985, 5,650,316, 5,683,874, 5,693,773, 5,834,185, 5,869,246, 5,874,566, and 5,962,426.

External guide sequences (EGSs) are molecules that bind a target nucleic acid molecule forming a complex, and this complex is recognized by RNase P, which cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. (WO 92/03566 by Yale, and Forster and Altman, *Science* 238:407-409 (1990)).

Similarly, eukaryotic EGS/RNAse P-directed cleavage of RNA can be utilized to cleave desired targets within eukarotic cells. (Yuan et al., *Proc. Natl. Acad. Sci. USA* 89:8006-8010 (1992); WO 93/22434 by Yale; WO 95/24489 by Yale; Yuan and Altman, *EMBO J* 14:159-168 (1995), and Carrara et al., *Proc. Natl. Acad. Sci.* (*USA*) 92:2627-2631 (1995)). Representative examples of how to make and use EGS molecules to facilitate cleavage of a variety of different target molecules be found in the following non-limiting list of U.S. Pat. Nos. 5,168,053, 5,624,824, 5,683,873, 5,728,521, 5,869,248, and 5,877,162.

4. Peptides
a) Protein Variants

As discussed herein there are numerous variants of the MBNL1 protein and that are known and herein contemplated. In addition, to the known functional MBNL1 strain variants there are derivatives of the MBNL1 proteins which also function in the disclosed methods and compositions. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Immunogenic fusion protein derivatives, such as those described in the examples, are made by fusing a polypeptide sufficiently large to confer immunogenicity to the target sequence by cross-linking in vitro or by recombinant cell culture transformed with DNA encoding the fusion. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | AlaA |
| allosoleucine | AIle |
| arginine | ArgR |
| asparagine | AsnN |
| aspartic acid | AspD |
| cysteine | CysC |
| glutamic acid | GluE |
| glutamine | GlnK |
| glycine | GlyG |
| histidine | HisH |
| isolelucine | IleI |
| leucine | LeuL |
| lysine | LysK |
| phenylalanine | PheF |
| proline | ProP |
| pyroglutamic acid | pGlu |

TABLE 1-continued

Amino Acid Abbreviations

| Amino Acid | Abbreviations |
|---|---|
| serine | SerS |
| threonine | ThrT |
| tyrosine | TyrY |
| tryptophan | TrpW |
| valine | ValV |

TABLE 2

Amino Acid Substitutions
Original Residue Exemplary Conservative
Substitutions, others are known in the art.

Ala ser
Arg lys, gln
Asn gln; his
Asp glu
Cys ser
Gln asn, lys
Glu asp
Gly pro
His asn; gln
Ile leu; val
Leu ile; val
Lys arg; gln;
Met Leu; ile
Phe met; leu; tyr
Ser thr
Thr ser
Trp tyr
Tyr trp; phe
Val ile; leu Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. The substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the mosaic polypeptides provided herein.

Substitutional or deletional mutagenesis can be employed to insert sites for N-glycosylation (Asn-X-Thr/Ser) or O-glycosylation (Ser or Thr). Deletions of cysteine or other labile residues also may be desirable. Deletions or substitutions of potential proteolysis sites, e.g. Arg, is accomplished for example by deleting one of the basic residues or substituting one by glutaminyl or histidyl residues.

Certain post-translational derivatizations are the result of the action of recombinant host cells on the expressed polypeptide. Glutaminyl and asparaginyl residues are frequently post-translationally deamidated to the corresponding glutamyl and asparyl residues. Alternatively, these residues are deamidated under mildly acidic conditions. Other post-translational modifications include hydroxylation of proline and lysine, phosphorylation of hydroxyl groups of seryl or threonyl residues, methylation of the o-amino groups of lysine, arginine, and histidine side chains (T. E. Creighton, *Proteins: Structure and Molecular Properties*, W. H. Freeman & Co., San Francisco pp 79-86 [1983]), acetylation of the N-terminal amine and, in some instances, amidation of the C-terminal carboxyl.

It is understood that one way to define the variants and derivatives of the disclosed proteins herein is through defining the variants and derivatives in terms of homology/identity to specific known sequences. For example, SEQ ID NO:1 sets forth a particular sequence of MBNL1 and SEQ ID NO:2 sets forth a particular sequence of a MBNL1 protein. Specifically disclosed are variants of these and other proteins herein disclosed which have at least, 70% or 75% or 80% or 85% or 90% or 95% homology to the stated sequence. Those of skill in the art readily understand how to determine the homology of two proteins. For example, the homology can be calculated after aligning the two sequences so that the homology is at its highest level.

Another way of calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, *J. Mol. Biol.* 48: 443 (1970), by the search for similarity method of Pearson and Lipman, *Proc. Natl. Acad. Sci. U.S.A.* 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection.

The same types of homology can be obtained for nucleic acids by for example the algorithms disclosed in Zuker, M. *Science* 244:48-52, 1989, Jaeger et al. *Proc. Natl. Acad. Sci. USA* 86:7706-7710, 1989, Jaeger et al. *Methods Enzymol.* 183:281-306, 1989 which are herein incorporated by reference for at least material related to nucleic acid alignment.

It is understood that the description of conservative mutations and homology can be combined together in any combination, such as embodiments that have at least 70% homology to a particular sequence wherein the variants are conservative mutations.

As this specification discusses various proteins and protein sequences it is understood that the nucleic acids that can encode those protein sequences are also disclosed. This would include all degenerate sequences related to a specific protein sequence, i.e. all nucleic acids having a sequence that encodes one particular protein sequence as well as all nucleic acids, including degenerate nucleic acids, encoding the disclosed variants and derivatives of the protein sequences. Thus, while each particular nucleic acid sequence may not be written out herein, it is understood that each and every sequence is in fact disclosed and described herein through the disclosed protein sequence. For example, one of the many nucleic acid sequences that can encode the protein sequence set forth in SEQ ID NO:1 is set forth in SEQ ID NO:2. It is understood that while no amino acid sequence indicates what particular DNA sequence encodes that protein within an organism, where particular variants of a disclosed protein are disclosed herein, the known nucleic acid sequence that encodes that protein from which that protein arises is also known and herein disclosed and described.

It is understood that there are numerous amino acid and peptide analogs which can be incorporated into the disclosed compositions. For example, there are numerous D amino acids or amino acids which have a different functional substituent then the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., *Methods in Molec. Biol.* 77:43-73 (1991), Zoller, *Current Opinion in Biotechnology*, 3:348-354 (1992); Ibba, *Biotechnology & Genetic Enginerring Reviews* 13:197-216 (1995), Cahill et al., *TIBS*, 14(10):400-403 (1989); Benner, *TIB Tech*, 12:158-163 (1994); Ibba and Hennecke, *Biotechnology*, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH=CH— (cis and trans), —$COCH_2$—, —CH(OH)$CH_2$—, and —$CHH_2SO$— (These and others can be found in Spatola, A. F. in *Chemistry and Biochemistry of Amino Acids, Peptides, and Proteins*, B. Weinstein, eds., Marcel Dekker, New York, p. 267 (1983); Spatola, A. F., Vega Data (March 1983), Vol. 1, Issue 3, Peptide Backbone Modifications (general review); Morley, *Trends Pharm Sci* (1980) pp. 463-468; Hudson, D. et al., *Int J Pept Prot Res* 14:177-185 (1979) (—$CH_2NH$—, $CH_2CH_2$—); Spatola et al. *Life Sci* 38:1243-1249 (1986) (—$CHH_2$—S); Hann *J. Chem. Soc Perkin Trans.* I 307-314 (1982) (—CH=CH—, cis and trans); Almquist et al. *J. Med. Chem.* 23:1392-1398 (1980) (—$COCH_2$—); Jennings-White et al. *Tetrahedron Lett* 23:2533 (1982) (—$COCH_2$—); Szelke et al. European Appln, EP 45665 CA (1982): 97:39405 (1982) (—CH(OH)$CH_2$—); Holladay et al. *Tetrahedron. Lett* 24:4401-4404 (1983) (—C(OH)$CH_2$—); and Hruby *Life Sci* 31:189-199 (1982) (—$CH_2$—S—); each of which is incorporated herein by reference. A particularly preferred non-peptide linkage is —$CH_2NH$—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch *Ann. Rev. Biochem.* 61:387 (1992), incorporated herein by reference).

5. Pharmaceutical Carriers/Delivery of Pharmaceutical Products

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer,* 60:275-281, (1989); Bagshawe, et al., *Br. J. Cancer,* 58:700-703, (1988); Senter, et al., *Bioconjugate Chem.*, 4:3-9, (1993); Battelli, et al., *Cancer Immunol. Immunother.,* 35:421-425, (1992); Pietersz and McKenzie, *Immunolog. Reviews,* 129: 57-80, (1992); and Roffler, et al., *Biochem. Pharmacol,* 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research,* 49:6214-6220, (1989); and Litzinger and Huang, *Biochimica et Biophysica Acta,* 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

a) Pharmaceutically Acceptable Carriers

The compositions, including antibodies, can be used therapeutically in combination with a pharmaceutically acceptable carrier.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

b) Therapeutic Uses

Effective dosages and schedules for administering the compositions may be determined empirically, and making such determinations is within the skill in the art. The dosage ranges for the administration of the compositions are those large enough to produce the desired effect in which the symptoms/disorder are/is effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

Following administration of a disclosed composition, such as an antisense oligonucleotide morpholino or PNA, for treating, inhibiting, or preventing an DM1, the efficacy of the therapeutic antibody can be assessed in various ways well known to the skilled practitioner. For instance, one of ordinary skill in the art will understand that a composition, such as a morpholino, disclosed herein is efficacious in treating or inhibiting a DM1 in a subject by observing that the composition reduces symptoms associated with the disease or reduces nuclear foci sequestration of MBNL1.

The compositions that inhibit MBNL1 interactions with poly(CUG)$^{exp}$ disclosed herein may be administered prophylactically to patients or subjects who are at risk for DM1.

6. Compositions Identified by Screening with Disclosed Compositions/Combinatorial Chemistry a) Combinatorial Chemistry The disclosed compositions can be used as targets for any combinatorial technique to identify molecules or macromolecular molecules that interact with the disclosed compositions in a desired way. It is understood that when using the disclosed compositions in combinatorial techniques or screening methods, molecules, such as macromolecular molecules, will be identified that have particular desired properties such as inhibition or stimulation or the target molecule's function. The molecules identified and isolated when using the disclosed methods, such as, CAG25, are also disclosed.

It is understood that the disclosed methods for identifying molecules that inhibit the interactions between, for example, MBNL1 and poly(CUG)$^{exp}$ can be performed using high through put means. For example, putative inhibitors can be identified using Fluorescence Resonance Energy Transfer (FRET) to quickly identify interactions. The underlying theory of the techniques is that when two molecules are close in space, ie, interacting at a level beyond background, a signal is produced or a signal can be quenched. Then, a variety of experiments can be performed, including, for example, adding in a putative inhibitor. If the inhibitor competes with the interaction between the two signaling molecules, the signals will be removed from each other in space, and this will cause a decrease or an increase in the signal, depending on the type of signal used. This decrease or increasing signal can be correlated to the presence or absence of the putative inhibitor. Any signaling means can be used. For example, disclosed are methods of identifying an inhibitor of the interaction between any two of the disclosed molecules comprising, contacting a first molecule and a second molecule together in the presence of a putative inhibitor, wherein the first molecule or second molecule comprises a fluorescence donor, wherein the first or second molecule, typically the molecule not comprising the donor, comprises a fluorescence acceptor; and measuring Fluorescence Resonance Energy Transfer (FRET), in the presence of the putative inhibitor and the in absence of the putative inhibitor, wherein a decrease in FRET in the presence of the putative inhibitor as compared to FRET measurement in its absence indicates the putative inhibitor inhibits binding between the two molecules. This type of method can be performed with a cell system as well.

Combinatorial chemistry includes but is not limited to all methods for isolating small molecules or macromolecules that are capable of binding either a small molecule or another macromolecule, typically in an iterative process. Proteins, oligonucleotides, and sugars are examples of macromolecules. For example, oligonucleotide molecules with a given function, catalytic or ligand-binding, can be isolated from a complex mixture of random oligonucleotides in what has been referred to as "in vitro genetics" (Szostak, *TIBS* 19:89, 1992). One synthesizes a large pool of molecules bearing random and defined sequences and subjects that complex mixture, for example, approximately $10^{15}$ individual sequences in 100 µg of a 100 nucleotide RNA, to some selection and enrichment process. Through repeated cycles of affinity chromatography and PCR amplification of the molecules bound to the ligand on the column, Ellington and Szostak (1990) estimated that 1 in $10^{10}$ RNA molecules folded in such a way as to bind a small molecule dyes. DNA molecules with such ligand-binding behavior have been isolated as well (Ellington and Szostak, 1992; Bock et al, 1992). Techniques aimed at similar goals exist for small organic molecules, proteins, antibodies and other macromolecules known to those of skill in the art. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have de novo activity or a modified activity. For example, phage display libraries have been used to isolate numerous peptides that interact with a specific target. (See for example, U.S. Pat. Nos. 6,031,071; 5,824,520; 5,596,079; and 5,565,332 which are herein incorporated by reference at least for their material related to phage display and methods relate to combinatorial chemistry)

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptdyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selection techniques. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. *Proc. Natl. Acad. Sci. USA,* 94(23) 12997-302 (1997)).

Another preferred method for combinatorial methods designed to isolate peptides is described in Cohen et al. (Cohen B. A., et al., *Proc. Natl. Acad. Sci. USA* 95(24):14272-7 (1998)). This method utilizes and modifies two-hybrid technology. Yeast two-hybrid systems are useful for the detection and analysis of protein:protein interactions. The two-hybrid system, initially described in the yeast *Saccharomyces cerevisiae*, is a powerful molecular genetic technique for identifying new regulatory molecules, specific to the protein of interest (Fields and Song, *Nature* 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain.

Using methodology well known to those of skill in the art, in combination with various combinatorial libraries, one can isolate and characterize those small molecules or macromolecules, which bind to or interact with the desired target. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449, 754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972, 719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916, 899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856, 107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits (U.S. Pat. Nos. 5,698,685 and 5,506,337), sulfamides (U.S. Pat. No. 5,618,825), and benzodiazepines (U.S. Pat. No. 5,288,514).

As used herein combinatorial methods and libraries included traditional screening methods and libraries as well as methods and libraries used in interative processes.

7. Compositions with Similar Functions

It is understood that the compositions disclosed herein have certain functions, such as displacing MBNL1 or binding polyCUG$^{exp}$ mRNA. Disclosed herein are certain structural requirements for performing the disclosed functions, and it is understood that there are a variety of structures which can perform the same function which are related to the disclosed structures, and that these structures will ultimately achieve the same result, for example inhibition of the interaction between MBNL1 and polyCUG$^{exp}$ mRNA.

Throughout this application, various publications are referenced. The disclosures of these publications in their entireties are hereby incorporated by reference into this application in order to more fully describe the state of the art to which this invention pertains. The references disclosed are also individually and specifically incorporated by reference herein for the material contained in them that is discussed in the sentence in which the reference is relied upon.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

D. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Example 1

MBNL Sequestration on Poly(CUG)$^{exp}$ Leading to Spliceopathy

Transcription of the mutant allele generates DMPK mRNA containing an expanded CUG repeat. Mutant transcripts accumulate in discrete RNA nuclear (ribonuclear) foci. The RNA in foci is the fully-processed DMPK mRNA (Taneja K L, et al. J Cell Biol 1995; 128(6):995-1002). Reddy and colleagues have found that siRNA-mediated depletion of MBNL1 eliminated most of the ribonuclear foci in DM1 myoblasts, suggesting that the MBNL1-poly(CUG)$^{exp}$ interaction is the key determinant of foci formation (Dansithong W, et al. J Biol Chem 2005; 280(7):5773-5780). RNA binding proteins in the muscleblind-like (MBNL) family, including MBNL1, MBNL2, and MBNL3, are sequestered in ribonuclear foci. MBNL proteins show strong colocalization with poly(CUG)$^{exp}$ in DM1 cells and consequently are depleted from the nucleoplasm (Lin X, et al. Hum Mol Genet 2006; Mankodi A, et al. Hum Mol Genet 2001; 10:2165-2170). MBNL1 and MBNL2 are expressed in mature skeletal muscle, heart and brain (Fardaei M, et al. Hum Mol Genet 2002; 11(7):805-814; Kanadia R N, et al. Gene Expr Patterns 2003; 3(4):459-462). MBNL3 is expressed mainly in placenta. Loss of MBNL1 function leads to abnormal regulation of alternative splicing for a select group of pre-mRNAs, such as, insulin receptor and chloride channel 1. When overexpressed, all three MBNL family members can regulate splicing (Ho T H, et al. EMBO J 2004; 23(15):3103-3112). Other splicing factors, such as, CUG-BP1 may contribute to spliceopathy in DM1 (Savkur R S, et al. Nat Genet 2001; 29(1):40-47; Philips A V, et al. Science 1998; 280(5364):737-741), although they are not sequestered in nuclear foci of poly (CUG)$^{exp}$. Expression of splice isoforms that are developmentally inappropriate leads to signs and symptoms of DM1, such as, insulin resistance and myotonia.

2. Example 2

Mouse Models of DM1

HSA$^{LR}$ transgenic mice express human skeletal actin mRNA containing (CUG)$^{250}$ in the 3' UTR. These mice express high levels of poly(CUG)$^{exp}$ exclusively in skeletal muscle, and they develop myotonic myopathy[9] (see below). Mbnl1$^{ΔE3/ΔE3}$ mice (derived in the Swanson lab) are homozygous for a targeted allele of Mbnl1. These mice develop myotonic myopathy but the myopathy appears less severe that in HSA$^{LR}$ mice[5]. Mbnl1 knockout mice also develop multisystemic features of DM1, such as, cataracts, progressive (ultimately fatal) cardiac disease, and abnormal CNS function.

3. Example 3

Structure of Poly(CUG)$^{exp}$ and Binding to MBNL1

Poly(CUG) RNA forms stable hairpin structures in vitro when it is pathologically expanded (Napierala M, Krzyzosiak W J. J Biol Chem 1997; 272(49):31079-31085; Tian B, et al. Rna 2000; 6:79-87). The stem of the hairpin is an extended region of duplex RNA in which G•C and C•G base pairs are separated by a periodic U•U mismatch. MBNL1 binds to poly(CUG)$^{exp}$ in vitro in preference to poly(CUG) that is not expanded, suggesting that it recognizes poly(CUG) in a structured (duplex) form (Miller J W, et al. EMBO J 2000; 19(17): 4439-4448). By comparison, the physiologic targets for splicing regulation by MBNL1 are short, 6-8 nt intronic splice enhancer/repressor elements.

4. Example 4

Progressive Myotonic Myopathy (PMM): A Composite Phenotype

The PMM in DM1 is distinct from muscle phenotypes in other forms of dystrophy. PMM is a composite, additive phenotype resulting from independent effects of spliceopathy on different genes, and consequently, different pathways.

a) Myotonia

Myotonia is a delay of muscle relaxation after voluntary contraction, caused by runs of action potentials that are generated in the muscle fibers. In HSA$^{LR}$ transgenic mice, myotonia is associated with abnormal regulation of alternative splicing for the ClC-1 chloride channel and >70% reduction of the sarcolemmal Cl conductance (Mankodi A, et al. Mol Cell 2002; 35-44). A parallel abnormality of ClC-1 splicing and loss of ClC-1 protein occurs in human DM1 and DM2. As further evidence that myotonia in DM1 is a chloride channelopathy stemming from effects on splicing of ClC-1, the reversal of ClC-1 spliceopathy, either by antisense oligonucleotides that suppress splicing of misregulated exon, or by AAV-mediated overexpression of MBNL1, lead to resolution of myotonia in HSA$^{LR}$ mice (M Swanson, R Kanadia, T Wheeler, C Thornton, unpublished). While medications provide partial relief of myotonia, they are not very effective when myotonia is severe, hence they are not widely prescribed. Because the myotonia is most severe in hand muscles that also are hampered by early weakness, it markedly interferes with manual dexterity and contributes to disability. Furthermore, a clear correlation between severity of myotonia and weakness in DM1 exists, indicating that calcium and mechanical overload due to myotonic discharges can accelerate the myopathy.

b) Insulin Resistance.

DM1 is characterized by insulin resistance in skeletal muscle. Cooper and colleagues have shown that spliceopathy affects alternative splicing of insulin receptor (Savkur R S, et al. Nat Genet 2001; 29(1):40-47) (INSR). The predominant INSR isoform expressed in DM1 muscle is the exon 11 skipped, non-muscle isoform, which has lower signaling capacity. Because hybrid IGF-1/insulin receptors form in skeletal muscle, the INSR spliceopathy may also influence IGF-1 signaling.

c) Myopathy

Several factors can contribute the pathogenesis of myopathy in DM1: (1) simple atrophy due to reduced anabolic influence, such as, reduced signaling through insulin and IGF-1 receptors; (2) structural abnormalities, such as, abnormal cytoskeletal organization that is observed in DM1 muscle fibers; (3) abnormal nuclear function, as reflected by an increase in the number of muscle nuclei per fiber (the earliest histologic change in DM1); (4) ineffective regeneration/repair, as reflected by abnormal myogenesis that characterizes the most severe, congenital form of DM1; (5) reduced nerve-muscle trophic support, as reflected by denervation-like changes (pyknotic nuclear clumps, angular atrophic fibers) in muscle fibers and expanded terminal arborizations and axonal proliferation in intramuscular nerves; and (6) calcium overload due to myotonia.

5. Example 5

MBNL1 Sequestration: Pivotal Role in Muscle Spliceopathy

Spliceopathy in DM1 targets a select group of pre-mRNAs that share a common temporal pattern of developmental regulation (Lin X, et al. Hum Mol Genet 2006). The exons affected by spliceopathy normally undergo a synchronous splicing switch during early postnatal development in WT mice. However, loss of MBNL1, or expression of poly(CUG)$^{exp}$, results in identical failure of these splicing transitions. The spliceopathies in $HSA^{LR}$ transgenic mice, MBNL1 knockout mice, and human DM1 and DM2 are highly concordant. Immunofluorescence examination of DM1 and DM2 muscle sections shows that MBNL1 is recruited into ribonuclear foci to such an extent that it is markedly depleted elsewhere in the nucleoplasm (Lin X, et al. *Hum Mol Genet* 2006). Taken together, these results indicate that MBNL1 has a pivotal role in the pathogenesis of spliceopathy. Furthermore, phenotypic consequences in mouse models clearly are influenced by the level of poly(CUG)$^{exp}$ in relation to nuclear supplies of MBNL1 protein. For example, in lines of $HSA^{LR}$ transgenic mice that are phenotypically normal and have subthreshold accumulation of poly(CUG)$^{exp}$, crossing with MBNL1 null heterozygotes (lowering MNBL1 protein by 50%) results in spliceopathy, myotonia, and myopathy. Also, intramuscular injection of AAV-MBNL1 expression vector leads to resolution of myotonia and correction of spliceopathy in $HSA^{LR}$ mice.

6. Example 6

Cell-Based Assay for Compounds that Correct Poly(CUG)$^{exp}$-Induced Spliceopathy.

Figure 1D:
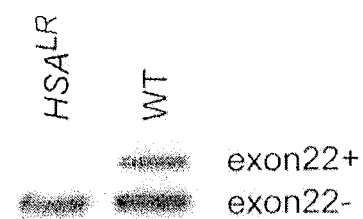
Figure 1B:
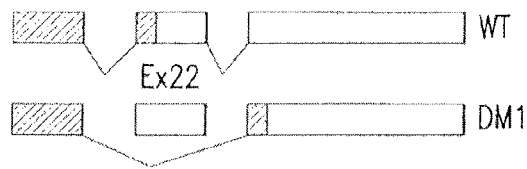
Figure 1C:
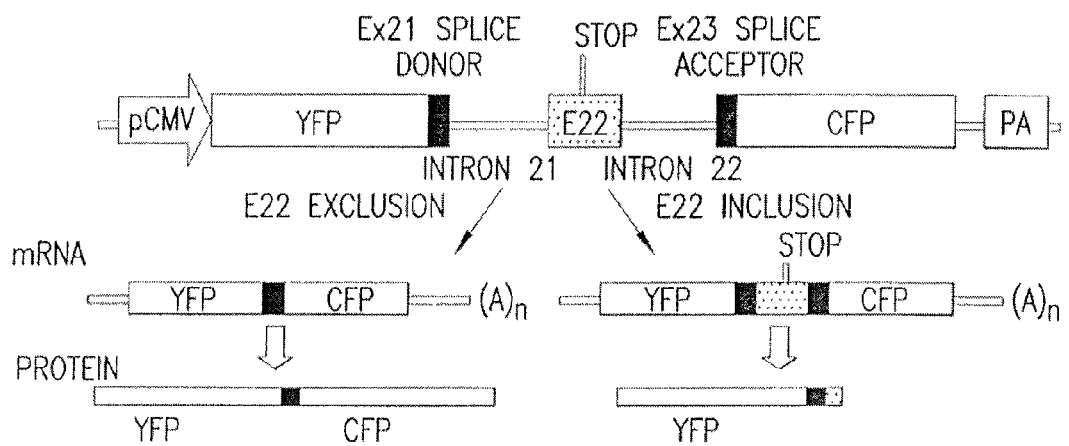

The assay has two components: (1) cells that display poly(CUG)$^{exp}$-induced spliceopathy; and (2) a minigene construct that reports on severity of spliceopathy. To develop the reporter, ~70 alternatively spliced exons were analyzed in $HSA^{LR}$ mouse and DM1 muscle to identify exons most affected by spliceopathy. Out of 16 exons affected by spliceopathy, exon 22 of SERCA1 was one of the most severely affected, and the gene structure of SERCA1 lent itself well to adaptation for the reporter assay. The fraction of SERCA1 mRNA skipping exon 22 increased from 3±0.7% in WT to 78±4% in $HSA^{LR}$ mice, and the proportional change in DM1 and DM2 was similar (Lin X, et al. Hum Mol Genet 2006). SERCA1 exon 22 normally undergoes a postnatal splicing switch in WT muscle, but this switch fails to occur in $HSA^{LR}$ transgenic and MBNL1 knockout mice (FIG. 1A). Exons 22 and 23 contain alternative termination codons for SERCA1 translation (FIG. 1B). A minigene construct, pSERF, was cloned to generate a fluorescence readout for the relative frequencies of exon 22 skipping and inclusion. pSERF contains SERCA1 exon 22 and its flanking introns (FIG. 1C). Splice donor and acceptor signals from the flanking exons are fused to the coding regions for yellow fluorescent protein (eYFP) and cyan fluorescent protein (eCFP). Spectral separation of these proteins is more than sufficient to resolve eYFP and eCFP components when both proteins are co-expressed. Both fluorescent proteins function as monomers and have rapid maturation times. The splicing outcome characteristic of normal mature skeletal muscle is inclusion of exon 22 (FIG. 1A, lane 4). The exon 22 inclusion (ex22+) transcript of pSERF encodes eYFP alone. The splicing that is characteristic of DM1 muscle skips exon 22 (ex22−, FIG. 1A, lanes 5-12). The ex22− transcript encodes eYFP-eCFP fusion protein (Y•CFP). To test that pSERF is properly spliced in WT muscle and misregulated in response to poly(CUG)$^{exp}$, pSERF was electroporated in vivo in WT or $HSA^{LR}$ mice and muscle was harvested for RNA analysis after 4 days. As expected, inclusion of exon 22 was low in $HSA^{LR}$ mice and high in WT muscle (FIG. 1D). These results indicate that pSERF can report on spliceopathy induced by poly(CUG)$^{exp}$.

Disclosed herein, correction of spliceopathy improves the cardinal symptoms of DM1. A spliceopathy assay has several advantages for identifying compounds having therapeutic potential in DM1. Spliceopathy is a downstream consequence of the RNA mediated disease process that is directly pertinent to symptoms of DM1. A spliceopathy screen can capture compounds that act either on the splicing machinery or upstream of RNA processing, having any of the following desirable effects: (1) accelerated degradation of poly(CUG)$^{exp}$ RNA; (2) upregulation of MBNL1 activity (post-transcriptional); (3) release of MBNL1 from sequestration in nuclear foci; and (4) effects on other splicing regulators, such as, CUG-BP1, that improve the splicing defect. In terms of screening for compounds that inhibit recognition of poly(CUG)$^{exp}$ by MBNL1, the spliceopathy assay identifies compounds that differentially inhibit the interaction of MBNL1 with its pathological target, poly(CUG)$^{exp}$ RNA, compared to its physiological target, the splice enhancer element in SERCA1 pre-mRNA. Finally, the variance of assay results is low. The readout is determined by the ratio of two splice products produced from a single transcription unit, rather than absolute levels for either isoform. This design minimizes variance resulting from nonuniform delivery of cell to wells or nonspecific inhibitory effects of compounds on cell metabolism or survival. In RNA-based assays of alternative splicing, the coefficient of variation for relative proportion of two alternative splice products is usually <3%, lower than most measurements of gene expression. The readout for the assays disclosed herein are at least this low because direct fluorescence determination of pSERF protein products can be reasonably precise.

a) Overview

Figure 6:
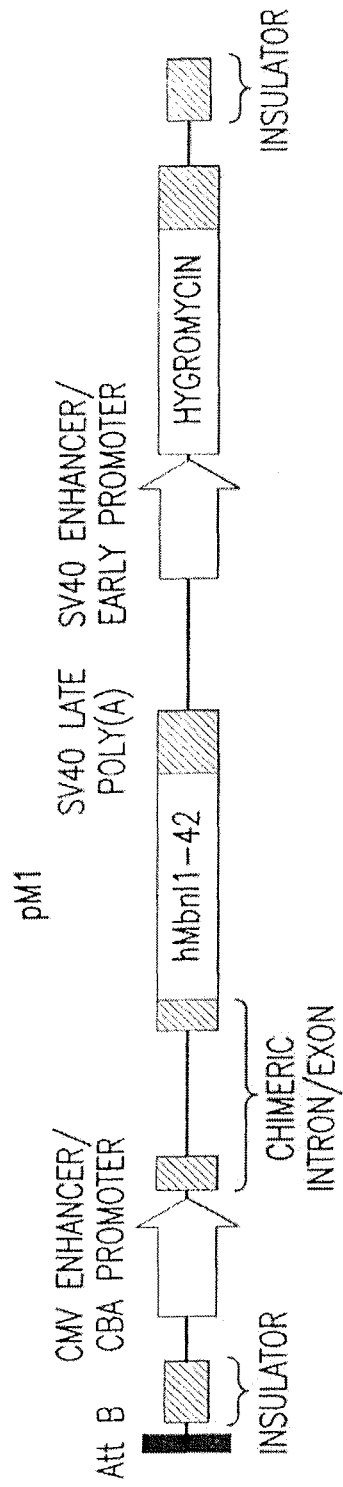
FIG. 6. The transcription unit for MBNL1 is flanked by insulators from the chicken β-globin locus. These elements have been shown to insulate transgene expression from adjacent chromatin context, improving the uniformity of transgene expression (Chung J H, et al. Proc Natl Acad Sci USA 1997; 94(2):575-580). The attB element directs integration by phiC31 integrase. CBA, chicken β actin. Due to the presence of several monospecific antibodies to Mbnl1, there was no need for a reporter gene or epitope tag to monitor expression levels.

Cell lines that overexpress MBNL1 and poly(CUG)$^{exp}$ can be obtained in sequential steps of stable transfection, first to overexpress MBNL1, then to express poly(CUG)$^{exp}$. In both cases, gene transfer is assisted by integrase from bacteriophage phiC31 to obtain full-length, single-copy transgene integrations. Stepwise introduction of MBNL1 and poly(CUG)$^{exp}$ constructs provides more flexibility in choosing optimal ratios of MBNL1 and poly(CUG)$^{exp}$ expression in cells. Spliceopathy is quantified at each step by transient transfection with reporter construct, pSERF. The order of procedures is:

1. Stably transfect cells with MBNL1 expression construct, pM1 (FIG. 6). Test splicing in these lines by transient transfection with pSERF. Select lines that have high YFP to Y•CFP ratio and strong inclusion of exon 22.

Figure 7:
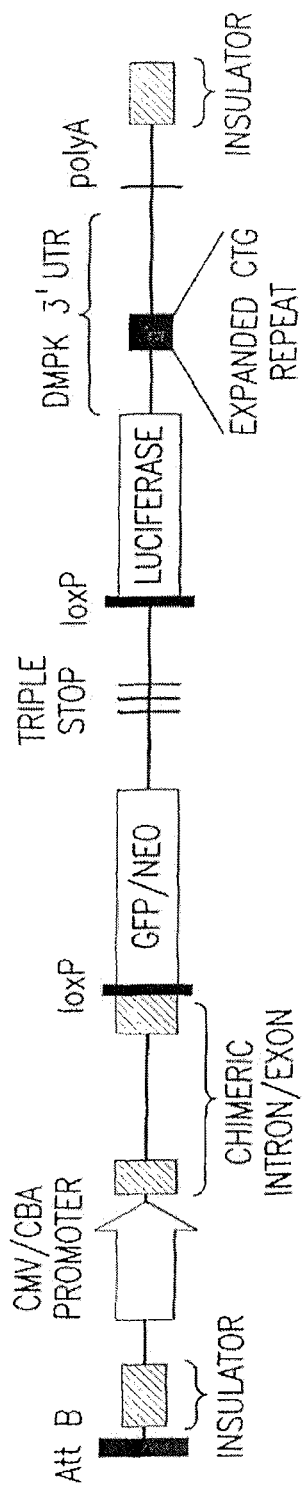
FIG. 7. pLLC7. CMV/CβA, CMV enhancer coupled to chicken beta actin promoter; triple stop, concatamer of three SV40 polyadenylation signals and transcription terminator elements (Novak A, et al. Genesis 2000; 28(3-4):147-155); GFP/NEO, Bizyme neomycin resistance-GFP fluorescence selection cassette (Hansen S G, et al. Biotechniques 2002; 32(5):1178, 1180, 1182-1178); AttB, integration signal for phiC31 integrase.

2. Stably transfect with poly(CUG)$^{exp}$ expression construct, pLLC7 (FIG. 7). Select cell lines that show uniform expression of the GFP-neomycin resistance cassette.

3. Excise the GFP-neomycin resistance cassette in LLC7 transgene using cre recombinase. Verify that recombination has activated expression of poly(CUG)$^{exp}$, and that cells develop nuclear foci of poly(CUG)$^{exp}$.

4. Test splicing by transient transfection with pSERF. Select lines that have low YFP to Y•CFP ratio and strong exclusion of SERCA1 exon 22 (i.e., the pattern of splicing that is characteristic of DM1 muscle).

b) Stably Transfect Cell Lines to Overexpress MBNL1 and Obtain "Muscle-Like" Splicing Outcomes.

Figure 5:
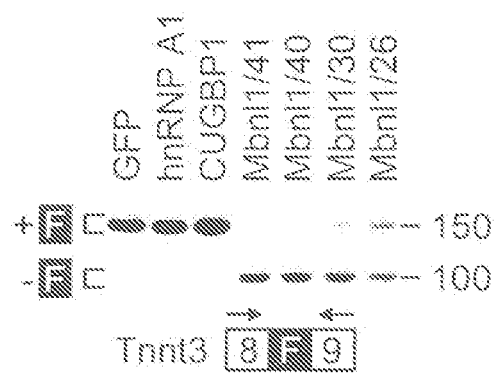
FIG. 5. Transfection with MBNL1, but not other RNA binding proteins, drives splicing of TNNT3 from the DM1/fetal pattern to the mature muscle (fetal exon exclusion, 100 bp) pattern.
Figure 13:
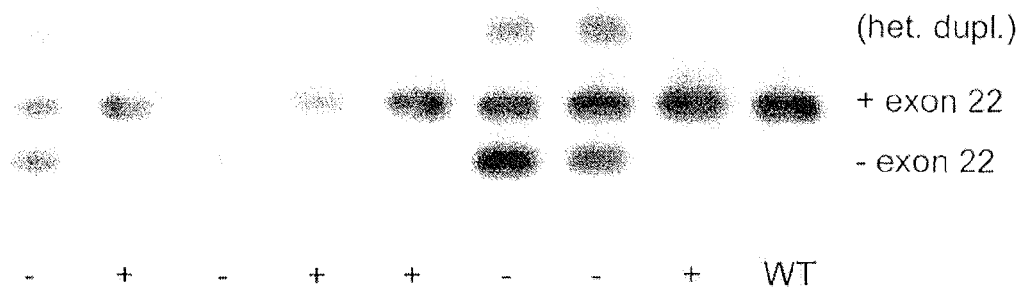
FIG. 13 shows the release of MBNL1 from ribonuclear foci following treatment with CAG25 morpholino restored proper regulation of alternative splicing for SERCA1 (3 weeks following CAG25 injection). In 4 different $HSA^{LR}$ transgenic mice, injection of CAG25 morpholino into tibialis anterior improved the defect of SERCA1 alternative splicing. Morpholino-treated muscle is indicated by "+". Results from tibialis anterior in the opposite hindlimb, injected with saline alone, are indicated by "−". The side of morpholino injection was randomly determined, and this assignment remained blinded until after the splicing analysis was completed. Het. dupl. indicates a heteroduplex PCR product.
Figure 14:
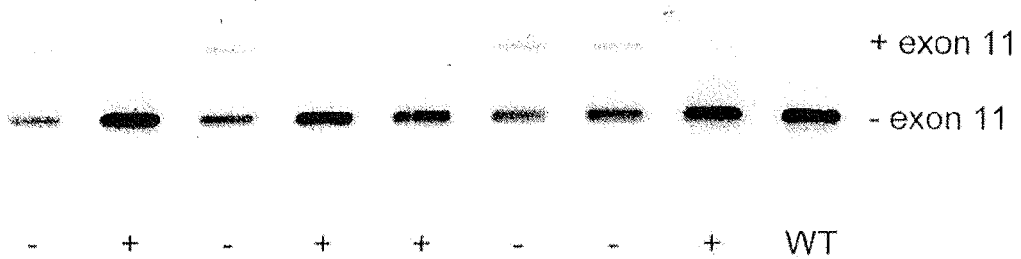
FIG. 14 shows the release of MBNL1 from ribonuclear foci following treatment with CAG25 morpholino improved regulation of alternative splicing for ZASP (n=4 different $HSA^{LR}$ transgenic mice, 3 weeks following CAG25 injection). Morpholino-treated muscle is indicated by "+". Results from tibialis anterior in the opposite hindlimb, injected with saline alone, are indicated by "−". The side of morpholino injection was randomly determined, and this assignment remained blinded until after the splicing analysis was completed.
Figure 15:
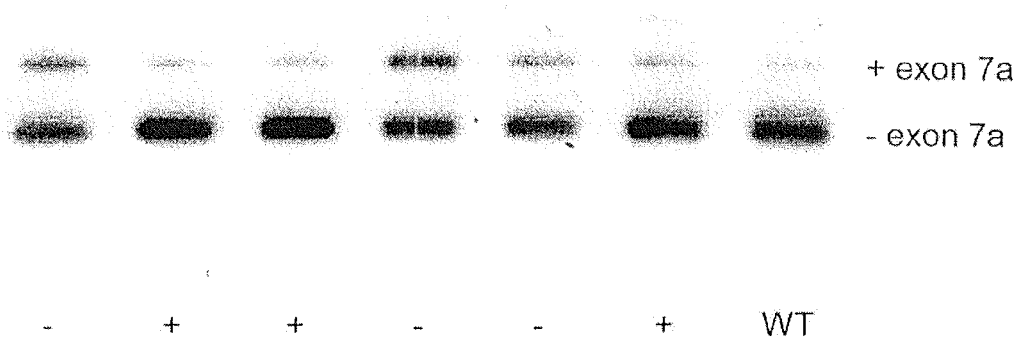
FIG. 15 shows that CAG25 morpholino treatment in $HSA^{LR}$ transgenic mice improved the alternative splicing of ClC-1, the muscle specific chloride ion channel. Exon 7a of ClC-1 shows developmentally regulated alternative splicing, and it was previously shown that MBNL1 is required for its normal regulation (Kanadia et al, Science, 302:1978-1980, 2003). Adult wild-type (WT) mice show low levels of exon 7a inclusion. In $HSA^{LR}$ transgenic mice, the fraction of ClC-1 splice products that include exon 7a is increased. Inclusion of exon 7a causes a frame shift and creates a premature termination codon that truncates most of the ClC-1 coding sequence. Of note, transcripts that include exon 7a have accelerated degradation via nonsense mediated decay, therefore they are underrepresented at steady state and on this gel. The higher bands on the gel are other alternative splice products, as shown (Mankodi et al, Molecular Cell 10:35-44, 2002.) In $HSA^{LR}$ transgenic mice, injection of CAG morpholino into tibialis anterior improved the defect of ClC-1 alternative splicing. Morpholino-treated muscle is indicated by "+". Results from tibialis anterior in the opposite hindlimb, injected with saline alone, are indicated by "−".
Figure 16:
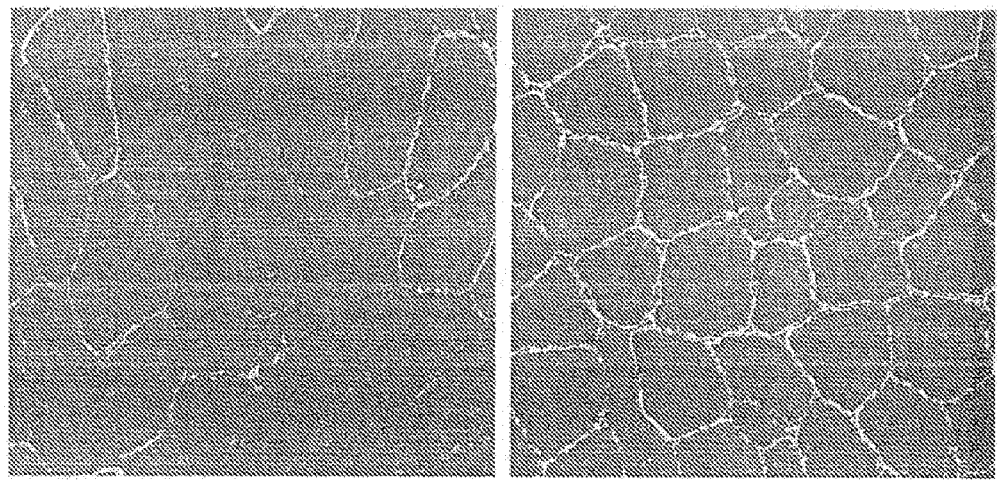
FIG. 16 shows the expression of ClC-1 chloride channel at the surface membrane is increased 3 weeks following injection of CAG25 morpholino. Immunofluorescence for ClC-1 chloride channel is shown in sections of tibialis anterior muscle from $HSA^{LR}$ transgenic mice. Muscle fibers show mosaic expression of ClC-1 in $HSA^{LR}$ muscle injected with saline. Some of these fibers are completely lacking in ClC-1 protein. Treatment with CAG25 morpholino leads to increased expression ClC-1 protein at the surface membrane of muscle fibers.
Figure 17:
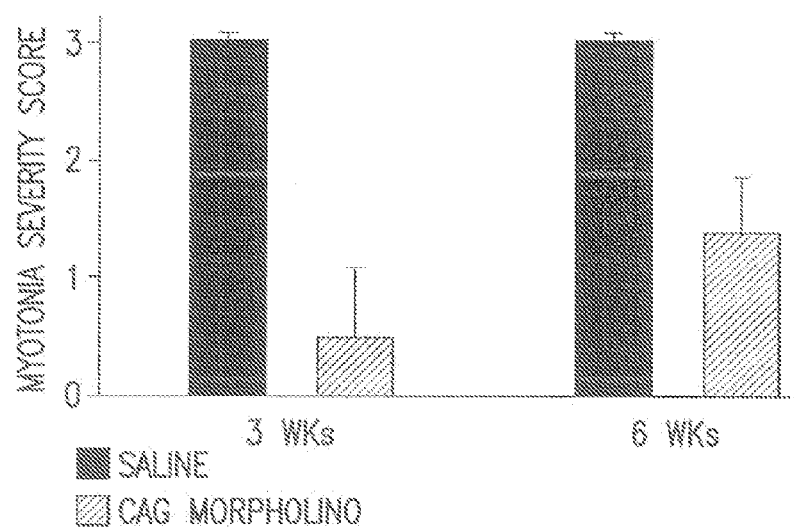
FIG. 17 uses Electromyography to show the improvement of myotonia at 3 and 6 weeks after injection of CAG25 morpholino into tibialis anterior of $HSA^{LR}$ transgenic mice. Myotonia is a state of muscle hyperexcitability in which muscle fibers display repetitive action potentials. Myotonia in the $HSA^{LR}$ transgenic mouse model of myotonic dystrophy is caused by abnormal regulation of alternative splicing for ClC-1 and subsequent reduction of chloride ion channels in muscle fibers. A parallel abnormality of ClC-1 alternative splicing exists in human myotonic dystrophy. In this experiment, the vertical axis shows mean myotonia severity score among 4 $HSA^{LR}$ transgenic mice at each timepoint. For each mouse, CAG25 morpholino dissolved in saline was injected into tibialis anterior muscle of one hindlimb, whereas saline alone was injected into tibialis anterior on the opposite side. The side of morpholino injection was randomly assigned. Electromyography was performed by a blinded examiner Severity of myotonia was graded on a 4 point scale: 0=no myotonic, 1=occasional myotonic discharge (fewer than 25% of needle insertions), 2=abundant myotonic discharges (25-75% of needle insertions), and 3=florid myotonia (myotonic discharges in nearly every needle insertion). Protein displacement therapy with the CAG morpholino resulted in significant reduction of myotonia at 3 and 6 weeks following injection ($p<0.001$ both time points.)

All exons presently known to be affected by spliceopathy require MBNL1 for normal regulation in skeletal muscle and show DM1-like spliceopathy in the absence of MBNL1 (Lin X, et al. Hum Mol Genet 2006). Some of these exons show antagonist regulation by CUG-BP1 and MBNL1: the normal muscle pattern of splicing is promoted by MBNL1, the pattern characteristic of DM1 or non-muscle cells is promoted by CUG-BP1 (Ho T H, et al. EMBO J 2004; 23(15):3103-3112; Philips A V, et al. Science 1998; 280(5364):737-741). The levels of MBNL1 in transformed cell lines are generally low, whereas expression of CUG-BP1 is fairly ubiquitous. As expected, basal splicing outcomes in transformed cell lines are similar to those observed in DM1 (Ho T H, et al. EMBO J 2004; 23(15):3103-3112). However, overexpression of MBNL1 in cells lines is sufficient to drive splicing outcomes to the pattern that is characteristic of normal mature muscle (see FIG. 5 for an example concerning fast troponin T and FIG. 13 for an example concerning SERCA1). Thus, pM1 (FIG. 6) is used to obtain stably transfected cell lines that overexpress MBNL1 and display splicing phenotypes similar to WT skeletal muscle. Initial efforts focus on 293 or COS cells. These adherent, transformed cell lines have previously been used in cell based assays in a 384 well format, and in minigene assays to assess splicing functions of MBNL1. Stable transfection can be assisted by incorporation of attB elements in the plasmid and co-transfection with pCMVInt to express phiC31 integrase. This integrase mediates recombination of plasmids containing the attB element into the mammalian genome. Integration is irreversible and may occur at any of several hundred sites having sequence homology to the bacteriophage attP integration element. Thus, phiC31 can be used for stepwise introduction of constructs into the same cell line. This integrase is effective in cells lines of diverse origin and invariably it leads to single copy integrations of full-length construct (Chalberg T W, et al. J Mol Biol 2006; 357(1):28-48). Integrations tend to occur in regions that are transcriptionally active and supportive of transgene expression (Ishikawa Y, et al. J Gene Med 2006; 8(5):646-653). Stable transfection assisted by phiC31 integrase is fairly efficient.

c) Procedures 293 cells are co-transfected with pM1 and pCMVInt (phiC31 integrase expression construct) using conditions previously defined by Dr Calos (Chalberg T W, et al. J Mol Biol 2006; 357(1):28-48). The ratio of pCMVInt to pM1 is 50:1. Cells are split 1:30 24 hrs after transfection and transferred to hygromycin selection medium the next day. Clones are isolated after 10 to 14 days of selection. Clones are analyzed for: (1) splicing outcome by transfection with pSERF followed by RT-PCR and fluorescence analysis; and (2) MBNL1 overexpression by immunofluorescence and immunoblot. It is herein disclosed that endogenous levels of MBNL1 expression are low and exon 22 inclusion is <5%. An anti-MBNL1 polyclonal antibody A2764 was raised and was shown to be monospecific by immunoblot and immunofluorescence (Lin X, et al. Hum Mol Genet 2006). The optimal cell lines are those showing a high frequency of exon 22 inclusion (high YFP:Y•CFP ratio), increased nuclear MBNL1 that is consistent from cell-to-cell, and an overall increase in MBNL1 protein by immunoblot, compared to untransfected controls.

(1) Stably Transfected Cell Lines that Express Poly(CUG) Exp (a) Uniformity of MBNL1 and Poly(CUG)Exp Expression For a disease state that depends on the stoichiometry of a toxic RNA, poly(CUG)exp, and its major cellular binding protein, MBNL1, the cell system most responsive to therapeutic effects is one in which every cell expresses poly(CUG) exp at levels just sufficient to sequester MBNL1 and induce a strong spliceopathy phenotype. Departure from this ideal reduces the responsiveness of an assay to therapeutic compounds. Cell-to-cell variability of transgene expression is likely to be a particular problem for poly(CUG)exp. Cells with subthreshold poly(CUG)exp accumulation never develop spliceopathy, whereas cells having a large burden of poly(CUG)exp are "resistant" to therapeutic effects. In either case, cells become unresponsive to test compounds and the power of the screen is correspondingly reduced.

(b) Overall Approach Using pLLC7 Construct

Constructs for expression of expanded CUG repeats present problems of instability and transgene silencing. To overcome these problems, three steps are employed to make stably transfected cells lines for optimal stability and uniformity of poly(CUG)exp expression. First, phiC31 integrase is used to obtain full-length, single-copy integrations. The transgene initially expresses a GFP-neomycin resistance selection cassette. Second, FACS is used to select cells lines that have uniform expression of the selection cassette. Any deleterious effects of poly(CUG)exp are avoided during initial isolation and selection clones. Third, cre recombinase is used to excise the neo-GFP cassette and activate expression of luciferase with poly(CUG)exp in the 3' UTR.

(c) Instability of Expanded CTG Repeats

CTG repeat tracts >150 repeats have a strong tendency for contraction in E. coli cloning vectors (Kang S, et al. Nat Genet 1995; 10(2):213-218), and it is difficult to clone repeat lengths above 250. Unavoidably, any plasmid prep containing an expanded CTG repeat consists of a heterogeneous mixture of different expansion lengths, and bacterial cultures seeded from the same stock show considerable prep-to-prep variability. This has a direct bearing on use of poly(CUG)exp-expression constructs: the genetic instability of expanded poly (CTG) compounds the problems inherent to transient transfection, namely, assay-to-assay variability in transfection efficiency and non-uniform transgene expression among cells that receive different doses of plasmid. This reduces the effectiveness of screening and create problems with transfer of assays to screening facilities, leading to choice of stable transfection as the preferred method for expressing poly (CUG)exp.

(2) Transgene Silencing

Gene transfer into mammalian cells is subject to variable transgene silencing. Silencing is enhanced by sequence repetition, as occurs in the large, multicopy transgene arrays that are typically produced with conventional procedures for stable transfection. Transgene silencing is especially prominent for transgenes that contain repetitive elements. Expanded CTG repeats are the strongest nucleosome positioning elements (Wang Y H, Griffith J. Genomics 1995; 25(2):570-573), and these sequences are particularly potent inducers of transgene silencing. These silencing effects characteristically are variable between cells, and semi-heritable in clonal isolates. Thus, conventional methods for obtaining stably transfected cells lines lead to complex, multicopy (dozens to hundreds of copies) transgene arrays. These cell lines are expected to show variable silencing, marked cell-to-cell variability in poly(CUG)$^{exp}$ accumulation, and unstable expression in subclones or bulk cultures over time.

(3) DMPK 3' UTR

Pathogenicity of the mutant DMPK mRNA may be influenced by elements that are within the DMPK 3' UTR but outside of the repeat tract (Amack J D, et al. Hum Mol Genet 2001; 10(18):1879-1887). Therefore, the DMPK 3' UTR has been incorporated in the construct to maintain cis elements that may influence the pathogenicity of poly(CUG)exp.

d) Bizyme Selection Cassette (Neomycin Phosphotransferase Fused to GFP)

This cassette allows selection of clones by neomycin resistance initially and subsequently by fluorescence (Hansen S G, et al. Biotechniques 2002; 32(5):1178, 1180, 1182-1178). The cDNA encoding Bizyme is followed by a concatamer of three SV40 transcription terminators (Novak A, et al. Genesis 2000; 28(3-4):147-155) ("triple stop"). The triple stop element was tested and showed that it completely prevents transcription of the downstream luciferase and CTG repeat, until after excision of the Bizyme selection cassette and triple stop by cre recombinase.

e) Procedures

Cells derived in methods disclosed herein are cotransfected with LLC7 and pCMVInt, and selected for G418 resistant clones as described above. Initially an LLC7 clone is selected containing (CTG)$^{300-350}$. The threshold for nuclear retention of transcripts containing poly(CUG)$^{exp}$ is not sharply defined. However, observations in C2C12 cells and transgenic mice indicate that transcripts with 150 repeats are nuclear retained, and that the extent of nuclear retention increases with larger expansion lengths (Amack J D, et al. Hum Mol Genet 1999; 8(11):1975-1984). By starting with a repeat length that is close to the upper limit of for cloning CTG expansions, relatively complete nuclear retention can be obtained. This reduces background luciferase activity and more closely approximates the near-complete nuclear retention observed in human DM1. Next clones having uniform GFP fluorescence are selected by FACS. These clones are transiently transfected with cre-recombinase expression vector, then reverse selected for clones that have lost GFP expression. The clones are compared by fluorescence in situ hybridization (FISH), MBNL1 immunofluorescence, and splicing analysis after transient transfection with pSERF. FISH to detect ribonuclear foci of poly(CUG)$^{exp}$ combined with immunofluorescence to detect MBNL1 is an established procedure. The expected outcome in cells showing spliceopathy is sequestration of MBNL1 in ribonuclear foci. Optimal clones show consistent sequestration of MBNL1 in ribonuclear foci, and splicing of pSERF is expected to revert to the SERCA1 exon 22 skipped isoform (low ratio of YFP:Y•CFP fluorescence).

f) Calibration and Variance of pSERF Fluorescence Splicing Reporter

Previous reports of emission and excitation spectra for eCFP are somewhat variable, and there is potential for FRET interaction between eYFP and eCFP components of Y•CFP (Pollitt S K, et al. Neuron 2003; 40(4):685-694). Full spectral analysis is conducted for eYFP, eCFP, and Y•CFP fusion protein in cells and the extent of FRET in Y•CFP determined. This work is carried out using the Varian Eclipse fluorometer. A strong FRET interaction can provide a method to directly determine the signal from Y•CFP (i.e., excite CFP, read at YFP emission wavelength, adjust for cross excitation). Alternatively, measuring FRET may not offer any advantage over simple analysis of eYFP and eCFP emission ratios, when each is excited at wavelengths that provide the least cross excitation. The outcome of these experiments is to select the wavelengths that are optimal for determining the ratio of YFP:Y•CFP when co-expressed. The strategies disclosed herein are tested in a mixing experiment in which known ratios of eYFP and Y•CFP are analyzed, and calibrated against RNA splicing results determined by RT-PCR analysis of exon 22 inclusion. It is likely that stable transfection generates clones that display a variety of different splicing outcomes, depending on levels of MBNL1 or poly(CUG)$^{exp}$ expression achieved in a particular clone. If so, this panel of "intermediate" clones, not selected for the final assay, but displaying varying degrees of exon 22 inclusion, are used to correlate fluorescence readouts obtained from intact cells using the fluorometer with subsequent RNA extraction for splicing analysis. In this manner, the well-to-well and assay-to-assay variance in fluorescence reading is determined across the full spectrum of splicing outcomes. If such "intermediate" clones are not available, the full spectrum of splicing outcomes can be reconstitute by transfecting (unmodified) 293 cells with pSERF and increasing amounts of pM1, to drive increasing levels of exon 22 inclusion. By either approach, the relationship between the fraction of transcripts that include exon 22 and the ratio of eCFP/eYFP activity is straightforward: eYFP is a component of every splicing outcome, whereas eCFP wanes in direct proportion to the increasing levels of exon 22 inclusion. From these results, the coefficient of variation between wells and Z' factor is calculated (Zhang J H, et al. J Biomol Screen 1999; 4(2):67-73), and detection threshold for effects on spliceopathy can be estimated.

To accomplish this assay cells are transfected with pSERF, and 24 hours later dispensed to 96 well plates using a Labsystems Multidrop plate filler. Test compounds are added to a final concentration of 10 µM. Fluorescence analysis of pSERF splicing are determined 24 hours later. Positive results are confirmed in a repeat experiment using replicate wells, and subsequently assessed using other assays.

7. Example 7

Figure 4:
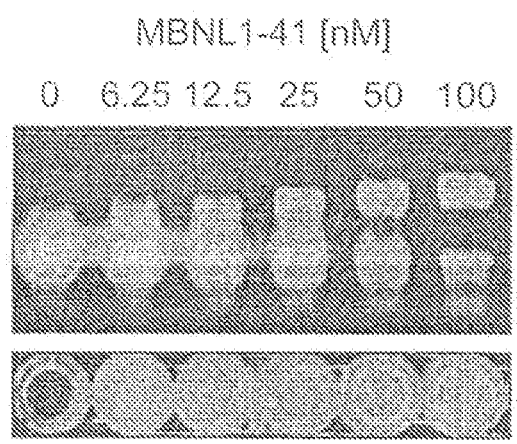
FIG. 4. Optimization of conditions for monitoring of poly(CUG)109-MBNL1 interaction in microplate format. In upper panel, gel mobility shift assay demonstrates interaction of fluorescently-labeled poly(CUG)109 (0.5 pmole) with increasing concentration of full-length, GST-cleaved recombinant MBNL1. Note that increasing MBNL1 concentration influences both percentage of poly(CUG)109 in complex with protein and the molecular weight of complex (increasing number of MBNL1 molecules bound per transcript). Lower panel shows the interaction in microplate format, with fluorescence-labeled MBNL1 binding to unlabeled poly(CUG)109 tethered to plate.

Cell-Based Assay for Compounds that Inhibit the Interaction of MBNL1 with Poly(CUG)Exp In Vivo Inhibition of MBNL1-poly(CUG)exp interaction is a logical therapeutic objective in DM1. The spliceopathy assay can identify compounds having this activity. However, more direct screens for inhibitors of MBNL1-poly(CUG)exp interaction can be more sensitive, or they can identify different sets of compounds. For example, the spliceopathy screen can give negative results for compounds that inhibit MBNL1 recognition of its physiologic (splice enhancer elements) as well as its pathologic (poly(CUG)exp) targets. Nevertheless, these compounds can preferentially inhibit the pathologic interaction at a different concentration, or furnish scaffolds that, with further investigation of structure activity relationships, can be modified to preferentially target the pathological interaction.

a) Assay for Compounds that Trigger Release of Poly(CUG)Exp-Containing Transcripts to the Cytoplasm.

siRNA-mediated knockdown of MBNL1 resulted in ~70% reduction of foci in DM1 myoblasts. Based on these observations, it was determined that MBNL1-poly(CUG)exp interaction is the primary determinant of ribonuclear foci formation in DM1 myoblasts (Dansithong W, et al. J Biol Chem 2005; 280(7):5773-5780). Disclosed herein, poly(CUG)exp transcripts in vitro show formation of very high molecular weight complexes in the presence of purified recombinant MBNL1 (FIG. 4). When these high molecular weight complexes form in cells, they result in nuclear retention of poly(CUG)exp-containing mRNA. These findings indicate that inhibition of MBNL1 recognition results in increased nucleocytoplasmic transport and translation of poly(CUG)exp-containing mRNA.

b) Effect of MBNL1 on Translation of mRNA Containing Poly(CUG)Exp in the 3' Untranslated Region.

293 cells are stably transfected with an expanded repeat (~300 repeats, lucCUG300) or non-repeat version (lucCUGØ) of pLLC7. These cells are expected to have strong expression of luc mRNA but modest endogenous expression of MBNL1. Using these cells, the effect of MBNL1 knockdown (using siRNAs that target the MBNL1 coding region (Dansithong W, et al. J Biol Chem 2005; 280(7):5773-5780)) or overexpression (transient transfection of pM1) on luciferase activity, nuclear foci, and distribution of luc mRNA can be compared in nuclear vs cytoplasmic fractions. As compared to MBNL1 knockdown, MBNL1 overexpression enhances nuclear foci, reduce luciferase activity, and increase the nuclear:cytoplasmic ratio of mRNA for lucCUG300 but not for lucCUGØ.

c) Assay for Compounds that Release Poly(CUG)Exp-Containing mRNA from Nuclear Foci.

The cell lines disclosed herein, can be employed in the cytoplasmic release assay without further modification. Clones for luciferase activity are compared in the presence and absence of siRNA knockout of MBNL1. Clones that are most responsive to MBNL1 knockdown, as determined by upregulation of luciferase activity, are selected.

d) Fluorescence Complementation Assay for MBNL1-Poly(CUG)Exp Interaction in Cells.

Interaction between poly(CUG)exp and MBNL1 is evaluated in cells by combining FISH detection of poly(CUG)exp RNA with immunofluorescence detection of MBNL1 to show colocalization. Poly(CUG)exp and MBNL1 interaction can be demonstrated in cell lysates by immunoprecipitation of the poly(CUG)exp transcript with antibodies to MBNL1 (X Lin, C Thornton, unpublished). However, neither method is highly amenable to screening assays. Therefore, a fluorescence complementation assay is used to detect and quantify MBNL1-poly(CUG)exp binding in cells. This approach is a modification of the trimolecular fluorescence complementation (TriFC) method (Rackham O, Brown C M. EMBO J 2004; 23(16):3346-3355).

e) Experimental System

Figure 8:
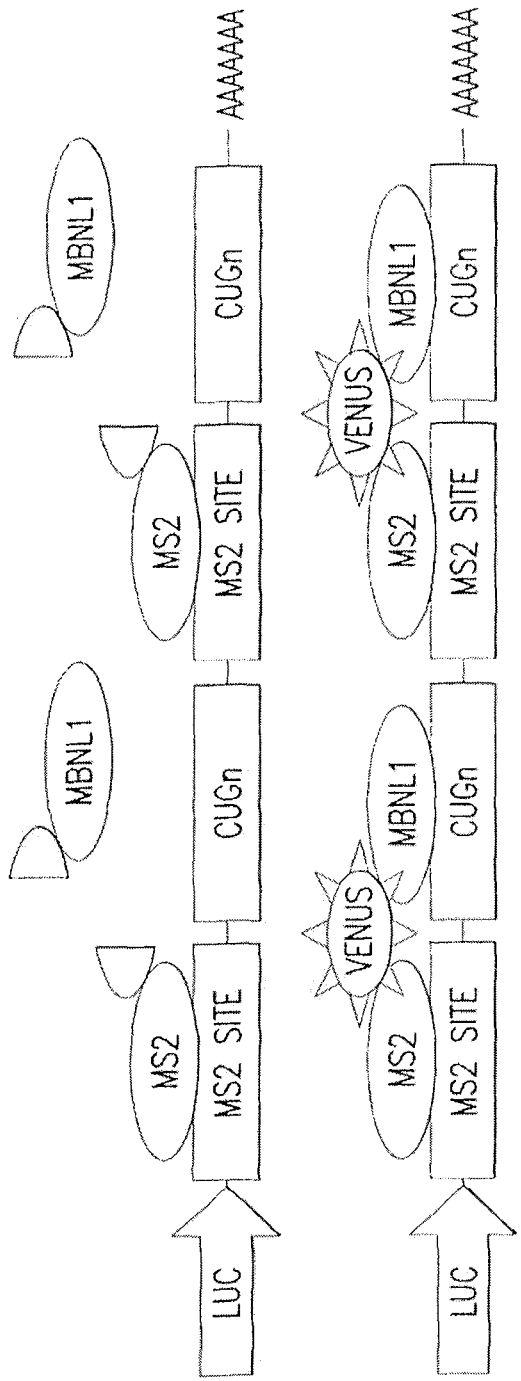
FIG. 8. Trimolecular fluorescence complementation assay for compounds that inhibit MBNL1 binding to poly(CUG) exp. In the 3' UTR of luc mRNA, poly(CUG)exp is interspersed with MS2 coat protein RNA recognition elements (MS2REs). MS2 coat protein (MS2CP) and MBNL1 are expressed as fusions with the N and C terminal halves of split Venus fluorescent protein (Nagai T, et al. Nat Biotechnol 2002; 20(1):87-90) (VFP), respectively. Assembly of MS2CP•VFPN and MBNL1•VFPC on the chimeric transcript leads to VFP fluorescence activity (Rackham O, Brown C M. EMBO J 2004; 23(16):3346-3355). Inhibition of MBNL1-poly(CUG)exp interactions causes loss of VFP fluorescence.
Figure 9:
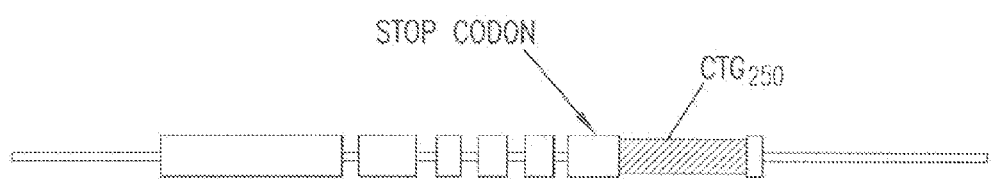
FIG. 9 shows a diagram of the transgene in HSALR transgenic mice. To produce a transgenic mouse model of myotonic dystrophy, an expanded CTG repeat was inserted downstream from the stop codon in a DNA fragment containing the entire human skeletal actin gene. This fragment was used to derive HSALR transgenic mice. It was found that these transgenic mice express high levels of CUG expansion RNA in skeletal muscle. They also develop myotonia, a cardinal symptom of myotonic dystrophy, and histologic changes in skeletal muscle that resemble myotonic dystrophy.
Figure 10:
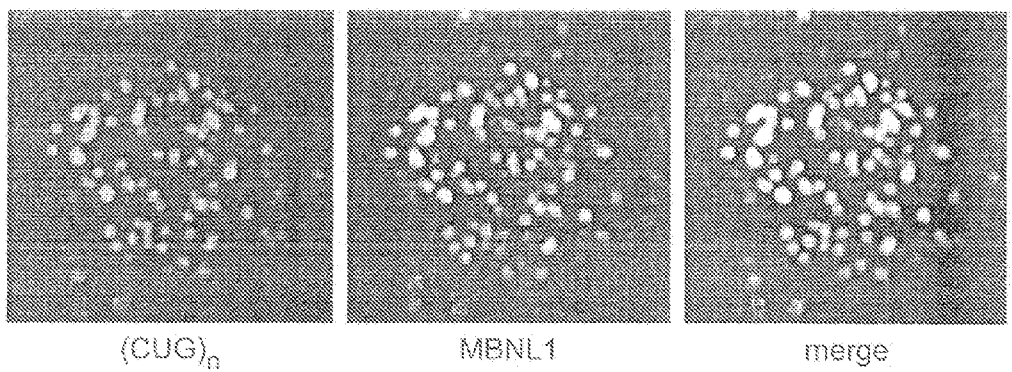
FIG. 10 shows that MBNL1 protein is sequestered in ribonuclear foci of CUG repeat RNA in $HSA^{LR}$ transgenic mice. This high power view of a section of skeletal muscle shows a single nucleus at postnatal day 2. In the left panel, ribonuclear foci of CUG expansion RNA are shown by fluorescence in situ hybridization. In the center panel, the distribution of MBNL1 protein in the nucleus is shown by immunofluorescence. The merged image on the right shows that MBNL1 is sequestered in the ribonuclear foci of CUG expansion RNA.
Figure 11:
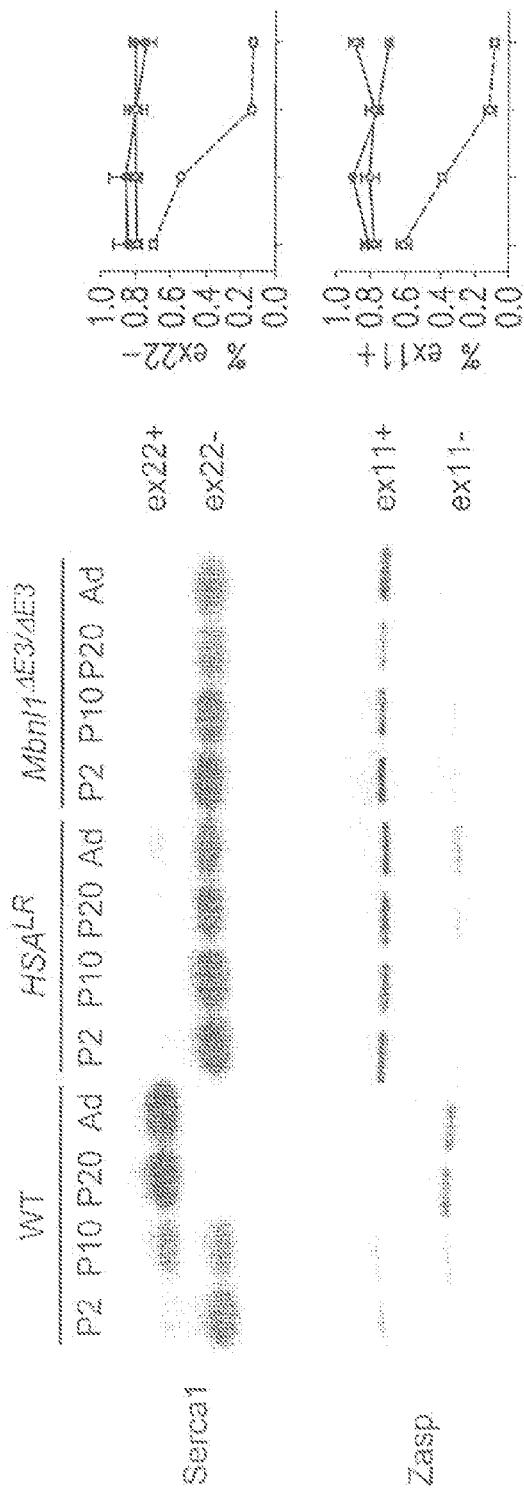
FIG. 11 shows that MBNL1 is required for normal developmental regulation of alternative splicing for SERCA1 and ZASP. The left panel shows reverse transcriptase-PCR (RT-PCR) analysis of alternative splicing for SERCA1, the calcium reuptake pump of the sarcoplasmic reticulum, and ZASP, a structural component of the Z disc. In wild-type mice, alternative splicing of SERCA1 exon 22 is developmentally regulated. At postnatal day 2 (P2), exon 22 is mainly skipped. By postnatal day 20 (P20), and continuing in adults (Ad), exon 22 is mainly included. However, this transition of alternative splicing fails to occur in mice deficient for MBNL1 (Mbnl1$^{\Delta E3/\Delta E3}$). A similar pattern of failure is seen for $HSA^{LR}$ transgenic mice. Exon 11 of ZASP shows an alternative splicing transition during the same interval of postnatal development. The transition from exon 11 inclusion to exon 11 exclusion fails to occur in MBNL1 deficient or $HSA^{LR}$ transgenic mice.
Figure 12:
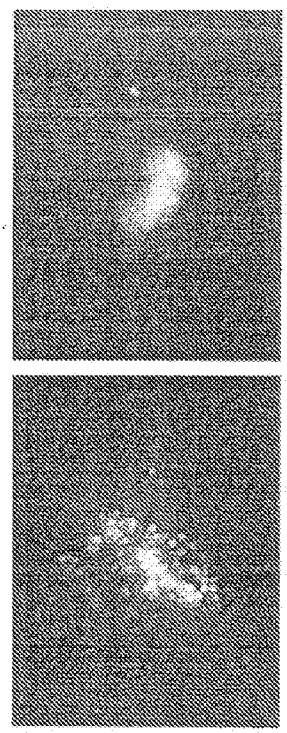
FIG. 12 shows a morpholino composed of CAG repeats displaced MBNL1 protein from ribonuclear foci in $HSA^{LR}$ transgenic mice. The morpholino was compromised entirely of CAG repeats and was 25 nucleotides in length (CAG25). CAG25 morpholino dissolved in phosphate buffered saline was injected into tibialis anterior muscle of $HSA^{LR}$ transgenic mice, followed by electroporation to facilitate entry into muscle cells. The contralateral tibialis anterior muscle was injected with saline alone, followed by electroporation. The distribution of MBNL1 in tibialis anterior was determined by immunofluorescence with anti-MBNL1 antibody A2764. In muscle injected with saline, MBNL1 was sequestered in ribonuclear foci (nuclei are counterstained with DAPI). In muscle injected with CAG25 morpholino, MBNL1 was became more widely distributed throughout the nucleus.

The system involves 3 components: (1) chimeric transcripts that contain poly(CUG)exp adjacent to the RNA element recognized by bacteriophage MS2 coat protein; (2) MBNL1 protein fused to the C terminal portion of Venus fluorescent protein (VFPC); and (3) MS2 coat protein (MS2CP) fused to the N terminal portion of VFP (VFPN) (FIG. 8). When all 3 components are co-expressed, the expected result in the basal state is strong VFP fluorescence because MBNL1•VFPC and MS2CP•VFPN assemble in close proximity on the chimeric poly(CUG)exp transcript, whereas compounds that inhibit the poly(CUG)exp-MBNL1 interaction reduce VFP fluorescence. The specificity and sensitivity of TriFC as a method to detect binding of two proteins to adjacent regions of mRNA was initially demonstrated for the zipcode binding protein, IMP1, and MS2CP (Rackham O, Brown C M. EMBO J 2004; 23(16):3346-3355). TriFC generated strong fluorescence signals when MS2CP•VFPN and IMP1•VFPC were co-expressed with a transcript containing adjacent MS2 and IMP1 recognition elements in the 3' UTR. Mutations in the RNA target which eliminated MS2CP or IMP1 binding caused loss of fluorescence signal (Rackham O, Brown C M. EMBO J 2004; 23(16):3346-3355). Results were similar with other RNA binding proteins and their respective RNA recognition elements. The background was low and VFP had the advantages of bright fluorescence, monomeric structure, and rapid maturation (Nagai T, et al. Nat Biotechnol 2002; 20(1):87-90).

(1) Procedures to Develop TriFC Assay

To develop cell lines that express an mRNA target for assembly of the trimolecular complex, a modified "CTG donor plasmid" containing a chimeric poly(CTG)exp-MS2RE insert is cloned. This fragment is subcloned directly into pLLC7 (FIG. 7). The chimeric sequence contains two tracts of expanded CTG repeats, each consisting of 130 repeats, interspersed with two MS2 binding sites, each consisting of a dimer of the MS2RE (see FIG. 8). After selecting cell lines with uniform expression of the GFP-neomycin resistance cassette, the cassette is removed by cre recombination.

Two fusion proteins are constructed, MS2CP and MBNL1, tagged with the N- and C-portions of split Venus protein (VFPN and VFPC). MS2CP•VFPN has been shown to retain high affinity for MS2 binding sites (Rackham O, Brown C M. EMBO J 2004; 23(16):3346-3355). MBNL1-VFPC fusion protein is expected to retain high affinity for poly(CUG)exp, because MBNL1 tagged with eGFP retained its poly(CUG) exp binding and splicing regulatory activity (Ho T H, et al. EMBO J 2004; 23(15):3103-3112; Fardaei M, et al. Nucleic Acids Res 2001; 29(13):2766-2771).

The specificity and localization of the trimolecular interaction is examined. Cells stably expressing chimeric poly(CUG)exp•MS2RE and control cells expressing poly(CUG) exp with no MS2 binding sites are transiently transfected with constructs encoding MS2CP•VFPN, MBNL1-VFPC, or both. Fluorescence detection of Venus protein is combined with FISH detection of poly(CUG)exp.

When the MBNL1-VFPC binding to chimeric poly(CUG) exp•MS2RE transcripts results in strong VFP fluorescence, then stable transfection of the MBNL1-VFPC construct is conducted. Analysis of well-to-well and assay-to-assay variance is carried out using the Varian fluorometer and cells stably transfected to express the chimeric transcript and MBNL1-VFPC, and transiently transfected to express MS2CP•VFPN.

8. Example 8

Biochemical Assay for Compounds that Inhibit MBNL1-Poly(CUG)Exp Interaction In Vitro A biochemical screen with simple components is probably the most sensitive means to detect inhibitors of MBNL1 binding to poly(CUG)$^{exp}$. A biochemical screen can identify compounds not captured by cell-based screens due to reasons of cell toxicity, compound instability, impermeability, or protein binding. Such compounds nevertheless can provide scaffolds that can be modified to improve activity in vivo. In addition, it is possible to identify simple compounds that bind poly (CUG)$^{exp}$ and show modest displacement of MBNL1, and then enhance the binding affinity by presenting the compound in dimer or oligomeric structures that are spaced according to the periodicity of the poly(CUG)$^{exp}$ duplex. Finally, a biochemical screen provides an important tool for secondary evaluation of hits from the cell-based screens.

Figure 2A:
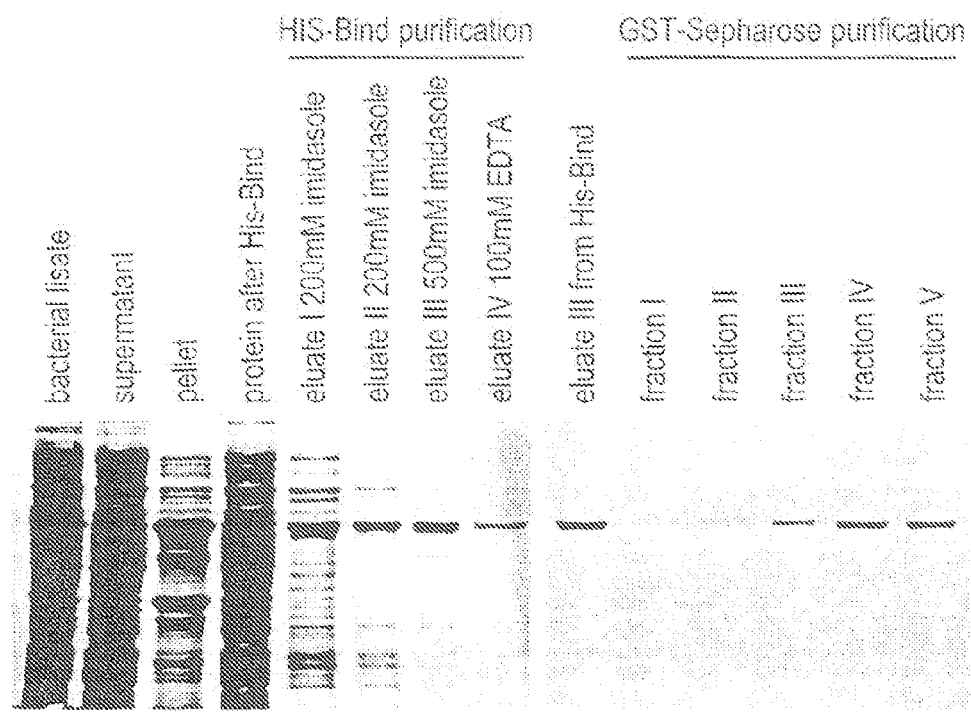
FIGS. 2A and 2B show synthesis, purification and fluorescent labeling of MBNL1 protein and poly(CUG) transcript.

MBNL1 protein is hydrophobic and basic (pH 8.9) so the majority of protein synthesized in bacteria is denatured or in inclusions. By tagging human MBNL1 at the C-term with poly-histidine (His$_6$) and at the N-term with glutathione S transferase (GST) and a Prescission protease cleavage site, GST-MBNL1-His$_6$ was expressed at high levels in BL21 (DE3) cells. A purification was developed (FIG. 2A) that produces ~95% full-length MBNL1: (1) affinity chromatography on Ni-column; (2) affinity chromatography on GST-sepharose followed by protease cleavage to release MBNL1-His$_6$; and (3) G25-sephadex with exchange buffer. Initially precipitation of MBNL1-His$_6$ was found in several storage buffers. However, solubility in 100 mM Tris pH 8.0, 50 mM NaCl, 10% glycerol, 0.1% Triton X-100 was good. The yields are 1 to 10 mg of MBNL1 protein per liter of bacterial culture, depending on the MBNL1 isoform. The purification scheme was optimized using MBNL1-41 and MBNL1-42 kD isoforms, which seem to have similar binding and splicing factor activities (see FIG. 5 below), as well as a truncated form which removes hydrophobic sequence at the C-terminal and improves the yield of soluble protein from E. coli. The truncated protein includes all four zinc-fingers and other regions that are conserved among MBNL family members, and its poly(CUG) binding activity remains intact. Importantly, the purified recombinant MBNL1 does not display ribonuclease activity when incubated with test transcripts.

Figure 2B:
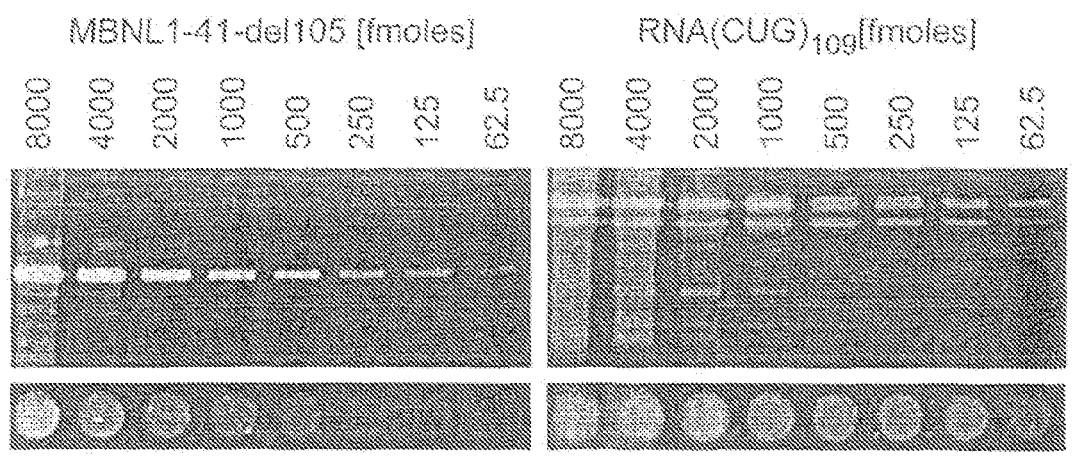

Constructs for in vitro transcription of poly(CUG)$^{109}$ have been prepared and conditions for enzymatic synthesis and purification of non-radioactively labeled transcripts have been optimized (FIG. 2B). The poly(CUG)$^{109}$ transcript contains an A-rich sequence at the 3' end. In addition, the triplet repeat is fused directly to a modified T7 promoter to eliminate A nucleotides 5' to the poly(CUG) tract. This allows biosynthetic labeling to high specific activity using fluorescently labeled ATP, while avoiding premature terminations or internal labeling within the poly(CUG) tract that might impact RNA folding or MBNL1 binding. In addition, the A-rich 3' tail is devoid of secondary structure and also functions as anchoring sequence for capture of poly(CUG)$^{109}$ by oligonucleotides attached to the surface of microtiter plates. Before binding assays, transcripts are denatured at 80° C. and renatured under conditions that favor folding of poly(CUG)$^{109}$ as a single hairpin structure.

Next, optimal conditions were defined (ionic-strength, monovalent cations, Mg$^{++}$ and other additions, temperature) for MBNL1-poly(CUG)$^{109}$ binding in solution. All forms of recombinant MBNL1 that were tested (GST fused or cleaved, full-length or truncation of C terminal hydrophobic region, 41 or 42 kD isoform) bind to poly(CUG)$^{109}$ at low protein concentration (FIG. 3, Kd values ~10 nM), as determined by nitrocellulose filter binding assays. In this assay, nonspecific binding of labeled RNA to nitrocellulose was very low (<0.2% of maximal positive signal). As described below, disclosed herein are methods comprising a non-radioactive microtiter plate filter binding assay similar to the one used to examine binding activities of different forms of recombinant MBNL1 in FIG. 3.

Also disclosed herein are methods involving the interaction of soluble, fluorescently-labeled MBNL1 protein with poly(CUG)$^{109}$ tethered at the surface of a microtiter plate. Different commercial microtiter plates for capacity to bind in vitro transcribed poly(CUG)$^{109}$ and background activity (non-specific binding of labeled MBNL1). For tethering poly (CUG)$^{109}$ to plates, a "capture" oligodeoxynucleotide (ODN) complementary to the A-rich 3' terminus of the poly(CUG)$^{109}$ transcript, labeled either with biotin or a reactive group at the 5' end for attachment to the plate (shown in FIG. 3C in the case of biotin) was used. Surprisingly, the streptavidin-coated polystyrene plates (Nunc) had greater capacity to bind poly (CUG)$^{109}$ and displayed lower background binding of MBNL1 protein than plates with reactive surface chemistries that allowed direct covalent attachment of the capture oligonucleotide. Next, the concentration of capture ODN that saturates binding sites (12.5 pmoles/100 µl/well) and the concentration of poly(CUG)$^{109}$ that saturates the capture ODN (of 5 pmole added per well, 0.5 pmole was bound to capture ODN) were determined. Additionally, conditions for fluorescence labeling of MBNL1 protein via conjugation between primary amines on protein and fluorescein-EX dyes (Molecular Probes) were determined. The detection threshold and range of linearity was determined for labeled protein in gels and microplates (FIG. 2B). The interaction of recombinant MBNL1 with poly(CUG)$^{109}$ was examined by gel shift assay, confirming the prediction that increasing the ratio of MBNL1 to transcript results in formation of high molecular complexes due to binding of many protein molecules per transcript (FIG. 4, top panel). Finally, the efficiency of fluorescence-labeled MBNL1 binding to poly(CUG)$^{109}$ transcripts tethered on plates was determined (FIG. 4, bottom panel), which was sensitive to MBNL1 concentration as low as 6.25 nM and showed a 50-fold dynamic range.

a) Filter Retention Assay

Figure 3B:
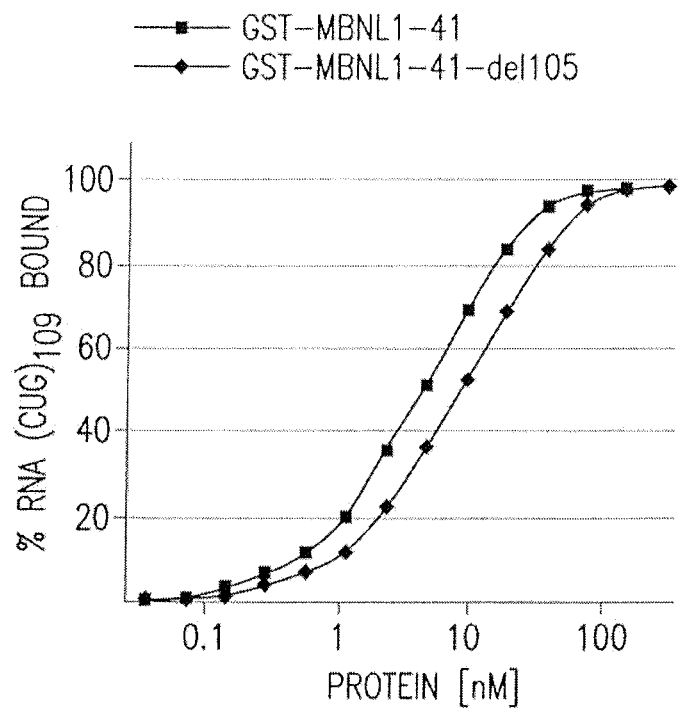

The two components of this assay, fluorescence-labeled poly(CUG)$^{109}$ (FIG. 2B) and recombinant MBNL1 (FIG. 2A), have been developed and optimal conditions for MBNL1 binding to poly(CUG)$^{exp}$ have been defined (50 mM Tris pH 8.0, 50 mM NaCl, 50 mM KCl, 1 mM Mg$^{++}$, 0.1 mM DTT) (see Preliminary Studies). Pilot binding assays have been carried out using nitrocellulose filters (FIG. 3A). Next these same reagents and conditions are employed to test commercially available filter plates. The Multiscreen$_{HTS}$ nitrocellulose filter plate (Millipore) has been previously used for a similar purpose (Bittker J A, et al. Nat Biotechnol 2002; 20(10):1024-1029). This plate is designed for automated handling in high throughput screens and is likely to have protein binding characteristics similar to the filter binding assay in FIG. 3A.

b) RNA Attachment Assay.

Figure 3C:
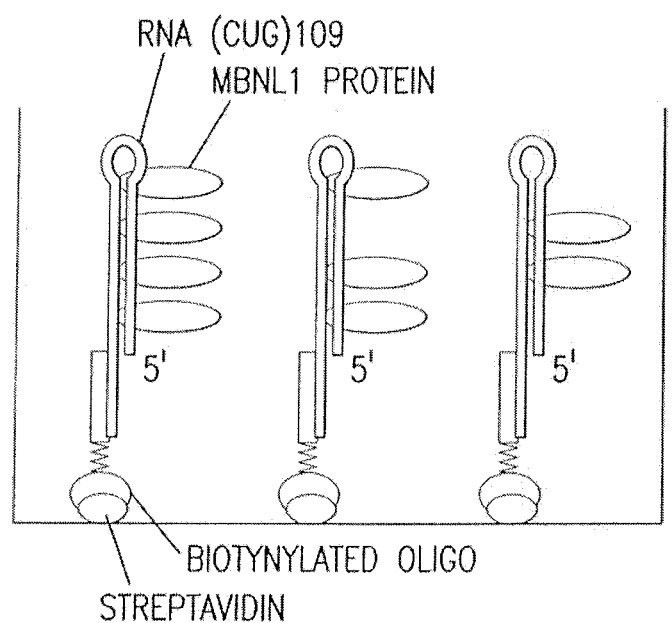

The alternative assay for inhibitors of MBNL1-poly(CUG)$^{exp}$ interaction involves tethering of unlabeled poly(CUG)$^{exp}$ to microtiter plates, and measuring the amount of fluorescently-labeled MBNL1 retained on the plate due to RNA binding (FIG. 3C). Methods for synthesis and tethering of poly(CUG)$^{109}$ RNA are described in Preliminary Studies and diagrammed in FIG. 3C. Results of fluorescence labeling of purified recombinant MBNL1 are shown in FIG. 2B. Coupling efficiency for labeling was ~2-6 fluorochromes per molecule of GST-MBNL1, using the FluoReporter protein labeling kit (Molecular Probes). GST-MBNL1 is used for these assays, because the presence of GST fusion partner does not appear to influence affinity of MBNL1 for poly(CUG)$^{exp}$ (FIG. 3A), and increasing the mass of MBNL1 permits higher fluorescence activity with less risk of fluorochrome attachment at the RNA binding site. As described in herein, streptavidin-coated polystyrene microtiter plates (Nunc) were noted as providing the highest capacity for poly(CUG)$^{109}$ binding and lowest background of MBNL1 binding in the absence of poly(CUG)$^{exp}$. The material requirements for these assays are feasible. 10-100 nM concentration of MBNL1 is suitable (lanes 4-6, FIG. 4, bottom panel). At these concentrations with 100 μl per well, 1 mg protein is sufficient for at least 2000 wells. The potential advantage of the RNA attachment assay, over the filter binding assay, is greater sensitivity to inhibitors because it detects varying degrees of displacement of MBNL1 from poly(CUG)$^{109}$, whereas even a single residual MBNL1 molecule bound to poly(CUG)$^{109}$ is sufficient to induce retention on the filter. The potential disadvantage is the need for more liquid handling steps including aspiration of wells, which may dictate that this assay remains a work station procedure that cannot be scaled up to high throughput.

Disclosed herein, poly(CUG)$^{exp}$ displays considerable resistance to ribonuclease cleavage, owing to its highly stable secondary structure (Tian B, et al. Rna 2000; 6:79-87). However, the A-rich 3' end of the poly(CUG)$^{109}$ transcript, which contains the fluorescence label in the filter binding assay and mediates tethering in the plate attachment assay, is not protected in this manner. The sequence of this tail has been specifically designed to avoid dinucleotide combinations that confer RNase sensitivity. Further protection is achieved by addition of a complementary morpholino to the filter binding assay, or use of a morpholino as "capture" oligonucleotide in the plate attachment assay. Addition of irrelevant, unstructured RNA to test buffer and use of short incubation times further reduce RNase activity.

9. Example 9

Correction of ClC-1 Splicing Eliminates Chloride Channelopathy and Myotonia in Mouse Models of Myotonic Dystrophy DM type 1 (DM1), the most common muscular dystrophy affecting adults, is caused by expansion of a CTG repeat in the 3' untranslated region of the gene encoding the DM protein kinase (DMPK) (Brook, J. D., et al. (1992) Cell 68:799-808). Evidence suggests that DM1 is not caused by abnormal expression of DMPK protein, but rather that it involves a toxic gain-of-function by mutant DMPK transcripts that contain an expanded CUG repeat (CUG$^{exp}$) (Osborne, R. J., and Thornton, C. A. (2006) Hum Mol Genet 15 Spec No 2:R162-169). The transcripts containing a CUG$^{exp}$ tract elicit abnormal regulation of alternative splicing, or spliceopathy (Philips, A. V., et al. (1998) Science 280:737-741). The splicing defect, which selectively affects a specific group of pre-mRNAs, is thought to result from reduced activity of splicing factors in the muscleblind (MBNL) family (Kanadia, R. N., et al. (2003) Science 302:1978-1980), increased levels of CUG binding protein 1 (Philips, A. V., et al. (1998) Science 280: 737-741; Charlet, B. N., et al. (2002) Mol Cell 10:45-53), or both. Decreased activity of MBNL proteins can be attributed to sequestration of these proteins in nuclear foci of CUG$^{exp}$ RNA (Miller, J. W., et al. (2000) Embo J 19:4439-4448; Lin, X., et al. (2006) Hum Mol Genet 15:2087-2097).

Disclosed herein, transgenic mice expressing CUG$^{exp}$ RNA (HSA$^{LR}$ mice) displayed myotonia and chloride channel 1 (ClC-1) splicing defects similar to those observed in DM1 (Mankodi, A., et al. (2002) Mol Cell 10:35-44). Myotonia in the HSA$^{LR}$ model results from abnormal inclusion of exon 7a in the ClC-1 mRNA, owing to sequestration of MBNL1, a factor required for repression of exon 7a splicing in muscle fibers (Kanadia, R. N., et al. (2003) Science 302: 1978-1980). This mechanism is supported by several lines of evidence: (1) inclusion of exon 7a causes frame shift and introduction of a premature termination codon in the ClC-1 mRNA (Mankodi, A., et al. (2002) Mol Cell 10:35-44; Charlet, B. N., et al. (2002) Mol Cell 10:45-53); (2) truncated ClC-1 protein encoded by the exon 7a+ isoform is devoid of channel activity (Berg, J., et al. (2004) Neurology 63:2371-2375); and (3) disruption of Mbnl1 in mice leads to increased inclusion of ClC-1 exon 7a and myotonia (Kanadia, R. N., et al. (2003) Science 302:1978-1980). The postulate that myotonia in DM1 results from deficiency of ClC-1 is based on observations that mouse models of DM1 display a 70-80% reduction of muscle chloride conductance (Mankodi, A., et al. (2002) Mol Cell 10:35-44; Lueck, J. D., et al. (2007) J Gen Physiol 129:79-94), coupled with previous estimates that a 75% reduction of ClC-1 conductance is sufficient to cause myotonic discharges in muscle fibers (Furman, R. E., and Barchi, R. L. (1978) Ann Neurol 4:357-365). However, the mechanism of ClC-1 downregulation and its requirement for myotonia in DM1 is controversial. Effects on sodium or potassium channels have also been implicated in DM1-associated myotonia (Franke, C., et al. (1990) J Physiol 425:391-405; Renaud, J. F., et al. (1986) Nature 319:678-680; Behrens, M. I., et al. (1994) Muscle Nerve 17:1264-1270). In addition, evidence that chloride channelopathy in DM1 results from downregulation of ClC-1 transcription, rather than abnormal splicing, has been reported (Ebralidze, A., et al. (2004) Science 303:383-387). To provide a causal link between ClC-1 alternative splicing, chloride channelopathy, and myotonia in DM1, a morpholino AON was used to selectively repress the inclusion of exon 7a.

a) Results

Figures 23A, 23B:
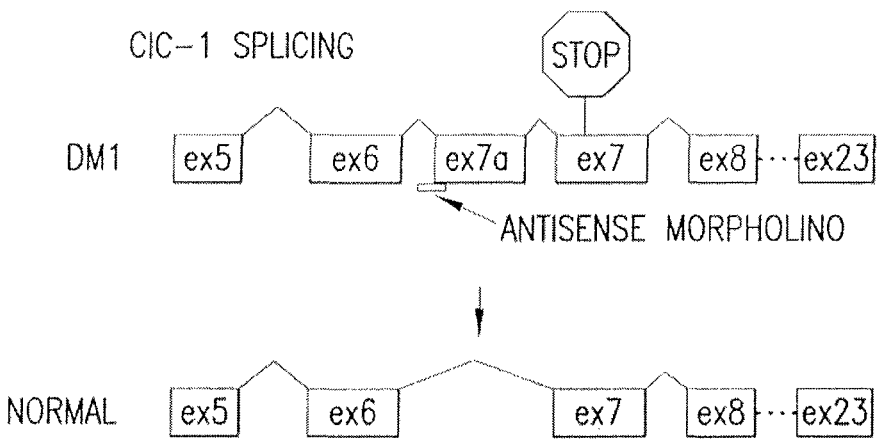
FIGS. 23A and 23B show the design of antisense morpholinos.
Figure 24A:
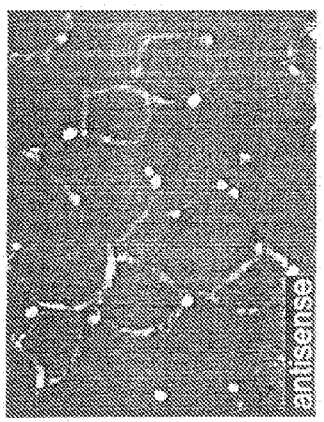
FIGS. 24A, 24B, 24C, 24D, 24E, 24F, and 24G show that antisense morpholino localizes preferentially to muscle nuclei and restores ClC-1 expression at the sarcolemma
Figure 24B:
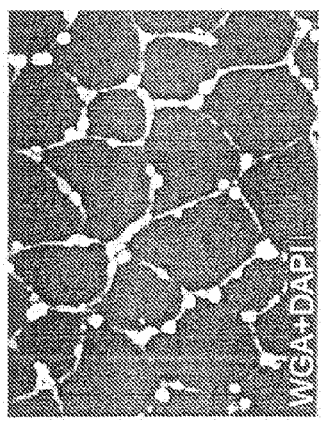
Figure 24C:
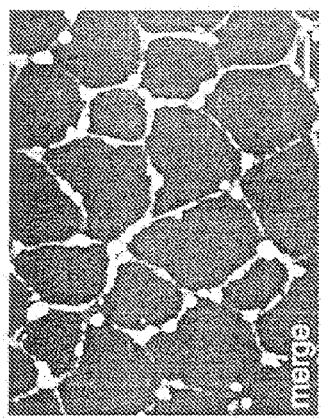

The strategy for suppressing the inclusion of exon 7a is diagrammed in FIG. 23A. The morpholino AONs were complementary to the 3' or 5' splice sites of exon 7a in the ClC-1 pre-mRNA (FIG. 23B). To examine tissue uptake, a carboxyfluorescein-labeled morpholino was injected into tibialis anterior (TA) muscle of HSA$^{LR}$ mice. Examination of tissue sections indicated that uptake of antisense morpholino was limited to the needle track. To improve uptake and distribution of AON, voltage pulses were used to electroporate muscle fibers after the AON injection. This led to uptake of antisense morpholino throughout the TA muscle (FIG. 24A-C). Of note, the AON was present in both nucleus and cytoplasm, but appeared to accumulate preferentially in the nucleus (FIG. 24A,E).

Figure 25A:
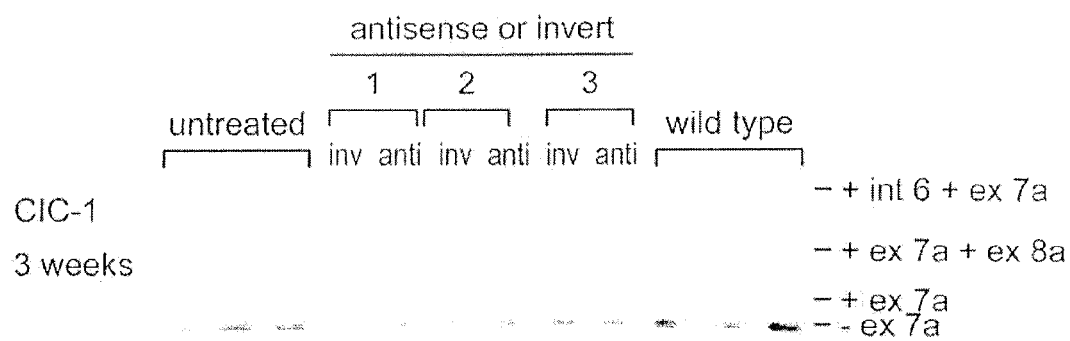
Figure 25B:
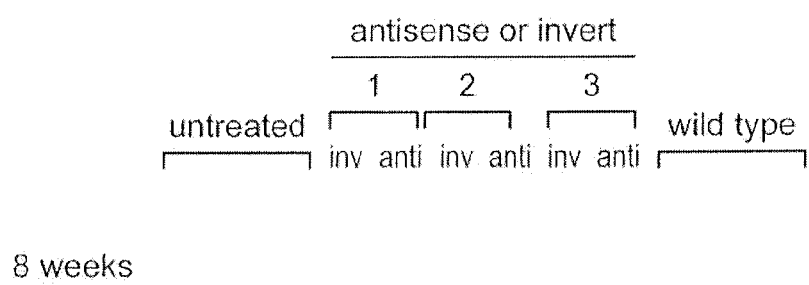
Figure 25C:
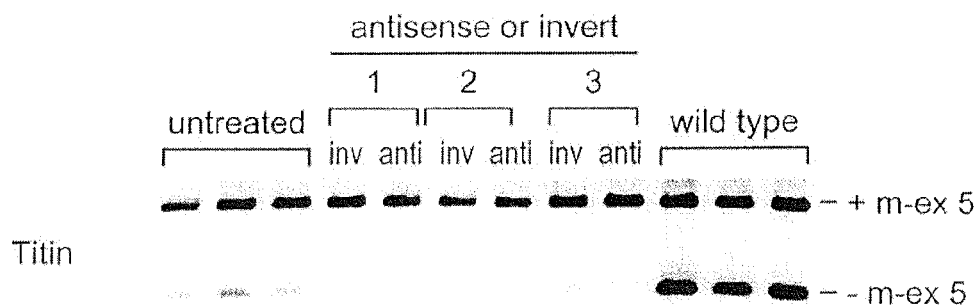

To determine the effect of morpholino on splicing in HSA$^{LR}$ mice, total RNA was extracted from TA muscle after AON injection. Analysis of ClC-1 splicing by RT-PCR showed that antisense morpholino had the intended effect of suppressing the inclusion of exon 7a, whereas control morpholino with inverted sequence had no effect on ClC-1 splicing in the contralateral TA (FIG. 25A,D). AON targeting the 3' splice site, or co-injection of AONs targeting the 3' and 5' splice sites, was more effective than targeting the 5' splice site alone (FIG. 28). Effective and sustained skipping of exon 7a was achieved after a single injection of morpholino AON. Inclusion of exon 7a was suppressed to wild type (WT) levels for at least 3 weeks after a single injection (FIG. 25A,D), and a partial exclusion of exon 7a was still evident after 8 weeks (FIG. 25B,E). Notably, the antisense morpholino did not affect the formation of nuclear foci containing CUG$^{exp}$ RNA and MBNL1 protein (FIG. 29), nor did it correct the alternative splicing of other genes that are misregulated in DM1, such as, Titin (FIG. 25C), ZASP, or Serca1 (Lin, X., et al. (2006) Hum Mol Genet 15:2087-2097). These data indicate that morpholino AON specifically corrects the ClC-1 splicing defect rather than producing a general reversal of DM-associated spliceopathy or Mbnl1 sequestration.

Figure 24D:
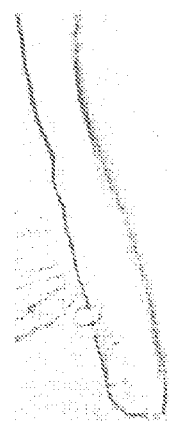
Figure 24E:
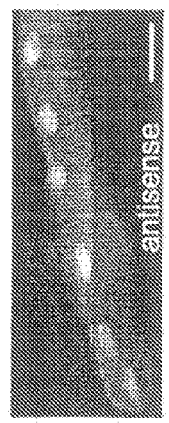
Figure 24F:
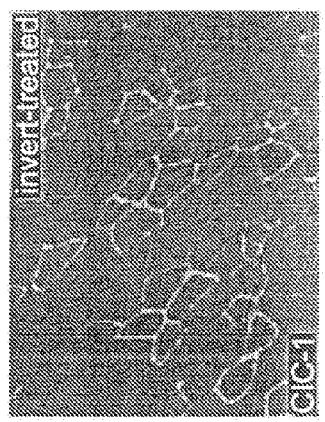
Figure 24G:
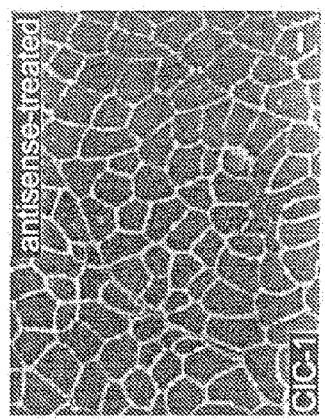
Figure 25D:
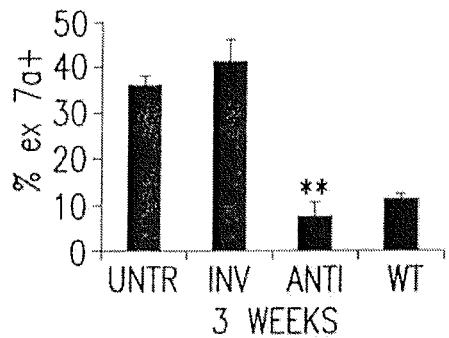
Figure 25E:
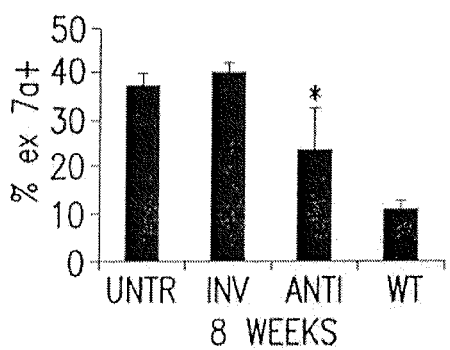
Figure 25F:
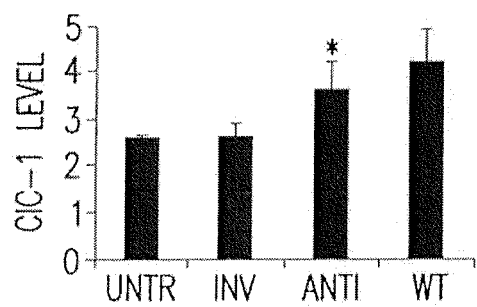

Morpholino AONs influence splicing outcomes without inducing degradation of their target RNAs (Mercatante, D. R., et al. (2001) Curr Cancer Drug Targets 1:211-230). Therefore, the predicted effect of repressing exon 7a inclusion was to eliminate the premature termination codon in ClC-1 mRNA and thereby reduce its degradation through the nonsense-mediated decay pathway (Lueck, J. D., et al. (2007) Am J Physiol Cell Physiol 292:C1291-1297). Consistent with this prediction, treatment with antisense morpholino, but not control morpholino with inverted sequence, led to increased levels of ClC-1 mRNA, as determined by quantitative real time RT-PCR (FIG. 25F). These results indicate that effects of $CUG^{exp}$ RNA on ClC-1 expression are mainly at the post-transcriptional level. Furthermore, treatment with morpholino AON increased the level of ClC-1 protein in the sarcolemma, as indicated by immunofluorescence using antibodies directed against the C-terminus (FIG. 24F,G).

Herein whole cell patch clamp analysis of single flexor digitorum brevis (FDB) muscle fibers was used to show that ClC-1 current density is reduced and channel deactivation accelerated in FDB fibers of untreated $HSA^{LR}$ mice (Lueck, J. D., et al. (2007) J Gen Physiol 129:79-94). Therefore, the effect of AON treatment on ClC-1 channel function was determined Hindlimb foot pads of 10-12-day-old WT and $HSA^{LR}$ mice were injected/electroporated with carboxyfluorescein-labeled antisense or invert morpholino. Patch clamp analysis was performed three-to-five days after injection, at a time when fibers were still small enough to maintain an effective voltage clamp (Lueck, J. D., et al. (2007) J Gen Physiol 129:79-94). Individual FDB fibers were isolated and macroscopic ClC-1 channel activity was measured in fibers exhibiting green fluorescence (FIG. 24D,E). ClC-1 current density (FIG. 26A,B) and deactivation kinetics (FIG. 26D) were rescued to WT values as early as 3 days after morpholino AON injection, while current density and deactivation kinetics in fibers treated with invert morpholino were not different from those of untreated $HSA^{LR}$ fibers. The slower rate of channel deactivation observed for WT and AON-treated fibers is most likely not due to a current-dependent effect on channel gating, because reducing WT ClC-1 current magnitude in half with a prepulse does not significantly alter the kinetics of channel deactivation (Lueck, J. D., et al. (2007) J Gen Physiol 129:79-94). Rescue of ClC-1 activity was not due to a shift in channel activation since the voltage dependence of relative channel open probability (Po) was not different between antisense and invert-injected $HSA^{LR}$ and WT fibers (FIG. 26C). These results demonstrate that morpholino AON rescue of ClC-1 spliceopathy is sufficient to completely restore normal ClC-1 current density and channel deactivation kinetics.

The effects of repressing exon 7a inclusion on muscle physiology in vivo was determined Electromyography (EMG) analysis by a blinded examiner revealed that myotonia was markedly reduced or absent in TA muscles of $HSA^{LR}$ mice after injection of antisense morpholino, whereas myotonia in the invert-injected contralateral TA was not different from uninjected muscle (FIG. 26E,F). Myotonia reduction correlated with the degree of exon 7a skipping at 3 and 8 week time points, indicating that a single injection of antisense morpholino provided a sustained reduction in myotonia.

Figure 27B:
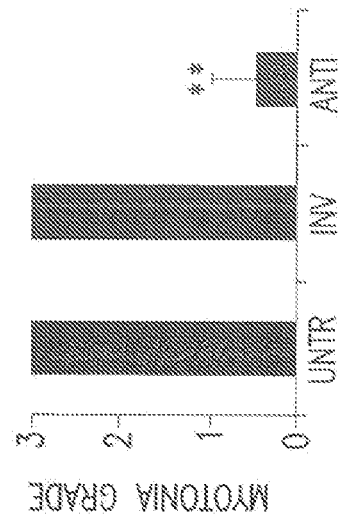
FIGS. 27A, 27B, 27C, 27D, and 27E show antisense morpholino represses exon 7a inclusion, restores ClC-1 protein expression, and rescues myotonia in Mbnl1$^{ΔE3/ΔE3}$ mice.
Figure 27E:
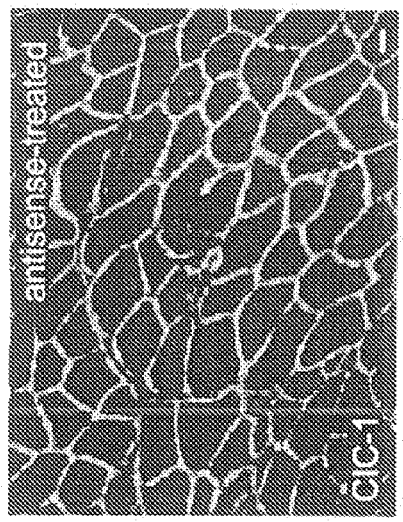
Figure 27A:
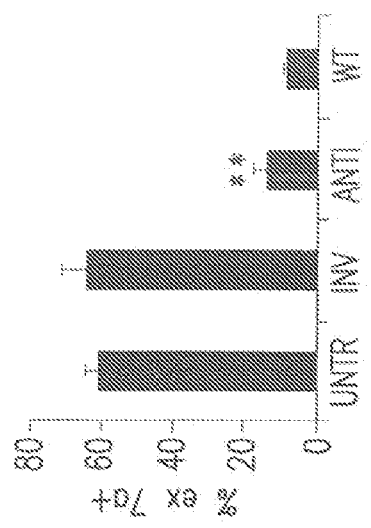
Figure 27C:
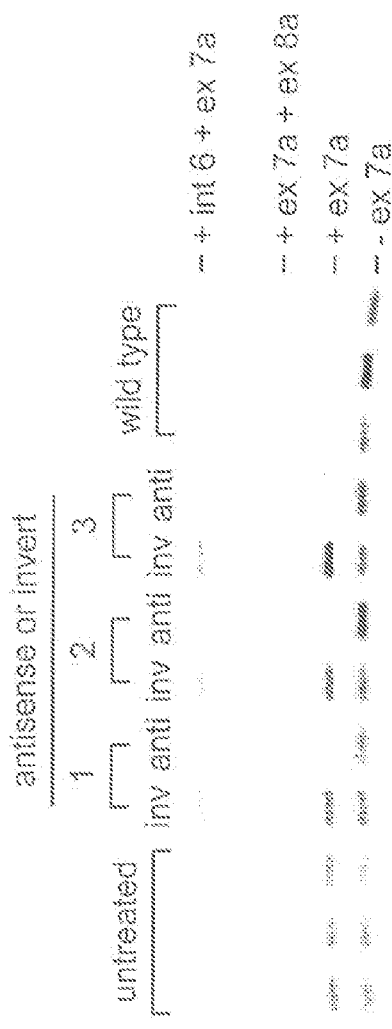
Figure 27D:
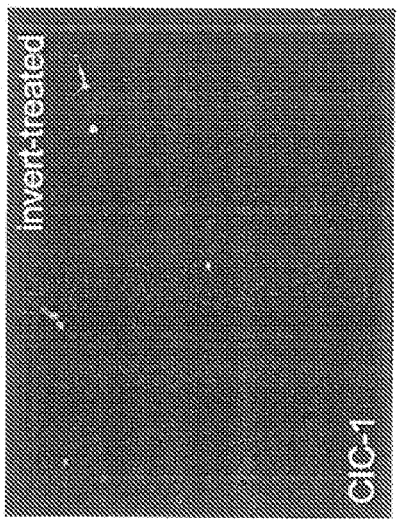
Figure 29C:
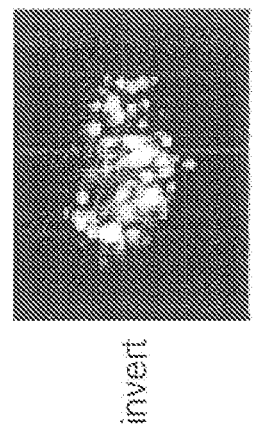
FIGS. 29A, 29B, 29C, 29D, 29E, and 29F show that antisense morpholino had no effect on the formation of ribonuclear inclusions. Fluorescence in situ hybridization and immunofluorescence demonstrate co-localization of CUG$_{exp}$ RNA and MBNL1 protein in muscle nuclei (blue) 3 weeks after injection of HSA$_{LR}$ TA muscle with invert (FIG. 29a-c) and antisense (FIG. 29d-f) morpholino.
Figure 29F:
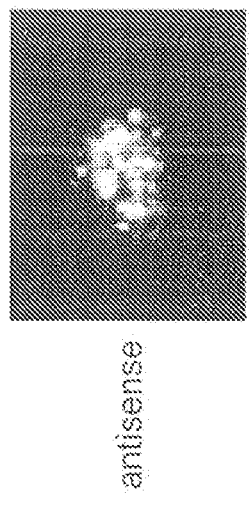
Figure 29B:
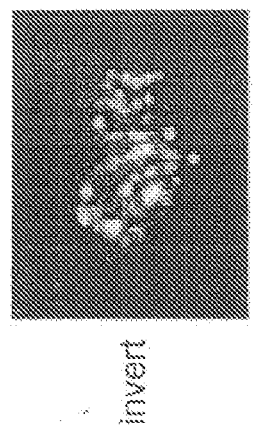
Figure 29E:
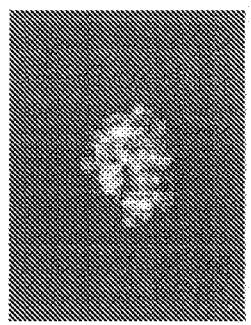
Figure 29A:
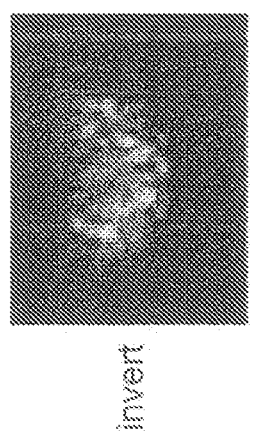
Figure 29D:
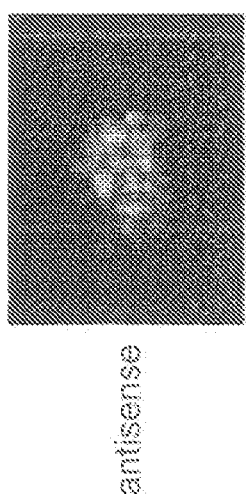

Homozygous deletion of Mbnl1 exon 3 in mice ($Mbnl1^{\Delta E3/\Delta E3}$) resulted in loss of Mbnl1 protein from muscle, spliceopathy that is similar to DM1 patients and $HSA^{LR}$ mice, reduction of ClC-1 expression and activity, and myotonia (Kanadia, R. N., et al. (2003) Science 302:1978-1980; Lin, X., et al. (2006) Hum Mol Genet 15:2087-2097; Lueck, J. D., et al. (2007) J Gen Physiol 129:79-94). To examine the effects of AON in this model, antisense morpholino or invert control was injected into TA muscle of $Mbnl1^{\Delta E3/\Delta E3}$ mice. As in the $HSA^{LR}$ transgenic model, antisense morpholino repressed the inclusion of exon 7a (FIG. 27A,B), increased the expression of ClC-1 protein at the sarcolemma (FIG. 27C,D), and reduced the myotonia in $Mbnl1^{\Delta E3/\Delta E3}$ mice (FIG. 27E). Thus, while the pathogenesis of spliceopathy in DM is a subject of debate, rescue of the myotonia by antisense morpholino does not depend on the exact manner in which the ClC-1 splicing defect is generated.

b) Discussion

Current models of DM1 pathogenesis postulate that DMPK mRNA containing an expanded CUG repeat alters the function of splicing factors, leading to misregulated alternative splicing for a specific group of pre-mRNAs (Philips, A. V., et al. (1998) Science 280:737-741). In operational terms, one difficulty with this model is that functional differences between alternative splice isoforms, or biological consequences of altering the ratio of two alternative splice products, are not easy to determine. Furthermore, in the context of dozens to hundreds of transcripts whose splicing is so affected, the phenotypic consequences of any particular splicing change may be difficult to ascertain. A key finding of the present study is that misregulated alternative splicing of ClC-1 is required for the development of myotonia, a cardinal symptom of DM1, in both $HSA^{LR}$ and $Mbnl1^{\Delta E3/\Delta E3}$ mice. These results provide the clearest indication to date that $CUG^{exp}$-induced spliceopathy is directly involved in producing a clinical feature of DM1. Furthermore, the results indicate an approach for dissecting the functional significance of any particular splicing change. Antisense oligonucleotides can be used to correct a specific splicing defect in DM1 cells, or to induce a DM1-like effect in WT cells.

Myotonia is the symptom by which DM1 is most often recognized, and, due to preferential involvement of hand and forearm muscles, it compromises the manual dexterity and contributes to disability. In light of the abnormal calcium homeostasis observed in DM1 cells and model systems (Benders, A. A., et al. (1997) J Clin Invest 100:1440-1447; Benders, A. A., et al. (1996) Acta Physiol Scand 156:355-367), and the effects of DM1 on alternative splicing of the SERCA1 calcium reuptake pump of the sarcoplasmic reticulum (Kimura, T., et al. (2005) Hum Mol Genet 14:2189-2200; Lin, X., et al. (2006) Hum Mol Genet 15:2087-2097), it also seems that excessive calcium release due to myotonic discharges aggravate the degeneration of DM1 muscle fibers. Although previous studies have implicated sodium channels or calcium-activated potassium channels in DM1 (Franke, C., et al. (1990) J Physiol 425:391-405; Renaud, J. F., et al. (1986) Nature 319:678-680; Behrens, M. I., et al. (1994) Muscle Nerve 17:1264-1270), a second finding of the present study is confirmation that DM1-associated myotonia results primarily from a chloride channelopathy.

The number of functional ClC-1 channels in the sarcolemma was markedly decreased, the rate of channel deactivation was increased, and the maximum ClC-1 channel open probability was reduced in both $HSA^{LR}$ and $Mbnl1^{\Delta E3/\Delta E3}$ mice (Lueck, J. D., et al. (2007) J Gen Physiol 129:79-94). The observed acceleration in channel deactivation and reduction in maximal channel open probability are consistent with previously reported dominant negative effects imparted by exon 7a encoded protein products (Berg, J., et al. (2004) Neurology 63:2371-2375). The observations that electroporation of AON in HSA$^{LR}$ muscle reduced levels of exon 7a-containing transcript (FIG. 25D,E), increased full length ClC-1 transcript (FIG. 25F), and completely normalized ClC-1 current density (FIG. 26B) and deactivation gating (FIG. 26D) supports the assertion that chloride channelopathy in DM1 involves a complex combination of transdominant RNA- and protein-based mechanisms.

AONs influence RNA processing by annealing to pre-mRNA and blocking the access of splicing factors to splice sites or cis-acting regulatory elements (Dominski, Z., and Kole, R. (1993) Proc Natl Acad Sci USA 90:8673-8677). AONs that induce skipping of constitutively spliced exons have been used to bypass stop codons or restore the proper reading frame in the dystrophin mRNA (Dunckley, M. G., et al. (1998) Hum Mol Genet 7:1083-1090; Wilton, S. D., et al. (1999) Neuromuscul Disord 9:330-338; Alter, J., et al. (2006) Nat Med 12:175-177). Exon 7a can show heightened susceptibility to AONs because splicing signals in alternative exons tend to be intrinsically weak and this exon is normally skipped in a fraction of ClC-1 transcripts (Lueck, J. D., et al. (2007) Am J Physiol Cell Physiol 292:C1291-1297). However, ClC-1 mRNAs that include exon 7a contain premature termination codons and undergo rapid degradation (Lueck, J. D., et al. (2007) Am J Physiol Cell Physiol 292:C1291-1297). Therefore, these splice products are underrepresented at steady state, and the exact efficiency of AON-induced exon skipping was not determined Despite this limitation, the decrease of exon 7a+ isoforms to WT levels and the normalized activity of ClC-1 channels in treated muscle fibers indicates that this intervention is highly effective and surprisingly prolonged.

These results are the first to show that symptoms of DM1 are reversible using a targeted, non-gene therapeutic approach to restore a normal pattern of alternative splicing. While several drugs with anti-myotonia properties are currently available, they provide only partial relief of symptoms, and their use in DM1 is limited by the lack of controlled trials supporting their efficacy and safety (Trip, J., et al. (2006) Cochrane Database Syst Rev:CD004762). Results here indicate that targeting the ClC-1 splicing defect is highly effective for treating the myotonia in DM1.

c) Methods (1) Design of Oligonucleotides.

Morpholino oligonucleotides (Gene Tools LLC) were 5'-CCAGGCACGGTctgcaacagagaag-3' (SEQ ID NO: 4) targeting the ClC-1 3' splice site, 5'-gaagagacaacgtctggcacggacc-3' (SEQ ID NO: 5) inverted control, and 5'-ggaagtgaaacttgcCTCCATCAGG-3' (SEQ ID NO: 6) targeting the ClC-1 5' splice site.

(2) Morpholino Injections.

HSA$^{LR}$ (Mankodi, A., et al. (2000) Science 289:1769-1773) or Mbnl1$^{\Delta E3/\Delta E3}$ mice (Kanadia, R. N., et al. (2003) Science 302:1978-1980) were anesthetized by intraperitoneal injection of 100 mg/kg ketamine, 10 mg/kg xylazine, and 3 mg/kg acepromazine. TA muscle was pretreated by intramuscular injection of bovine hyaluronidase (15 µl, 0.4 U/µl) (Sigma) (McMahon, J. M., et al. (2001) Gene Ther 8:1264-1270). Two hours later, 10 or 20 µg of morpholino in a total volume of 20 µl phosphate buffered saline (PBS) was injected using a 30-gauge needle. TA muscle was then electroporated using electrodes placed parallel to the long axis of the muscle. Electroporation parameters were 100V/cm, 10 pulses at 1 Hz, and 20 ms duration per pulse. Antisense or control morpholino with inverted sequence was injected into TA muscles of opposite limbs. The determination of which TA received antisense morpholino was randomized, and investigators remained blinded to this assignment until EMG analyses were completed. Other analyses were performed without blinding. For experiments to determine the distribution of injected oligos, the antisense morpholino was labeled with carboxyfluorescein and cryosections of muscle (10 µM) were examined by fluorescence microscopy, with or without fixation in 4% paraformaldehyde. Some sections were co-labeled with TRITC-wheat germ agglutinin (Parsons, S. A., et al. (2003) Mol Cell Biol 23:4331-4343) (50 µg/ml in PBS; Sigma) and 4',6-diamidino-2-phenylindole (DAPI) to highlight the surface membranes and nuclei of muscle fibers.

(3) RNA Analysis.

Mice were sacrificed three or eight weeks after morpholino injection. TA muscles were removed and frozen in liquid nitrogen. Total RNA was isolated with TriReagent (Molecular Research Center). cDNA synthesis was primed with oligo dT as described previously (Mankodi, A., et al. (2002) Mol Cell 10:35-44). Assays for alternative splicing of ClC-1 and Titin were described previously (Mankodi, A., et al. (2002) Mol Cell 10:35-44; Lin, X., et al. (2006) Hum Mol Genet 15:2087-2097). Primer sequences were ClC-1 forward: ClCm-7 5'-TGAAGGAATACCTCACACTCAAGG-3' (SEQ ID NO: 7) and reverse: ClCm-30 5'-CACGGAACACAAAGGCACTG-3' (SEQ ID NO: 8); mTitin forward: mTTN1 5'-GTGTGAGTCGCTCCAGAAACG-3' (SEQ ID NO: 9) and reverse: mTTN2 5'-CCACCACAGGACCATGTTATTTC-3' (SEQ ID NO: 10).

RT-PCR products (22 cycles) were separated on agarose gels, stained with SYBR green II, and scanned on a laser fluorimager (Molecular Dynamics). Band intensity was quantified using ImageQuant software. Total levels of ClC-1 mRNA were determined by quantitative real-time RT-PCR (Taqman, Applied Biosystems) relative to housekeeping gene RNA polymerase II transcription factor IIB.

(4) Immunofluorescence.

Frozen transverse sections of TA muscle (10 µM) were stained with affinity-purified rabbit polyclonal anti-ClC-1 antibody (1:50; Alpha Diagnostic International) as previously described (Kanadia, R. N., et al. (2006) Proc Natl Acad Sci USA 103:11748-11753). Muscle sections from ClC-1 null mice and WT FVB mice served as negative and positive controls on each slide. Z-plane stacks consisting of 8 images separated by 0.25 µM were captured and deconvolved using Autoquant v9.3 software (Autoquant Imaging). Maximum-projection images were obtained using Metavue software (Universal Imaging Corporation). Exposure time and thresholding were identical for all comparisons of antisense vs. invert controls.

(5) Macroscopic Recordings of ClC-1 Current.

Delivery of antisense and invert morpholinos into FDB fibers was achieved by injection and electroporation of hindlimb footpads. Briefly, 12-14-day-old HSA$^{LR}$ mice were anesthetized by intraperitoneal injection of 100 mg/kg ketamine, 10 mg/kg xylazine, and 3 mg/kg acepromazine. Hindlimb foot pads then were injected with bovine hyaluronidase followed 1 hour later with 20 µg (10 µl, 2 µg/µl in PBS) of antisense or invert carboxyfluorescein-labeled morpholino. Uptake of morpholinos was enhanced by electroporation (100 V/cm, 20 pulses at 1 Hz, and 20 ms per pulse) of the foot pad immediately after injection (DiFranco, M., et al. (2006) Protein Expr Purif 47:281-288). Three to five days after injection/electroporation, individual FDB muscle fibers were isolated as previously described (Lueck, J. D., et al. (2007) J Gen Physiol 129:79-94). Brightfield and fluorescence (488 nm excitation) images of single FDB fibers were acquired using a 40× (1.4 NA) objective and a TILL IMAGO QE cooled-CCD camera. Only fibers exhibiting clear striations, clean surfaces and green fluorescence were chosen for electrophysiological recordings. ClC-1 currents were measured and analyzed in whole cell patch clamp experiments (Hamill, O. P., et al. (1981) Pflugers Arch 391:85-100) using an approach identical to that described in detail elsewhere (Lueck, J. D., et al. (2007) J Gen Physiol 129:79-94). ClC-1 current density (pA/pF) was calculated in order to compare data across fibers of different sizes.

(6) Electromyography (EMG).

EMG was performed under general anesthesia as described previously (Kanadia, R. N., et al. (2003) Science 302:1978-1980). Images and video recordings of electromyographic myotonia in HSA$^{LR}$ and Mbnl1$^{\Delta E3/\Delta E3}$ mice are shown in previous reports (Kanadia, R. N., et al. (2003) Science 302: 1978-1980; Mankodi, A., et al. (2000) Science 289:1769-1773). A minimum of 15 needle insertions were performed for each muscle examined Myotonic discharges were graded on a 4 point scale: 0, no myotonia; 1, occasional myotonic discharge in <50% of needle insertions; 2, myotonic discharge in >50% of needle insertions; 3: myotonic discharge with nearly every insertion.

(7) Statistical Analysis.

Group data are expressed as mean±s.d., except for patch clamp data in FIG. 26 which are expressed as mean±s.e.m. Between group comparison was performed by two-tailed t-test or two way ANOVA as indicated.

10. Example 10

Figure 30A:
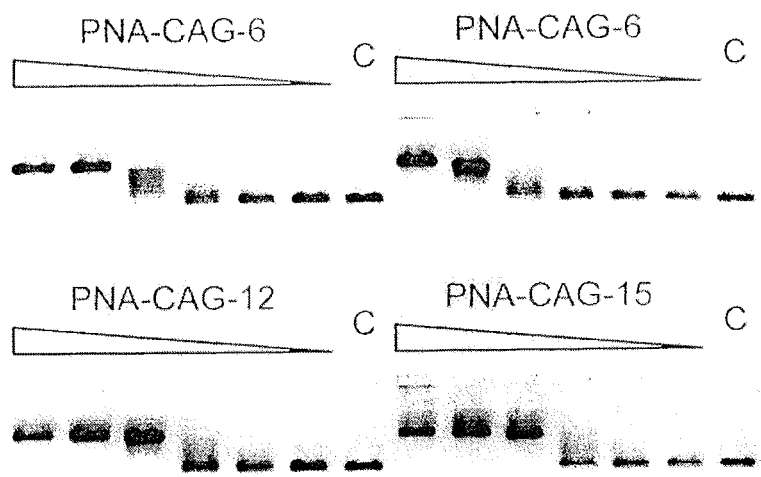
FIGS. 30A and 30B show protein displacement therapy with peptide nucleic acid (PNA) oligomers composed of CAG repeats.
Figure 30B:
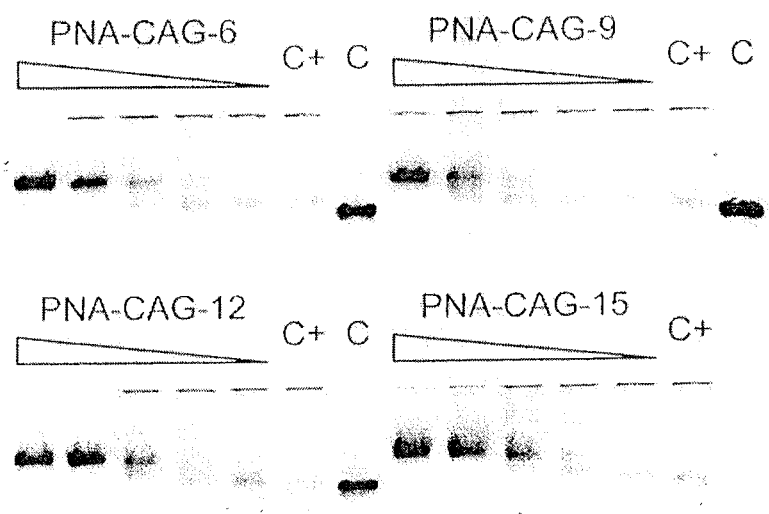
Figure 31:
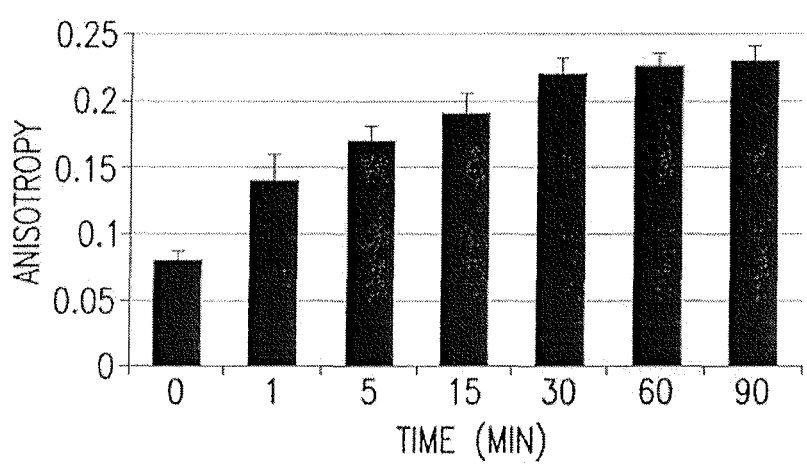
FIG. 31 shows screening for compounds that inhibit interaction of MBNL1 protein and CUG expansion RNA: fluorescence anisotropy assay shows interaction of CUG expansion RNA with recombinant MBNL1 protein in vitro. Fluorescein-labeled (CUG)$_{36}$ RNA (2 nM) was incubated with MBNL1 protein (100 nM) and anisotropy was measured at time points ranging from 1 to 90 minutes. Increasing values for fluorescence anisotropy indicate interaction of fluorescein-labeled (CUG)$_{36}$ transcript with MBNL1 protein. Values are averages from 4 experiments and error bars shows SD.
Figure 32:
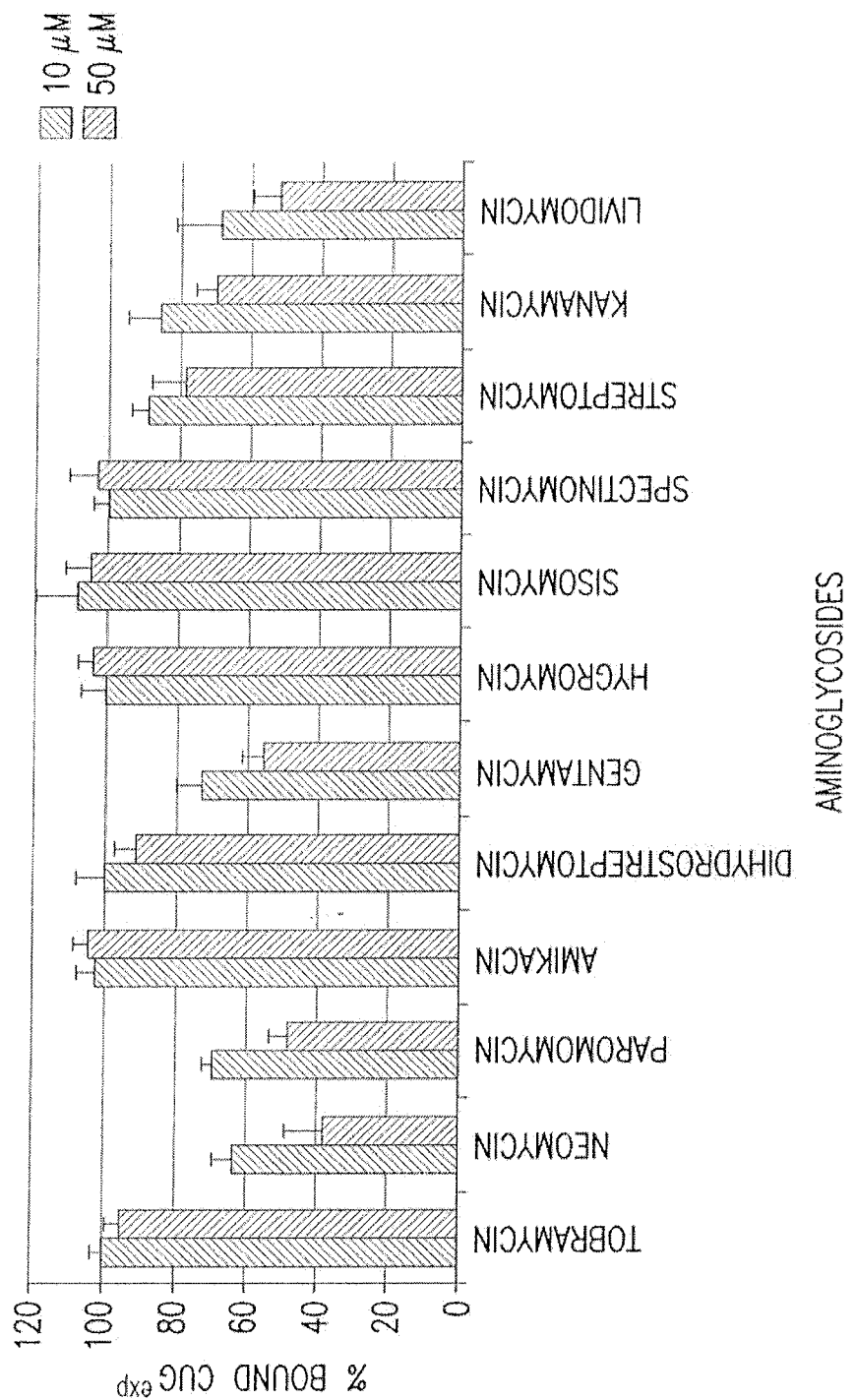
FIG. 32 shows a fluorescence anisotropy assay to screen for compounds that inhibit interaction of CUG repeat RNA with recombinant MBNL1 protein. Fluorescein-labeled (CUG)$_{36}$ transcript (2 nM) was incubated first with aminoglycoside compound (10 or 50 µM) and then with excess amount of recombinant MBNL1 protein (100 nM). To calculate the fraction of CUG repeat RNA that remains bound to MBNL1 protein ("% bound CUG$^{exp}$", vertical axis), results are expressed as the percentage of maximal fluorescence anisotropy in assays from which aminoglycosides were omitted. Among the compounds tested, neomycin showed the strongest inhibition of MBNL1 binding to CUG repeat RNA. Values are the average +/−SD from three measurements.
Figure 33A:
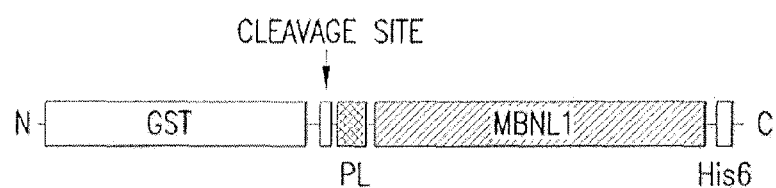
FIGS. 33A and 33B.
Figure 33B:
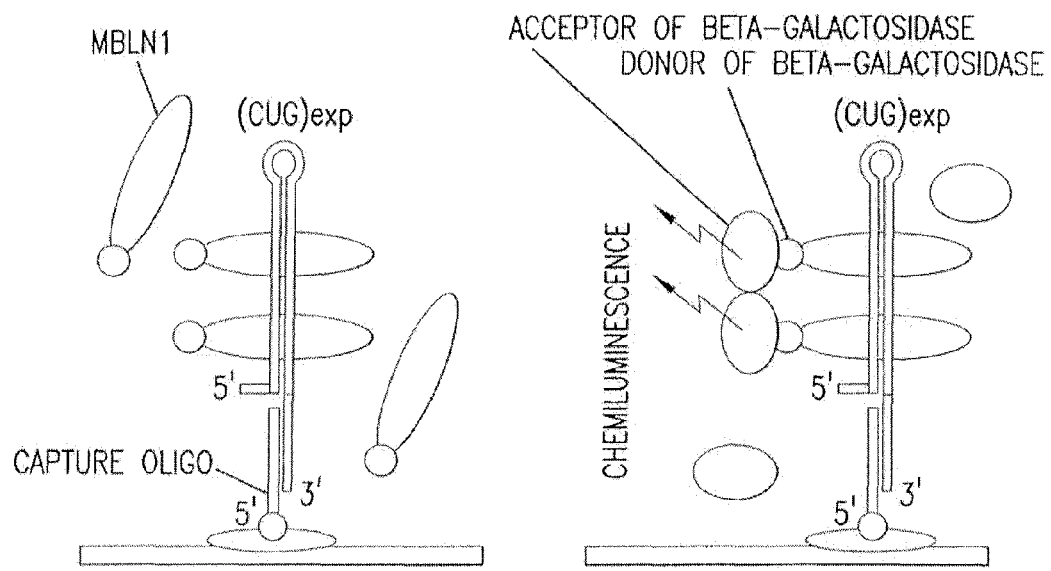
Figure 34A:
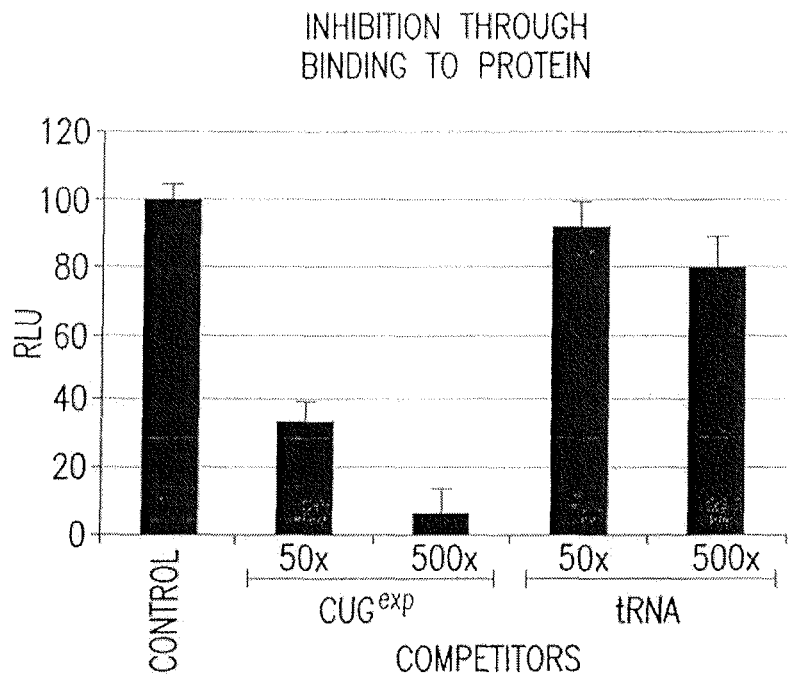
FIGS. 34A and 34B show enzymatic complementation assay to screen for compounds that inhibit interaction of CUG repeat RNA with recombinant MBNL1 protein. Operation of the beta-galactosidase enzymatic complementation assay was demonstrated using two kinds of inhibitors. On the top panel (FIG. 34A), excess soluble $(CUG)_{109}$ RNA was added to the assay reaction. The soluble $(CUG)_{109}$ RNA binds to MBNL1-PL protein and prevents its retention on the microtiter plate, reflected by reduced beta-galactosidase activity (expressed on the vertical axis in terms of relative luminescence activity). On the bottom panel (FIG. 34B), compounds having the ability to intercalate into CUG-repeat-RNA-hairpins (EtBr, ethidium bromide; or SybrGreen stain) were added at the indicated concentrations. Both compounds reduce the amount of MBNL1-PL retained on plate, reflected by reduced beta-galactosidase activity.
Figure 34B:
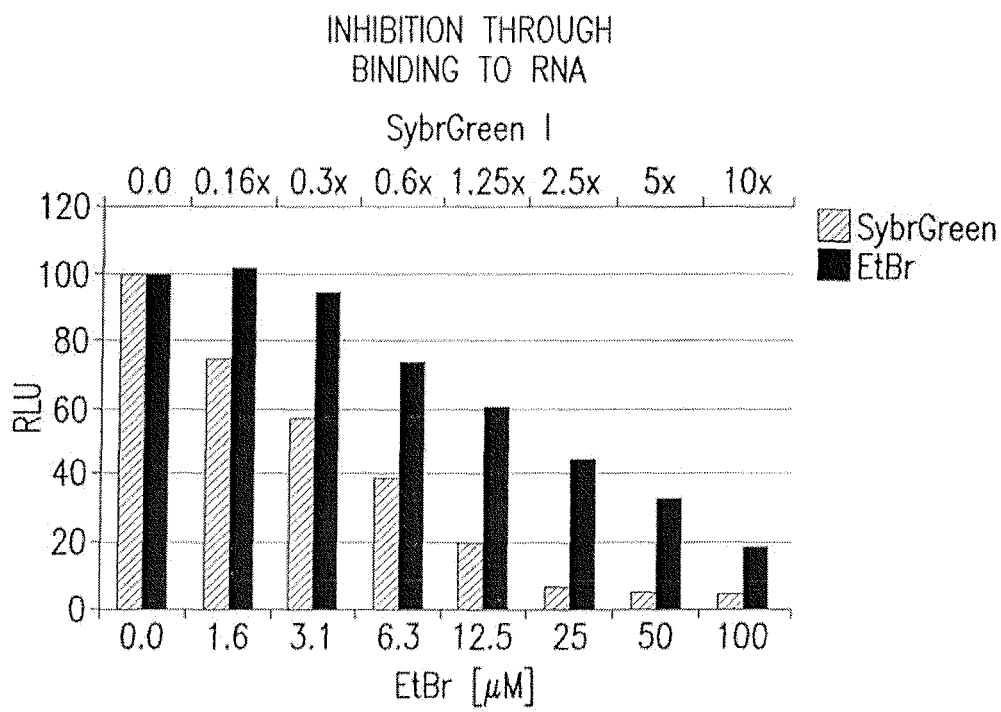

Protein Displacement Therapy with Peptide Nucleic Acid (PNA) Oligomers Composed of CAG Repeats Previously it was shown that expanded CUG repeat RNA forms stable hairpin structures (Tian B, et al. RNA 2000; 6:79-87). FIG. 30A shows that PNA-CAG repeat oligos of lengths ranging from 2 to 5 CAG repeats can invade (CUG) 109 hairpins and effectively interact with expanded CUG repeat hairpin structures in vitro. FIG. 30B shows that these PNA-CAG oligos can also inhibit the interaction of (CUG) 109 RNA with MBNL1 protein in vitro. FIG. 30A was performed by non-denaturing polyacrylamide gel scanned with laser fluorimager shows migration of fluorescein-labeled (CUG)109 transcript (10 nM). This transcript was incubated 30 min with different concentrations (8, 4, 2, 1, 0.5, 0.25 µM) of PNAs containing different length of CAG repeat sequence (PNA-CAG-6, Nterm-CAGCAG; PNA-CAG-9, Nterm-CAGCAGCAG; PNA-CAG-12, Nterm-CAGCAGCAGCAG (SEQ ID NO: 14); or PNA-CAG-15, Nterm-CAGCAGCAG-CAGCAG) (SEQ ID NO: 15). FIG. 30B provides a variation including 5 PNA concentrations (4, 2, 1, 0.5, 0.25 µM) and after additional 30 min incubation step with recombinant MBNL1 (200 nM). Lane "C" in each panel is a control showing migration of fluorescein-labeled (CUG)109 transcript without PNA or MBNL1. Rapid migration of this transcript is caused by hairpin formation. Panel "A" shows that CAG-repeat PNA is able to interact with (CUG)109 transcript, retarding its migration on gel. Lanes "C+" in panel "B" show controls that contain (CUG)109 transcript and MBNL1 protein without PNA. These lanes show diffuse smear of (CUG) 109 transcript, due to formation of heterogenous high molecular weight RNA-protein complexes. Addition of PNA displaces the MBNL1 protein from expanded CUG repeat RNA, disrupting these complexes and reconstituting a sharp band of (CUG)109 transcript. Thus, disclosed herein is the use of antisense oligonucleotides as protein displacement therapy in myotonic dystrophy. It is disclosed herein that myotonic dystrophy has a unique disease process that makes it quite susceptible to treatment: function of a group of proteins, the muscleblind (MBNL) proteins, is compromised because they are stuck onto a mutant RNA that contains CUG repeats, i.e., the proteins are sequestered. Earlier examples disclosed herein were concerned with the use of antisense oligonucleotides that have the morpholino chemistry: CAG25. Herein, is evidence that antisense oligonucleotides having the same sequence (CAG repeats, antisense to CUG repeats) but a different chemistry, peptide nucleic acids (PNAs), are also effective.

11. Example 11

In Vivo Treatment of a Mouse Model for DM Using PNA-CAG

Figure 35:
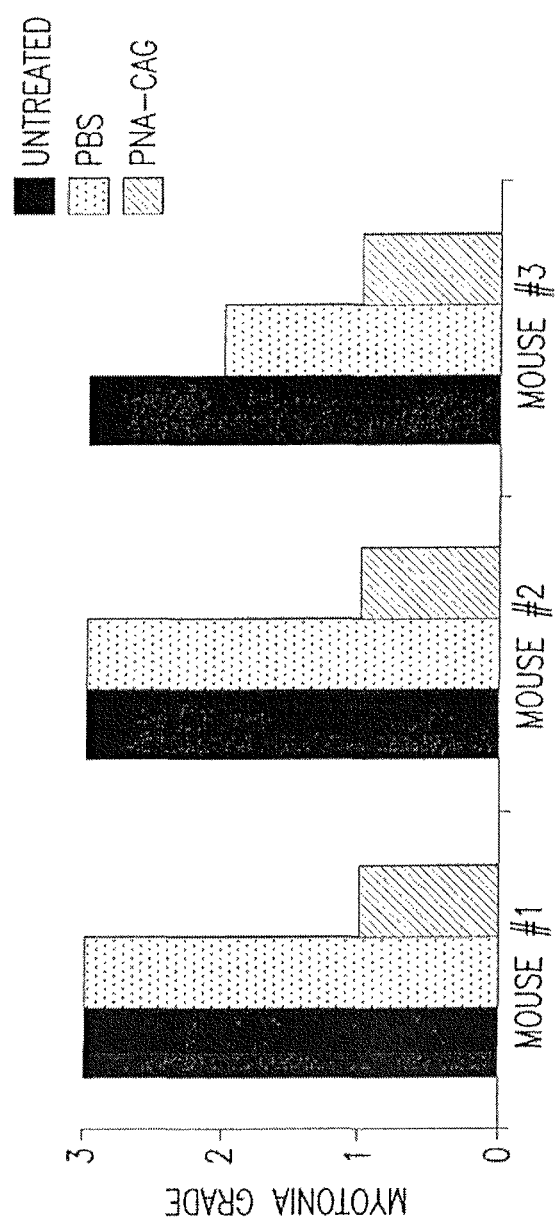
FIG. 35 shows that injection of peptide nucleic acid (PNA) comprised of CAG repeats caused reduction of electromyographic myotonia in HSALR transgenic mouse model of myotonic dystrophy. PNA-(CAG)6mer or PNA-(CAG)9mer (i.e., 2 or 3 CAG repeats) was injected into tibialis anterior muscle on a single occasion. Myotonia was assessed by electromyography 3 weeks following the intramuscular injection. As control, vehicle alone (phosphate buffered saline) was injected in the tibialis anterior muscle of the contralateral limb. All mice had robust action myotonia prior to treatment. Assignment as to which limb received PNA vs control was randomized, and EMG analysis was performed blinded to this assignment.

FIG. 35 shows that injection of peptide nucleic acid (PNA) comprised of CAG repeats caused reduction of electromyographic myotonia in HSA$^{LR}$ transgenic mouse model of myotonic dystrophy. PNA-(CAG)6mer or PNA-(CAG)9mer (i.e., 2 or 3 CAG repeats) was injected into tibialis anterior muscle on a single occasion. Myotonia was assessed by electromyography 3 weeks following the intramuscular injection. As control, vehicle alone (phosphate buffered saline) was injected in the tibialis anterior muscle of the contralateral limb. All mice had robust action myotonia prior to treatment. Assignment as to which limb received PNA vs control was randomized, and EMG analysis was performed blinded to this assignment.

12. Example 12

Screening for Compounds that Inhibit Interaction of MBNL1 Protein and CUG Expansion RNA: Fluorescence Anisotropy Assay Shows Interaction of CUG Expansion RNA with Recombinant MBNL1 Protein In Vitro Fluorescein-labeled (CUG)$_{36}$ RNA (2 nM) was incubated with MBNL1 protein (100 nM) and anisotropy was measured at time points ranging from 1 to 90 minutes. Increasing values for fluorescence anisotropy indicate interaction of fluorescein-labeled (CUG)$_{36}$ transcript with MBNL1 protein. Values are averages from 4 experiments and error bars shows SD.

13. Example 13

Fluorescence Anisotropy Assay to Screen for Compounds that Inhibit Interaction of CUG Repeat RNA with Recombinant MBNL1 Protein MBNL1 protein is known to bind CUG repeat RNAs that form a stable secondary structure (hairpin structure). Aminoglycoside antibiotics were examined to determine whether these compounds can inhibit the interaction of MBNL1 protein with CUG repeat RNA. Aminoglycosides were selected because they are known to bind structured RNA. Fluorescein-labeled (CUG)$_{36}$ transcript (2 nM) was incubated first with aminoglycoside compound (10 or 50 µM) and then with excess amount of recombinant MBNL1 protein (100 nM). To calculate the fraction of CUG repeat RNA that remains bound to MBNL1 protein ("% bound CUG$^{exp}$", vertical axis), results are expressed as the percentage of maximal fluorescence anisotropy in assays from which aminoglycosides were omitted. Among the compounds tested, neomycin showed the strongest inhibition of MBNL1 binding to CUG repeat RNA. Values are the average +/−SD from three measurements.

14. Example 14

Diagram of Enzymatic Complementation Assay to Screen for Compounds that Inhibit Interaction of CUG Repeat RNA with Recombinant MBNL1 Protein $(CUG)_{109}$ transcripts are tethered to the surface of a streptavidin-coated microtiter plate using a capture oligonucleotide that is biotinylated. The capture oligo anneals to complementary sequence at the 3' end of the CUG repeat RNA. Recombinant human MBNL1 is expressed as a fusion with the PL fragment of beta-galactosidase. PL is a 55 amino acid fragment of beta-galactosidase. Preliminary experiments determined that fusion of MBNL1 with the PL fragment did not inhibit the binding of MBNL1 protein to CUG repeat RNA. After incubation with test compound, unbound MBNL1-PL is washed away (panel B). Next, the complementing fragment of beta-galactosidase is added to determine the amount of MBNL1-PL that continues to interact with $(CUG)_{109}$ RNA and thereby is retained on the microtiter plate. The binding of complementing fragment of beta-galactosidase to PL reconstitutes its enzymatic activity. This activity is then determined by adding substrate to provide a fluorescence or chemiluminescence signal from active beta-galactosidase.

15. Example 15

Enzymatic Complementation Assay to Screen for Compounds that Inhibit Interaction of CUG Repeat RNA with Recombinant MBNL1 Protein Operation of the beta-galactosidase enzymatic complementation assay was demonstrated using two kinds of inhibitors. On the left panel, excess soluble $(CUG)_{109}$ RNA was added to the assay reaction. The soluble $(CUG)_{109}$ RNA binds to MBNL1-PL protein and prevents its retention on the microtiter plate, reflected by reduced beta-galactosidase activity (expressed on the vertical axis in terms of relative luminescence activity). On the right panel, compounds having the ability to intercalate into CUG-repeat-RNA-hairpins (EtBr, ethidium bromide; or SybrGreen stain) were added at the indicated concentrations. Both compounds reduce the amount of MBNL1-PL retained on plate, reflected by reduced beta-galactosidase activity. These results show that the enzymatic complementation assay can identify compounds that inhibit MBNL1-CUG interaction either by binding to MBNL1 protein or binding to CUG repeat RNA.

E. REFERENCES

Alter, J., Lou, F., Rabinowitz, A., Yin, H., Rosenfeld, J., Wilton, S. D., Partridge, T. A., and Lu, Q. L. 2006. Systemic delivery of morpholino oligonucleotide restores dystrophin expression bodywide and improves dystrophic pathology. Nat Med 12:175-177.

Amack J D, Mahadevan M S. The myotonic dystrophy expanded CUG repeat tract is necessary but not sufficient to disrupt C2C12 myoblast differentiation. Hum Mol Genet 2001; 10(18):1879-1887.

Amack J D, Paguio A P, Mahadevan M S. Cis and trans effects of the myotonic dystrophy (DM) mutation in a cell culture model. Hum Mol Genet 1999; 8(11):1975-1984.

Behrens, M. I., Jalil, P., Serani, A., Vergara, F., and Alvarez, O. 1994. Possible role of apamin-sensitive K+ channels in myotonic dystrophy. Muscle Nerve 17:1264-1270.

Benders, A. A., Groenen, P. J., Oerlemans, F. T., Veerkamp, J. H., and Wiering a, B. 1997. Myotonic dystrophy protein kinase is involved in the modulation of the Ca2+ homeostasis in skeletal muscle cells. J Clin Invest 100:1440-1447.

Benders, A. A., Wevers, R. A., and Veerkamp, J. H. 1996. Ion transport in human skeletal muscle cells: disturbances in myotonic dystrophy and Brody's disease. Acta Physiol Scand 156:355-367.

Berg, J., Jiang, H., Thornton, C. A., and Cannon, S. C. 2004. Truncated ClC-1 mRNA in myotonic dystrophy exerts a dominant-negative effect on the Cl current. Neurology 63:2371-2375.

Bittker J A, Le B V, Liu D R. Nucleic acid evolution and minimization by nonhomologous random recombination. Nat Biotechnol 2002; 20(10):1024-1029.

Blakely B T, Rossi F M, Tillotson B, Palmer M, Estelles A, Blau H M. Epidermal growth factor receptor dimerization monitored in live cells. Nat Biotechnol 2000; 18(2):218-222.

Brook J D, McCurrach M E, Harley H G, Buckler A J, Church D, Aburatani H et al. Molecular basis of myotonic dystrophy: expansion of a trinucleotide (CTG) repeat at the 3' end of a transcript encoding a protein kinase family member. Cell 1992; 68(4):799-808.

Chalberg T W, Portlock J L, Olivares E C, Thyagarajan B, Kirby P J, Hillman R T et al. Integration specificity of phage phiC31 integrase in the human genome. J Mol Biol 2006; 357(1):28-48.

Charlet, B. N., Savkur, R. S., Singh, G., Philips, A. V., Grice, E. A., and Cooper, T. A. 2002. Loss of the muscle-specific chloride channel in type 1 myotonic dystrophy due to misregulated alternative splicing. Mol Cell 10:45-53.

Chung J H, Bell A C, Felsenfeld G. Characterization of the chicken beta-globin insulator. Proc Natl Acad Sci USA 1997; 94(2):575-580.

Dansithong W, Paul S, Comai L, Reddy S. MBNL1 is the primary determinant of focus formation and aberrant insulin receptor splicing in DM1. J Biol Chem 2005; 280(7): 5773-5780.

Davis B M, McCurrach M E, Taneja K L, Singer R H, Housman D E. Expansion of a CUG trinucleotide repeat in the 3' untranslated region of myotonic dystrophy protein kinase transcripts results in nuclear retention of transcripts. Proc Natl Acad Sci USA 1997; 94(14):7388-7393.

DiFranco, M., Neco, P., Capote, J., Meera, P., and Vergara, J. L. 2006. Quantitative evaluation of mammalian skeletal muscle as a heterologous protein expression system. Protein Expr Purif 47:281-288.

Dominski, Z., and Kole, R. 1993. Restoration of correct splicing in thalassemic pre-mRNA by antisense oligonucleotides. Proc Natl Acad Sci USA 90:8673-8677.

Dunckley, M. G., Manoharan, M., Villiet, P., Eperon, I. C., and Dickson, G. 1998. Modification of splicing in the dystrophin gene in cultured Mdx muscle cells by antisense oligoribonucleotides. Hum Mol Genet 7:1083-1090.

Ebralidze, A., Wang, Y., Petkova, V., Ebralidse, K., and Junghans, R. P. 2004. RNA leaching of transcription factors disrupts transcription in myotonic dystrophy. Science 303: 383-387.

Fardaei M, Larkin K, Brook J D, Hamshere M G. In vivo co-localisation of MBNL protein with DMPK expanded-repeat transcripts. Nucleic Acids Res 2001; 29(13):2766-2771.

Fardaei M, Rogers M T, Thorpe H M, Larkin K, Hamshere M G, Harper P S et al. Three proteins, MBNL, MBLL and MBXL, co-localize in vivo with nuclear foci of expanded-repeat transcripts in DM1 and DM2 cells. Hum Mol Genet 2002; 11(7):805-814.

Franke, C., Hatt, H., Iaizzo, P. A., and Lehmann-Horn, F. 1990. Characteristics of Na+ channels and Cl– conductance in resealed muscle fibre segments from patients with myotonic dystrophy. J Physiol 425:391-405.

Furman, R. E., and Barchi, R. L. 1978. The pathophysiology of myotonia produced by aromatic carboxylic acids. Ann Neurol 4:357-365.

Groth A C, Olivares E C, Thyagarajan B, Calos M P. A phage integrase directs efficient site-specific integration in human cells. Proc Natl Acad Sci USA 2000; 97(11):5995-6000.

Hamill, O. P., Marty, A., Neher, E., Sakmann, B., and Sigworth, F. J. 1981. Improved patch-clamp techniques for high-resolution current recording from cells and cell-free membrane patches. Pflugers Arch 391:85-100.

Hansen S G, Cope T A, Hruby D E. BiZyme: a novel fusion protein-mediating selection of vaccinia virus recombinants by fluorescence and antibiotic resistance. Biotechniques 2002; 32(5):1178, 1180, 1182-1178, 1180, 1187.

Ho T H, Charlet B, Poulos M G, Singh G, Swanson M S, Cooper T A. Muscleblind proteins regulate alternative splicing. EMBO J 2004; 23(15):3103-3112.

Ho T H, Savkur R S, Poulos M G, Mancini M A, Swanson M S, Cooper T A. Colocalization of muscleblind with RNA foci is separable from mis-regulation of alternative splicing in myotonic dystrophy. J Cell Sci 2005; 118(Pt 13):2923-2933.

Ishikawa Y, Tanaka N, Murakami K, Uchiyama T, Kumaki S, Tsuchiya S et al. Phage phiC31 integrase-mediated genomic integration of the common cytokine receptor gamma chain in human T-cell lines. J Gene Med 2006; 8(5):646-653.

Jansen G, Groenen P J T A, Bachner D, Jap P H, Coerwinkel M, Oerlemans F et al. Abnormal myotonic dystrophy protein kinase levels produce only mild myopathy in mice. Nat Genet 1996; 13:316-324.

Kanadia R N, Johnstone K A, Mankodi A, Lungu C, Thornton C A, Esson D et al. A muscleblind knockout model for myotonic dystrophy. Science 2003; 302(5652):1978-1980.

Kanadia R N, Urbinati C R, Crusselle V J, Luo D, Lee Y J, Harrison J K et al. Developmental expression of mouse muscleblind genes Mbnl1, Mbnl2 and Mbnl3. Gene Expr Patterns 2003; 3(4):459-462.

Kanadia, R. N., Johnstone, K. A., Mankodi, A., Lungu, C., Thornton, C. A., Esson, D., Timmers, A. M., Hauswirth, W. W., and Swanson, M. S. 2003. A muscleblind knockout model for myotonic dystrophy. Science 302:1978-1980.

Kanadia, R. N., Shin, J., Yuan, Y., Beattie, S. G., Wheeler, T. M., Thornton, C. A., and Swanson, M. S. 2006. Reversal of RNA missplicing and myotonia after muscleblind overexpression in a mouse poly(CUG) model for myotonic dystrophy. Proc Natl Acad Sci USA 103:11748-11753.

Kang S, Jaworski A, Ohshima K, Wells R D. Expansion and deletion of CTG repeats from human disease genes are determined by the direction of replication in E. coli. Nat Genet 1995; 10(2):213-218.

Kimura, T., Nakamori, M., Lueck, J. D., Pouliquin, P., Aoike, F., Fujimura, H., Dirksen, R. T., Takahashi, M. P., Dulhunty, A. F., and Sakoda, S. 2005. Altered mRNA splicing of the skeletal muscle ryanodine receptor and sarcoplasmic/endoplasmic reticulum Ca2+-ATPase in myotonic dystrophy type 1. Hum Mol Genet 14:2189-2200.

Lin, X., Miller, J. W., Mankodi, A., Kanadia, R. N., Yuan, Y., Moxley, R. T., Swanson, M. S., and Thornton, C. A. 2006. Failure of MBNL1-dependent post-natal splicing transitions in myotonic dystrophy. Hum Mol Genet 15:2087-2097.

Liguori C L, Ricker K, Moseley M L, Jacobsen J F, Kress W, Naylor S L et al. Myotonic dystrophy type 2 caused by a CCTG expansion in intron 1 of ZNF9. Science 2001; 293 (5531):864-867.

Lueck, J. D., Lungu, C., Mankodi, A., Osborne, R. J., Welle, S. L., Dirksen, R. T., and Thornton, C. A. 2007. Chloride channelopathy in myotonic dystrophy resulting from loss of posttranscriptional regulation for CLCN1. Am J Physiol Cell Physiol 292:C1291-1297.

Lueck, J. D., Mankodi, A., Swanson, M. S., Thornton, C. A., and Dirksen, R. T. 2007. Muscle chloride channel dysfunction in two mouse models of myotonic dystrophy. J Gen Physiol 129:79-94.

Mankodi A, Lin X, Blaxall B C, Swanson M S, Thornton C A. Nuclear RNA foci in the heart in myotonic dystrophy. Circ Res 2005; 97(11):1152-1155.

Mankodi A, Logigian E, Callahan L, McClain C, White R, Henderson D et al. Myotonic dystrophy in transgenic mice expressing an expanded CUG repeat. Science 2000; 289 (5485):1769-1773.

Mankodi A, Takahashi M P, Jiang H, Beck C L, Bowers W J, Moxley R T et al. Expanded CUG repeats trigger aberrant splicing of ClC-1 chloride channel pre-mRNA and hyperexcitability of skeletal muscle in myotonic dystrophy. Mol Cell 2002; 35-44.

Mankodi A, Urbinati C R, Yuan Q P, Moxley R T, Sansone V, Krym M et al. Muscleblind localizes to nuclear foci of aberrant RNA in myotonic dystrophy types 1 and 2. Hum Mol Genet 2001; 10:2165-2170.

McMahon, J. M., Signori, E., Wells, K. E., Fazio, V. M., and Wells, D. J. 2001. Optimisation of electrotransfer of plasmid into skeletal muscle by pretreatment with hyaluronidase—increased expression with reduced muscle damage. Gene Ther 8:1264-1270.

Mercatante, D. R., Sazani, P., and Kole, R. 2001. Modification of alternative splicing by antisense oligonucleotides as a potential chemotherapy for cancer and other diseases. Curr Cancer Drug Targets 1:211-230.

Miller J W, Urbinati C R, Teng-umnuay P, Stenberg M G, Byrne B J, Thornton C A et al. Recruitment of human muscleblind proteins to (CUG)(n) expansions associated with myotonic dystrophy. EMBO J 2000; 19(17):4439-4448.

Nagai T, Ibata K, Park E S, Kubota M, Mikoshiba K, Miyawaki A. A variant of yellow fluorescent protein with fast and efficient maturation for cell-biological applications. Nat Biotechnol 2002; 20(1):87-90.

Napierala M, Krzyzosiak W J. CUG repeats present in myotonin kinase RNA form metastable slippery hairpins. J Biol Chem 1997; 272(49):31079-31085.

Novak A, Guo C, Yang W, Nagy A, Lobe C G. Z/EG, a double reporter mouse line that expresses enhanced green fluorescent protein upon Cre-mediated excision. Genesis 2000; 28(3-4):147-155.

Osborne, R. J., and Thornton, C. A. 2006. RNA-dominant diseases. Hum Mol Genet 15 Spec No 2:R162-169.

Parsons, S. A., Wilkins, B. J., Bueno, O. F., and Molkentin, J. D. 2003. Altered skeletal muscle phenotypes in calcineurin Aalpha and Abeta gene-targeted mice. Mol Cell Biol 23:4331-4343.

Philips A V, Timchenko L T, Cooper T A. Disruption of splicing regulated by a CUG-binding protein in myotonic dystrophy. Science 1998; 280(5364):737-741.

Pollitt S K, Pallos J, Shao J, Desai U A, Ma A A, Thompson L M et al. A rapid cellular FRET assay of polyglutamine aggregation identifies a novel inhibitor. Neuron 2003; 40(4):685-694.

Rackham O, Brown C M. Visualization of RNA-protein interactions in living cells: FMRP and IMP1 interact on mRNAs. EMBO J 2004; 23(16):3346-3355.

Reddy S, Smith D B J, Rich M M, Leferovich J M, Reilly P, Davis B M et al. Mice lacking the myotonic dystrophy protein kinase develop a late onset progressive myopathy. Nat Genet 1996; 13:325-334.

Renaud, J. F., Desnuelle, C., Schmid-Antomarchi, H., Hugues, M., Serratrice, G., and Lazdunski, M. 1986. Expression of apamin receptor in muscles of patients with myotonic muscular dystrophy. Nature 319:678-680.

Rizzo M A, Springer G H, Granada B, Piston D W. An improved cyan fluorescent protein variant useful for FRET. Nat Biotechnol 2004; 22(4):445-449.

Saveliev A, Everett C, Sharpe T, Webster Z, Festenstein R. DNA triplet repeats mediate heterochromatin-protein-1-sensitive variegated gene silencing. Nature 2003; 422 (6934): 909-913.

Savkur R S, Philips A V, Cooper T A. Aberrant regulation of insulin receptor alternative splicing is associated with insulin resistance in myotonic dystrophy. Nat Genet 2001; 29(1):40-47.

Seznec H, Agbulut O, Sergeant N, Savouret C, Ghestem A, Tabti N et al. Mice transgenic for the human myotonic dystrophy region with expanded CTG repeats display muscular and brain abnormalities. Hum Mol Genet 2001; 10(23):2717-2726.

Taneja K L, McCurrach M, Schalling M, Housman D, Singer R H. Foci of trinucleotide repeat transcripts in nuclei of myotonic dystrophy cells and tissues. J Cell Biol 1995; 128(6):995-1002.

Thornton C A, Griggs R C, Moxley R T. Myotonic dystrophy with no trinucleotide repeat expansion. Ann Neurol 1994; 35(3):269-272.

Thornton C A, Johnson K, Moxley R T. Myotonic dystrophy patients have larger CTG expansions in skeletal muscle than in leukocytes. Ann Neurol 1994; 35:104-107.

Thyagarajan B, Olivares E C, Hollis R P, Ginsburg D S, Calos M P. Site-specific genomic integration in mammalian cells mediated by phage phiC31 integrase. Mol Cell Biol 2001; 21(12):3926-3934.

Tian B, White R, Xia T, Welle S, Turner D, Mathews M et al. Expanded CUG repeat RNAs form hairpins that activate the double-stranded RNA-dependent protein kinase PKR. Rna 2000; 6:79-87.

Trip, J., Drost, G., van Engelen, B. G., and Faber, C. G. 2006. Drug treatment for myotonia. Cochrane Database Syst Rev:CD004762.

Vicens Q, Westhof E. RNA as a drug target: the case of aminoglycosides. Chembiochem 2003; 4(10):1018-1023.

Wang Y H, Griffith J. Expanded CTG triplet blocks from the myotonic dystrophy gene create the strongest known natural nucleosome positioning elements. Genomics 1995; 25(2):570-573.

Wilton, S. D., Lloyd, F., Carville, K., Fletcher, S., Honeyman, K., Agrawal, S., and Kole, R. Specific removal of the nonsense mutation from the mdx dystrophin mRNA using antisense oligonucleotides. Neuromuscul Disord 9:330-338.

Zhang J H, Chung T D, Oldenburg K R. A Simple Statistical Parameter for Use in Evaluation and Validation of High Throughput Screening Assays. J Biomol Screen 1999; 4(2):67-73.

What is claimed is:

1. A method of treating myotonic dystrophy comprising administering to a subject with myotonic dystrophy an agent that inhibits the interaction of MBNL1 with poly(CUG)$^{exp}$ mRNA, wherein the agent comprises an antisense oligonucleotide, and wherein the antisense oligonucleotide has a nucleobase sequence consisting of 2, 3, 4, 5, 6, 7, 8, 9, 10, 11, or 12 CAG repeats that are fully complementary to the poly(CUG)$^{exp}$.

2. The method of claim 1, wherein the antisense oligonucleotide is a morpholino.

3. The method of claim 1, wherein the antisense oligonucleotide sequence is SEQ ID NO: 3.

4. The method of claim 3, wherein the antisense oligonucleotide is a morpholino.

5. The method of claim 1, wherein the agent comprises a conjugate.

6. The method of claim 1, wherein the antisense oligonucleotide is a peptide nucleic acid.

7. A method of treating myotonic dystrophy in a subject in need thereof comprising administering to the subject an agent that corrects spliceopathy, wherein the agent comprises an antisense oligonucleotide, wherein the antisense oligonucleotide corrects spliceopathy of chloride ion channel ClC-1 in the subject, wherein the antisense oligonucleotide has a nucleobase sequence that is complementary to either the junction between intron 6 and exon 7a of ClC-1 pre-mRNA or the junction between exon 7a and intron 7a of ClC-1 pre-mRNA.

8. The method of claim 7, wherein the antisense oligonucleotide is a morpholino.

9. The method of claim 7, wherein the antisense oligonucleotide has the nucleobase sequence of SEQ ID NO: 4.

10. The method of claim 9, wherein the antisense oligonucleotide is a morpholino.

11. The method of claim 7, wherein the agent is a peptide nucleic acid.

12. The method of claim 7, wherein the agent comprises a conjugate.

13. The method of claim 7, wherein the antisense oligonucleotide has a nucleobase sequence of SEQ ID NO: 6.

* * * * *